(12) United States Patent
Deng et al.

(10) Patent No.: US 10,765,711 B2
(45) Date of Patent: Sep. 8, 2020

(54) REPLICATION COMPETENT ATTENUATED VACCINIA VIRUSES WITH DELETION OF THYMIDINE KINASE WITH AND WITHOUT THE EXPRESSION OF HUMAN FLT3L OR GM-CSF FOR CANCER IMMUNOTHERAPY

(71) Applicant: MEMORIAL SLOAN KETTERING CANCER CENTER, New York, NY (US)

(72) Inventors: Liang Deng, New York, NY (US); Stewart Shuman, New York, NY (US); Jedd Wolchok, New York, NY (US); Taha Merghoub, New York, NY (US); Weiyi Wang, New York, NY (US); Peihong Dai, New York, NY (US); Ning Yang, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/673,475

(22) Filed: Nov. 4, 2019

(65) Prior Publication Data
US 2020/0237839 A1    Jul. 30, 2020

Related U.S. Application Data

(63) Continuation of application No. 16/079,217, filed as application No. PCT/US2017/019548 on Feb. 25, 2017, now Pat. No. 10,512,662.

(60) Provisional application No. 62/300,066, filed on Feb. 25, 2016.

(51) Int. Cl.
| | | |
|---|---|---|
| A61K 38/00 | (2006.01) |
| C07K 14/435 | (2006.01) |
| A61K 39/00 | (2006.01) |
| A61K 39/395 | (2006.01) |
| C07K 14/47 | (2006.01) |
| A61K 35/768 | (2015.01) |
| A61K 35/76 | (2015.01) |
| C07K 14/535 | (2006.01) |
| C07K 14/52 | (2006.01) |
| C07K 16/28 | (2006.01) |
| C12N 15/86 | (2006.01) |
| A61P 35/00 | (2006.01) |
| A61K 48/00 | (2006.01) |

(52) U.S. Cl.
CPC ............ *A61K 35/768* (2013.01); *A61K 35/76* (2013.01); *A61K 39/3955* (2013.01); *A61K 48/00* (2013.01); *A61P 35/00* (2018.01); *C07K 14/521* (2013.01); *C07K 14/535* (2013.01); *C07K 16/2818* (2013.01); *C07K 16/2827* (2013.01); *C12N 15/86* (2013.01); *A61K 2039/505* (2013.01); *C07K 2317/76* (2013.01); *C12N 2710/24121* (2013.01); *C12N 2710/24132* (2013.01); *C12N 2710/24133* (2013.01); *C12N 2710/24143* (2013.01); *C12N 2710/24161* (2013.01)

(58) Field of Classification Search
CPC .. A61K 38/00; A61K 48/00; A61K 2039/505; A61P 35/00; C07K 14/47
See application file for complete search history.

(56) References Cited

U.S. PATENT DOCUMENTS

| | | |
|---|---|---|
| 5,494,807 A | 2/1996 | Paoletti et al. |
| 5,762,938 A | 6/1998 | Paoletti et al. |
| 5,766,882 A | 6/1998 | Falkner et al. |
| 6,004,777 A | 12/1999 | Tartaglia et al. |
| 6,265,189 B1 | 7/2001 | Paoletti |
| 6,372,455 B1 | 4/2002 | Jacobs et al. |
| 6,475,999 B1 | 11/2002 | Mastrangelo et al. |
| 6,548,068 B1 | 4/2003 | Schlom et al. |
| 6,750,043 B2 | 6/2004 | Jacobs et al. |
| 6,761,893 B2 | 7/2004 | Chaplin et al. |
| 6,846,652 B2 | 1/2005 | Jacobs et al. |
| 6,942,855 B2 | 9/2005 | Jacobs et al. |
| 7,001,718 B2 | 2/2006 | Jacobs et al. |
| 7,049,145 B2 | 5/2006 | Erfle et al. |

(Continued)

FOREIGN PATENT DOCUMENTS

| | | |
|---|---|---|
| CA | 2435967 A1 | 1/2005 |
| CA | 2436196 A1 | 1/2005 |

(Continued)

OTHER PUBLICATIONS

Alharbi, et al., "ChAdOx1 and MVA based vaccine candidates against MERS-CoV elicit neutralising antibodies and cellular immune responses in mice," Vaccine, vol. 35, pp. 3780-3788 (Jun. 27, 2017).
Angell et al., "From the immune contexture to the Immunoscore: the role of prognostic and predictive immune markers in cancer," Curr. Opin. Immunol., 25, pp. 261-267 (2013).
Antoine et al., "The complete genomic sequence of the modified vaccinia Ankara strain: comparison with other orthopoxviruses", Virology, 244, pp. 365-396 (1998).
Arsenio et al., "Antagonizing activity of vaccinia virus E3L against human interferons in Huh7 cells," Journal of Virology, vol. 377, No. 1, p. 124-132 (Jul. 20, 2008).

(Continued)

*Primary Examiner* — Barry A Chestnut
(74) *Attorney, Agent, or Firm* — Foley & Lardner LLP

(57) ABSTRACT

The present invention relates generally to the fields of oncology, virology and immunotherapy. More particularly, it concerns the use of poxviruses, specifically the replication competent attenuated vaccinia virus with deletion of thymidine kinase (VC-TK⁻) with and without the expression of human Flt3L or GM-CSF as oncolytic and immunotherapy. The foregoing poxviruses can also be used in combination with immune checkpoint blocking agents. The foregoing poxviruses can also be inactivated via Heat or UV-treatment and the inactivated virus can be used as immunotherapy either alone or in combination with immune checkpoint blocking agents.

19 Claims, 23 Drawing Sheets
Specification includes a Sequence Listing.

(56) References Cited

U.S. PATENT DOCUMENTS

| | | | |
|---|---|---|---|
| 7,208,313 B2 | 4/2007 | McCart et al. |
| 7,252,817 B2 | 8/2007 | Coffey et al. |
| 7,256,037 B2 | 8/2007 | Ellenhorn et al. |
| 7,306,902 B2 | 12/2007 | Thompson et al. |
| 7,431,929 B2 | 10/2008 | Jacobs et al. |
| 7,550,147 B2 | 6/2009 | Howley et al. |
| 7,588,767 B2 | 9/2009 | Szalay et al. |
| 7,807,146 B2 | 10/2010 | Delcayre et al. |
| 8,052,968 B2 | 11/2011 | Chen et al. |
| 8,105,578 B2 | 1/2012 | Roberts et al. |
| 8,377,688 B2 | 2/2013 | Delcayre et al. |
| 8,506,947 B2 | 8/2013 | McCart et al. |
| 8,679,509 B2 | 3/2014 | Evans et al. |
| 8,747,837 B2 | 6/2014 | Kirn et al. |
| 8,778,328 B2 | 7/2014 | Erbs et al. |
| 8,852,927 B2 | 10/2014 | Szalay et al. |
| 8,859,256 B2 | 10/2014 | Szalay et al. |
| 8,865,153 B2 | 10/2014 | Szalay et al. |
| 8,871,219 B2 | 10/2014 | Heeney et al. |
| 9,101,658 B2 | 8/2015 | Contag et al. |
| 9,175,057 B2 | 11/2015 | Schlom et al. |
| 9,180,150 B2 | 11/2015 | Erbs et al. |
| 9,234,197 B2 | 1/2016 | Chaput et al. |
| 9,273,327 B2 | 3/2016 | Cottingham |
| 9,670,506 B2 | 6/2017 | Pantaleo et al. |
| 9,879,281 B2 | 1/2018 | Son et al. |
| 9,919,062 B2 | 3/2018 | Kirn |
| 2002/0061298 A1 | 5/2002 | Coffey et al. |
| 2002/0155529 A1 | 10/2002 | Jacobs et al. |
| 2003/0113919 A1 | 6/2003 | Emtage et al. |
| 2004/0091995 A1 | 5/2004 | Schlom et al. |
| 2004/0208850 A1 | 10/2004 | Ellenhorn et al. |
| 2005/0287162 A1 | 12/2005 | Baier et al. |
| 2006/0088909 A1 | 4/2006 | Compans et al. |
| 2006/0099181 A1 | 5/2006 | Jacobs et al. |
| 2006/0216312 A1 | 9/2006 | Jacobs |
| 2007/0036758 A1 | 2/2007 | Jacobs et al. |
| 2007/0178065 A1 | 8/2007 | Lattime et al. |
| 2007/0275010 A1 | 11/2007 | Feinberg et al. |
| 2008/0075694 A1 | 3/2008 | Drexler et al. |
| 2008/0181870 A1 | 7/2008 | Lowenstein et al. |
| 2009/0162288 A1 | 6/2009 | Chen et al. |
| 2010/0247622 A1 | 9/2010 | Coffey et al. |
| 2010/0316609 A1 | 12/2010 | Dewhurst et al. |
| 2011/0064650 A1 | 3/2011 | Szalay |
| 2011/0142874 A1 | 6/2011 | Jacobs et al. |
| 2011/0206640 A1 | 8/2011 | Bell et al. |
| 2012/0308484 A1 | 12/2012 | Szalay et al. |
| 2012/0328649 A1 | 12/2012 | Falkner et al. |
| 2013/0195912 A1 | 8/2013 | Cottingham |
| 2013/0243813 A1 | 9/2013 | Howley et al. |
| 2013/0295675 A1 | 11/2013 | Jacobs et al. |
| 2014/0086976 A1 | 3/2014 | Szalay et al. |
| 2014/0087362 A1 | 3/2014 | Szalay et al. |
| 2014/0193859 A1 | 7/2014 | Jacobs et al. |
| 2014/0271549 A1 | 9/2014 | Szalay |
| 2014/0377870 A1 | 12/2014 | Jacobs et al. |
| 2015/0037355 A1 | 2/2015 | Kirn et al. |
| 2015/0202272 A1 | 7/2015 | Lauterbach et al. |
| 2015/0240246 A1 | 8/2015 | Jacobs et al. |
| 2015/0250837 A1 | 9/2015 | Nolin et al. |
| 2015/0250869 A1 | 9/2015 | Sene et al. |
| 2015/0283220 A1 | 10/2015 | Mandl et al. |
| 2016/0130564 A1 | 5/2016 | Marais et al. |
| 2016/0185875 A1 | 6/2016 | Cheng et al. |
| 2016/0235793 A1 | 8/2016 | Thorne |
| 2016/0271239 A1 | 9/2016 | Foy et al. |
| 2016/0339090 A1 | 11/2016 | Hacohen et al. |
| 2017/0020938 A1 | 1/2017 | Wang et al. |
| 2017/0021009 A1 | 1/2017 | Jacobs et al. |
| 2017/0106065 A1 | 4/2017 | Foy et al. |
| 2017/0143780 A1 | 5/2017 | Zitvogel et al. |
| 2017/0157188 A1 | 6/2017 | Silvestre et al. |
| 2017/0246280 A1 | 8/2017 | Pantaleo et al. |
| 2017/0266270 A1 | 9/2017 | Foy et al. |
| 2017/0340687 A1 | 11/2017 | Nakao et al. |

FOREIGN PATENT DOCUMENTS

| | | | |
|---|---|---|---|
| CN | 105039269 A | | 11/2015 |
| EP | 2 771 465 A1 | | 5/2013 |
| EP | 2 136 633 B1 | | 10/2015 |
| EP | 3 142 690 A2 | | 4/2017 |
| JP | 2005-502360 A | | 1/2005 |
| JP | 2006-512097 A | | 4/2006 |
| WO | WO-03/023040 A2 | | 3/2003 |
| WO | WO-2004/024756 A2 | | 3/2004 |
| WO | WO-2004/058801 A2 | | 7/2004 |
| WO | WO-2004/003987 A1 | | 8/2004 |
| WO | WO-2006/120474 A2 | | 11/2006 |
| WO | WO-2007/119895 A1 | | 10/2007 |
| WO | WO-2008/045346 A2 | | 4/2008 |
| WO | WO-2008/113078 A1 | | 9/2008 |
| WO | WO2008113078 | * | 9/2008 |
| WO | WO-2009/152179 A1 | | 12/2009 |
| WO | WO-2011/156470 A1 | | 12/2011 |
| WO | WO-2012/009644 A2 | | 1/2012 |
| WO | WO-2013/038066 A1 | | 3/2013 |
| WO | WO-2014/081976 A1 | | 5/2014 |
| WO | WO-2014/036412 A2 | | 6/2014 |
| WO | WO-2015/066715 A1 | | 5/2015 |
| WO | WO-2015/069571 A1 | | 5/2015 |
| WO | WO-2015/084897 A2 | | 6/2015 |
| WO | WO-2015/138741 A1 | | 9/2015 |
| WO | WO-2016/046357 A1 | | 3/2016 |
| WO | WO-2016/128542 A1 | | 8/2016 |
| WO | WO-2016/144564 A1 | | 9/2016 |
| WO | WO-2016/144564 A2 | | 9/2016 |
| WO | WO-2016/168862 A1 | | 10/2016 |
| WO | WO-2016/205429 A1 | | 12/2016 |
| WO | WO-2017/024000 A1 | | 2/2017 |
| WO | WO-2017/037523 A1 | | 3/2017 |
| WO | WO-2017/043815 A1 | | 3/2017 |
| WO | WO-2017/044780 A1 | | 3/2017 |
| WO | WO-2017/075570 A1 | | 5/2017 |
| WO | WO-2017/103291 A1 | | 6/2017 |
| WO | WO-2017/129765 A1 | | 8/2017 |
| WO | WO-2017/147554 A1 | | 8/2017 |
| WO | WO-2017/147554 A2 | | 8/2017 |
| WO | WO-2017/156349 A1 | | 9/2017 |
| WO | WO-2017/205674 A1 | | 11/2017 |
| WO | WO-2018/016917 A1 | | 1/2018 |
| WO | WO-2018/017747 A2 | | 1/2018 |
| WO | WO-2018/031694 A1 | | 1/2018 |
| WO | WO-2018/049248 A1 | | 3/2018 |
| WO | WO-2018/057755 A1 | | 3/2018 |
| WO | WO-2018/058258 A1 | | 4/2018 |

OTHER PUBLICATIONS

Backes et al., "Viral host-range factor C7 or K1 is essential for modified vaccinia virus Ankara late gene expression in human and murine cells, irrespective of their capacity to inhibit protein kinase R-mediated phosphorylation of eukaryotic translation initiation factor 2a," J. of General Virology, vol. 91, pp. 470-482 (Feb. 1, 2010).

Barber, "Innate immune DNA sensing pathways: STING, AIMII and the regulation of interferon production and inflammatory responses", Curr. Opin. Immunol., 23, pp. 10-20 (2011).

Bisht et al., "Severe acute respiratory syndrome coronavirus spike protein expressed by attenuated vaccinia virus protectively immunizes mice," PNAS, vol. 101, pp. 6641-6646 (Apr. 27, 2004).

Bommareddy et al., "MEK inhibition enhances oncolytic virus immunotherapy through increased tumor cell killing and T cell activation," Science Translational Medicine, vol. 10, Issue 471 (Dec. 12, 2018).

Brandler et al., "Preclinical studies of a modified vaccinia virus Ankara-based HIV candidate vaccine: antigen presentation and antiviral effect", J. Virol., vol. 84, No. 10, pp. 5314-5328 (2010).

(56) References Cited

OTHER PUBLICATIONS

Brandt et al., "The N-terminal domain of the vaccinia virus E3L-protein is required for neurovirulence" Virology, vol. 333, No. 2, pp. 263-270 (Mar. 15, 2005).
Brandt, T. et al.; The N-terminal domain of the vaccinia virus E3L-protein is required for neurovirulence, but not induction of a protective immune response. Virology. 2005, 333, No. 2, 263-270.
Breitbach et al., "Targeted and armed oncolytic poxviruses for cancer: the lead example of JX-594," Current Pharmaceutical Biotechnology, 13, pp. 1768-1772 (2012).
Brinkman et al., "Fingolimod (FTY720): discovery and development of an oral drug to treat multiple sclerosis," Nature Reviews | Drug Discovery, vol. 9, pp. 883-897 (Nov. 2010).
Caisova et al., "Innate immunity based cancer immunotherapy: B16-F10 murine melanoma model," BMC Cancer, 16:940, 11 pages (2016).
Cao et al., "Innate immune response of human plasmacytoid dendritic cells to poxvirus infection is subverted by vaccinia E3 via its Z-DNA/RNA binding domain," PLOS ONE, vol. 7, No. 5, p. e36823 (May 14, 2012).
Cao, H. et al.; Innate immune response of human plasmacytoid dendritic cells to poxvirus infection is subverted by vaccinia E3 via its Z-DNA/RNA binding domain. Plos One. 2012, vol. 7, No. 5, e36823, pp. 2 and Fig. 8.
Castle et al., "Exploiting the mutanome for tumor vaccination", Cancer Res., 72, pp. 1081-1091 (2012).
Chafekar, et al., "MERS-CoV: Understanding the Latest Human Coronavirus Threat," Viruses, 10, 93, 22 pages (Feb. 24, 2018).
Chavan et al., "Expression of CCL20 and granulocyte-macrophage colony-stimulating factor, but not Flt3-L, from modified vaccinia virus Ankara enhances antiviral cellular and humoral immune responses," J. Virology, vol. 80, No. 15, pp. 7676-7687 (2006).
Chi et al., "DNA vaccine encoding Middle East respiratory syndrome coronavirus S1 protein induces protective immune responses in mice," Vaccine, vol. 35, pp. 2069-2075 (Apr. 11, 2017).
Coffey et al., "Reovirus therapy of tumors with activated Ras pathway," Science, 282, pp. 1332-1334 (1998).
Curran et al, Tumor Vaccines Expressing Flt2 Ligand Synergize with CTLA-4 Blockade to Reject Preimplanted Tumors, Cancer Research vol. 69 No. 19, Sep. 8, 2009, pp. 7747-7755.
Dai et al., "Abstract B031: Heat-inactivated modified vaccinia virus Ankara induces type I IFN and antitumor immunity via the cytosolic DNA-sensing pathway," retrieved from: http://www.cancerimmunolrres.aacrjournals.org/content/4/1_Supplement/B031 (Jun. 15, 2018).
Dai et al., "Intratumoral delivery of inactivated modified vaccinia virus Ankara (iMVA) induces systemic antitumor immunity via STING and Batf3-dependent dendritic cells" Science Immunology, vol. 2, No. 11, pp. 1-34 (May 19, 2017).
Dai, P et al, Modified Vaccinia Virus Ankara Triggers Type 1 IFN Production in Murine Conventional Dendritic Cells via A cGAS/STING-Mediated Cytosolic DNA-Sensing Pathway, PLOS Pathogens, Apr. 2014, vol. 10, pp. 1-13.
Dai, P. et al, Myxoma Virus Induces Type 1 Interferon Production in Murine Plasmacytoid Dendritic Cells via a TLR9/MyD88-, IRF5/IRF7-, and IFNAR-Dependent Pathway. Journal of Virology, Oct. 2011, pp. 10814-10825.
Deng et al., "STING-Dependent Cytosolic DNA Sensing Promotes Radiation-Induced Type I Interferon-Dependent Antitumor Immunity in Immunogenic Tumors", Immunity, vol. 41, No. 5, pp. 843-852 (2014).
Deng et al., "Vaccinia virus infection attenuates innate immune responses and antigen presentation by epidermal dendritic cells", J Virol., 80, pp. 9977-9987 (2006).
Diamond et al., "Type I interferon is selectively required by dendritic cells for immune rejection of tumors", J Exp Med., vol. 208, No. 10, pp. 1989-2003 (2011).
Drexler et al., "Modified Vaccinia Virus Ankara for Delivery of Human Tyrosinase as Melanomaassociated Antigen: Induction of Tyrosinase- and Melanoma-specific Human Leukocyte Antigen A*0201-restricted Cytotoxic T Cells in Vitro and in Vivo1 ," Cancer Research, vol. 59, p. 4955-4963 (Oct. 1, 1999).
Drillien et al, Modified vaccination virus Ankara induces moderate activation of human dendritic cells, Journal of General Virology, Society for General Microbiology, vol. 85, No. Pt 8, Aug. 1, 2004, pp. 2167-2175.
Du et al., "The spike protein of SARS-CoV—a target for vaccine and therapeutic development," Microbiology, vol. 7, pp. 226-236 (Mar. 2009).
Engelmayer et al., "Vaccinia virus inhibits the maturation of human dendritic cells: a novel mechanism of immune evasion", J Immunol., 163, pp. 6762-6768 (1999).
Fishcer et al., "Modified vaccinia virus Ankara protein F1L is a novel BH3-domain-binding protein and acts together with the early viral protein E3L to block virus-associated apoptosis" Cell Death Differ., 13, pp. 109-118 (2006).
Fuertes et al., "Host type I IFN signals are required for antitumor CD8 T-cell responses through CD8{alpha} dendritic cells", J. Exp. Med., vol. 208, No. 10, 2005-2016 (2011).
Fuertes et al., "Type I interferon response and innate immune sensing of cancer," Trends Immunol., vol. 34, No. 2, pp. 67-73 (Feb. 2013).
Fung et al., "Human Coronavirus: Host-Pathogen Interaction," Annual Review of Microbiology, 73, pp. 529-557 (Jun. 21, 2019).
Gao et al., "Structure-function analysis of STING activation by c[G(2',5')pA(3',5')p] and targeting by antiviral DMXAA", Cell, 154, pp. 748-762 (2013).
Garcia et al., "Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02)", Vaccine, 29, pp. 8309-8316 (2011).
Garrido et al., "The escape of cancer from T lymphocytes: immunoselection of MHC class I loss variants harboring structural-irreversible "hard" lesions," Cancer Immunol. Immunother., 59, pp. 1601-1606 (2010).
GenBank: U94848.1 "Vaccinia virus strain Ankara, complete genomic sequence" p. 1-3 (Apr. 13, 2003).
Gerlini et al., "Metastatic melanoma secreted IL-10 down-regulates CD1 molecules on dendritic cells in metastatic tumor lesions", Am J Pathol., 165, pp. 1853-1863 (2004).
Gitlin et al., "Essential role of mda-5 in type I IFN responses to polyriboinosinic:polyribocytidylic acid and encephalomyocarditis picornavirus", Proc. Natl. Acad. Sci. U S A., vol. 103, No. 22, pp. 8459-8464 (May 30, 2006).
Goepfert et al., "Phase 1 safety and immunogenicity testing of DNA and recombinant modified vaccinia Ankara vaccines expressing HIV-1 virus-like particles", J Infect Dis., 203, pp. 610-619 (2011).
Gomez et al., "MVA and NYVAC as vaccines against emergent infectious diseases and cancer," Current Gene Therapy, vol. 11, No. 3, p. 189-217 (Jun. 2011).
Gomez et al., "The poxvirus vectors MVA and NYVAC as gene delivery systems for vaccination against infectious diseases and cancer", Curr Gene Ther., 8, pp. 97-120 (2008).
Greiner et al. "The highly attenuated vaccinia virus strain modified virus Ankara induces apoptosis in melanoma cells and allows bystander dendritic cells to generate a potent anti tumoral immunity" Clinical and Experimental Immunology vol. 146. No. 2, Nov. 1, 2006 pp. 344-353.
Guerra et al., "Distinct gene expression profiling after infection of immature human monocyte-derived dendritic cells by the attenuated poxvirus vectors MVA and NYVAC," J. of Virology, vol. 61, No. 16, pp. 8701-8721 (May 30, 2007).
Guerra et al., "Host-Range Restriction in Vaccinia Virus E3L Deletion Mutant Can Be Overcome In Vitro, but Not In Vivo, by Expression of the Influenza Virus NS1 Protein," PLoS ONE. vol. 6 No. 12, p. e28677 (2011).
Haagmans, et al., "An orthopoxvirus-based vaccine reduces virus excretions after MERS-CoV infection in dromedary camels," Science, vol. 351, pp. 77-81 (Jan. 1, 2016).
Hamid et al., "Safety and Tumor Responses with Lambrolizumab (Anti-PD-1) in Melanoma", The New England journal of medicine, vol. 369, No. 2, pp. 134-144 (2013).

(56) References Cited

OTHER PUBLICATIONS

Hammerich et al., In situ vaccination for the treatment of cancer, Immunotherapy vol. 8, No. 3, Mar. 1, 2016, pp. 315-330.
Harrop et al., "Vaccination of Colorectal Cancer Patients with Modified Vaccinia Ankara Delivering the Tumor Antigen 5T4 (TroVax) Induces Immune Responses which Correlate with Disease Control: A Phase I/II Trial," Clinical Cancer Research, vol. 12, No. 11 Pt. 1, p. 3416-6424 (Jun. 1, 2006).
Hodge et al., "Modified Vaccinia Virus Ankara Recombinants Are as Potent as Vaccinia Recombinants in Diversified Prime and Boost Vaccine Regimens to Elicit Therapeutic Antitumor Responses," American Association for Cancer Research, vol. 63, No. 22, p. 7942-7949 (Nov. 15, 2003).
Hodi et al., "Improved survival with ipilimumab in patients with metastatic melanoma", The New England journal of medicine, 363, pp. 711-723 (2010).
Holshue et al., "First Case of 2019 Novel Coronavirus in the United States," New England Journal of Medicine, 9 pages (Jan. 31, 2020).
Hornemann et al., "Replication of Modified Vaccinia Virus Ankara in Primary Chicken Embryo Fibroblasts Requires Expression of the Interferon Resistance Gene E3L," Journal of Virology, vol. 77, No. 15, p. 8394-8407 (Aug. 2003).
Huber et al., "Regulation of effector and memory T-cell functions by type I interferon", Immunology, 132, pp. 466-474 (2011).
Inman, "Immunotherapy/Targeted Therapy Combinations Show Promise in BRAF-Mutated Melanoma," Targeted Oncology, retrieved from: https://www.targetedonc.com/conference/smr-esmo-melanoma/immunotherapytargeted-therapy-combinations-show-promise-in-brafmutated-melanoma (Oct. 20, 2017).
International Search Report and Written Opinion on PCT/US2016/028184, dated Sep. 9, 2016, 17 pages.
International Search Report and Written Opinion on PCT/US2017/019548, dated Aug. 8, 2017, 17 pages.
International Search Report and Written Opinion on PCT/US2017/019549, dated Aug. 14, 2017, 17 pages.
International Search Report and Written Opinion on PCT/US2018/032451, dated Aug. 23, 2018, 16 pages.
International Search Report and Written Opinion on PCT/US2018/059476, dated Feb. 14, 2019, 9 pages.
International Search Report and Written Opinion, PCT/US2019/021853, Memorial Sloan Kettering Cancer Center (dated Jul. 16, 2019).
International Search Report and Written Opinion, PCT/US2019/051343 (dated Feb. 7, 2020).
Ishikawa et al., "STING is an endoplasmic reticulum adaptor that facilitates innate immune signaling", Nature, 455, pp. 674-678 (2008).
Jacobs et al., Vaccinia virus vaccines: Past, present and future, Antiviral Research, Elsevier BV, NL vol. 84, No. 1, Oct. 1, 2009 pp. 1-13.
Jenne et al., "Poxvirus as a vector to transduce human dendritic cells for immunotherapy: abortive infection but reduced APC function", Gene therapy, 7, pp. 1575-1583 (2000).
Jochems et al., "Tumor-infiltrating immune cells and prognosis: the potential link between conventional cancer therapy and immunity", Exp Biol Med.(Maywood), 236, pp. 567-579 (2011).
Kibler et al., "Double-stranded RNA is a trigger for apoptosis in vaccinia virus-infected cells", J. Virol., vol. 71, No. 3, pp. 1992-2003 (1997).
Kirn et al., "Replication-selective virotherapy for cancer: Biological principles, risk management and future directions," Nat. Med., 7, pp. 781-787 (2001).
Kirn et al., "Targeted and armed oncolytic poxviruses: a novel multi-mechanistic therapeutic class for cancer," Nature Reviews—Cancer, 9, pp. 64-71 (2009).
Kirn et al., "Targeting of interferon-beta to produce a specific, multi-mechanistic oncolytic vaccinia virus", PLoS Med., vol. 4, No. 12, pp. 2001-2012 (2007).
Kuzu et al., "Current State of Animal (Mouse) Modeling in Melanoma Research," Cancer Growth and Metastasis, 8(S1):81-94 (2015).
Lacy et al., "Immunotherapy for Melanoma," Expert Rev. Dermatol., 7, pp. 51-68 (2012).
Langland et al., "Inhibition of PKR by vaccinia virus: role of the N- and C-terminal domains of E3L," Journal of Virology, vol. 324, No. 2, p. 419-429 (Jul. 1, 2004).
Leach et al., "Enhancement of antitumor immunity by CTLA-4 blockade," Science, 271, pp. 1734-1736 (1996).
Lee et al., "The interferon-induced double-stranded RNA-activated protein kinase induces apoptosis," Journal of Virology, vol. 199, No. 2, p. 491-496 (Mar. 1994).
Lee et al., "Effect of resveratrol on the metastasis of 4T1 mouse breast cancer cells in vitro and in vivo," Nutrition Res. and Practice, vol. 6, No. 4, pp. 294-300 (2012).
Li et al., "Angiotensin-converting enzyme 2 is a functional receptor for the SARS coronavirus," Nature, vol. 426, pp. 450-454 (Nov. 27, 2003).
Li et al., "Disruption of MHC class II-restricted antigen presentation by vaccinia virus," J. Immunol., 175, pp. 6481-6488 (2005).
Li et al., "Early Transmission Dynamics in Wuhan, China, of Novel Coronavirus—Infected Pneumonia," New England Journal of Medicine, 9 pages (Jan. 29, 2020).
Li et al., "Pivotal roles of cGAS-cGAMP signaling in antiviral defense and immune adjuvant effects", Science, 341, pp. 1390-1394 (2013).
Li et al., "Structure of SARS Coronavirus Spike Receptor-Binding Domain Complexed with Receptor," Science, vol. 309, pp. 1864-1868 (Sep. 16, 2005).
Liu et al., "Deletion of C7L and K1L genes leads to significantly decreased virulence of recombinant vaccinia cirus TianTian," PLoS One, vol. 8, No. 7:e68115, pp. 1-13 (Jul. 1, 2013).
Liu, "Cancer-killing virus plus PD-1 and MEK inhibitors make for a 3-pronged attack on melanoma," retrieved from: https://www.fiercebiotech.com/research/pd-1-mek-inhibitor-and-anti-cancer-virus-a-3-pronged-attack-melanoma, 2 pages (Dec. 12, 2018).
Ludwig et al., "Role of Viral Factor E3L in Modified Vaccinia Virus Ankara Infection of Human HeLa Cells: Regulation of the Virus Life Cycle and Identification of Differentially Expressed Host Genes," Journal of Virology, vol. 79, No. 4, p. 2584-2596 (Feb. 2005).
Mandl, SJ et al, Immunotherapy With MVA-BN-HER2 Induces HER-2-specific Th1 Immunity and Alters the Intratumoral Balance of Effector and Regulatory T cells. Cancer Immunol Immunother, 2012, vol. 61, pp. 19-29.
Mayr et al., English-language translation of Abstract of: "[The smallpox vaccination strain MVA: marker, genetic structure, experience gained with the parenteral vaccination and behavior in organisms with a debilitated defence mechanism (author's transl)]," Zentralbl Bakteriol, Orig. B, 167, pp. 375-390 (1978).
Mayr et al., English-language translation of Abstract of: "Passage history, properties, and applicability of the attenuated vaccinia virus strain MVA," Infection, 3, pp. 6-14 (1975).
Mcintyre et al., "Mouse models of colorectal cancer as preclinical models," Bioessays, 37(8), pp. 909-920 (Aug. 2015).
Mellman et al., "Cancer immunotherapy comes of age", Nature, 480, pp. 480-489 (2011).
Meng et al., "C7L Family of Poxvirus Host Range Genes Inhibits Antiviral Activities Induced by Type I Interferons and Interferon Regulatory Factor 1", J. Virol., vol. 86, No. 8, pp. 538-4547 (2012).
Meng et al., "Vaccinia Virus K1L and C7L Inhibit Antiviral Activities Induced by Type I Interferons," Journal of Virology, vol. 83, No. 20, p. 10627-10636 (Oct. 2009).
Meyer et al., "Mapping of deletions in the genome of the highly attenuated vaccinia virus MVA and their influence on virulence", J. Gen. Virol., 72 ( Pt 5), pp. 1031-1038 (1991).
Mlecnik et al., "Tumor immunosurveillance in human cancers", Cancer Metastasis Rev, 30, pp. 5-12 (2011).
Morales et al., Genome comparison of a nonpathogenic myoxma virus field strain with its ancestor, the virulent Lausanne strain, J. Virol, vol. 83, No. 5, pp. 2397-2403 Mar. 2009.
Moss, "Poxviridae: The viruses and their replication," In Fields Virology (Lippincott Williams & Wilkins), pp. 2905-2946 (2007).

(56) References Cited

OTHER PUBLICATIONS

Nagaria et al., "Combined targeting of RAF and MEK synergistically inhibits tumorigenesis in triple negative breast cancer model systems," Oncotarget, vol. 8, No. 46, pp. 80804-80819 (Aug. 24, 2017).
Nagorsen et al., "Transcriptional analysis of tumor-specific T-cell responses in cancer patients," Crit. Rev. Immunol., 22, pp. 449-462 (2002).
Nakayama et al., "In vitro comparison between mouse B16 and human melanoma cell lines of the expression of ICAM-1 induced by cytokines and/or hyperthermia," J. Dermatol., 24(6), pp. 351-360 (Jun. 1997).
Nemunaitis, J., "Oncolytic viruses,". Invest. New Drugs, 17, pp. 375-386 (1999).
Oble et al., "Focus on TILs: prognostic significance of tumor infiltrating lymphocytes in human melanoma", Cancer immunity, 9, pp. 1-20 (2009).
Pardoll, "The blockade of immune checkpoints in cancer immunotherapy," Nat. Rev. Cancer, 12(4), pp. 252-264 (Mar. 22, 2012).
Park et al., "Use of a targeted oncolytic poxvirus, JX-594, in patients with refractory primary or metastatic liver cancer: a phase I trial," Lancet Oncol., 9, pp. 533-542 (May 19, 2008).
Peggs et al., "Blockade of CTLA-4 on both effector and regulatory T-cell compartments contributes to the antitumor activity of anti-CTLA-4 antibodies", J Exp Med., 206, pp. 1717-1725 (2009).
Peihong et al., "Modified Vaccinia Virus Ankara Triggers Type I IFN Production in Murine Conventional Dendritic Cells via a cGAS/STING-Mediated Cytosolic DNA-Sensing Pathway," PLOS Pathogens, vol. 10, No. 4, p. e1003989 (Apr. 17, 2014).
Peihong, "P339 Intratumoral delivery of modified vaccinia virus Ankara expressing human Flt3L as cancer immunotherapy," 31st Annual Meeting and Associated Programs of the Society for Immunotherapy of Cancer, Pt. 2, p. 1-241 (2016).
Peiris, et al., "The Severe Acute Respiratory Syndrome," New England Journal of Medicine, vol. 349, pp. 2431-2441 (Dec. 18, 2003).
Perkus et al., "Vaccinia virus host genes," Virology, 179(1), pp. 276-286 (1990).
Pramanick et al., "Excipient selection in parenteral formulation development", Pharma Times, vol. 45, No. 3, pp. 65-77 (2013).
Raj et al., "Dipeptidyl peptidase 4 is a functional receptor for the emerging human coronavirus—EMC," Nature, vol. 495, 6 pages (Mar. 13, 2013).
Reddy et al., "Influences of BRAF Inhibitors on the Immune Microenvironment and the Rationale for Combined Molecular and Immune Targeted Therapy," Curr. Oncol. Rep., 18(7)15 pages (Jul. 2016).
Robert et al., "Ipilimumab plus dacarbazine for previously untreated metastatic melanoma", The New England journal of medicine, 364, pp. 2517-2526 (2011).
Sabbatino et al., "Antitumor activity of BRAF inhibitor and IFN combination in BRAF-mutant melanoma," J. Natl. Cancer Inst., 108(7), 11 pages (Feb. 5, 2016).
Sato et al., "Distinct and essential roles of transcription factors IRF-3 and IRF-7 in response to viruses for IFN-alpha/beta gene induction", Immunity, 13, pp. 539-548 (2000).
Sauer et al., "The N-ethyl-N-nitrosourea-induced Goldenticket mouse mutant reveals an essential function of Sting in the in vivo interferon response to Listeria monocytogenes and cyclic dinucleotides", Infection and immunity, vol. 79, No. 2, pp. 688-694 (2011).
Schaedler et al., "Sequential administration of a MVA-based MUC1 cancer vaccine and the TLR9 ligand Litenimod (Li28) improves local immune defense against tumors," Vaccine, vol. 35, No. 4, p. 577-585 (Jan. 23, 2017).
Schumacher et al., "Neoantigens in cancer immunotherapy", Science, 348, pp. 69-74 (2015).
Sharma et al., "The future of immune checkpoint therapy", Science, 348, pp. 56-61 (2015).
Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBio, vol. 6, No. 4, pp. 1-9 (2015).
Song, et al., "Middle East Respiratory Syndrome Coronavirus Spike Protein Delivered by Modified Vaccinia Virus Ankara Efficiently Induces Virus-Neutralizing Antibodies," Journal of Virology, vol. 87, pp. 11950-11954 (Nov. 2013).
Sun et al., "Cyclic GMP-AMP synthase is a cytosolic DNA sensor that activates the type I interferon pathway", Science, 339, pp. 786-791 (2013).
Sutter et al., "Vaccinia vectors as candidate vaccines: the development of modified vaccinia virus Ankara for antigen delivery," Current Drug Targets—Infectious Disorders 3, pp. 263-271 (2003).
Tagliamonte et al., "Antigen-specific vaccines for cancer treatment", Human vaccines & immunotherapeutics, 10, pp. 3332-3346 (2014).
Takaoka et al., "New aspects of IFN-alpha/beta signalling in immunity, oncogenesis and bone metabolism", Cancer Sci., vol. 94, No. 5, pp. 405-411 (2003).
Thorne et al., "Rational strain selection and engineering creates a broad-spectrum, systemically effective oncolytic poxvirus, JX-963", J Clin Invest., vol. 117, No. 11, pp. 3350-3358 (2007).
Topalian et al., "Immune checkpoint blockade: a common denominator approach to cancer therapy", Cancer Cell, vol. 27, No. 4, pp. 450-461 (2015).
Topalian et al., "Targeting the PD-1/B7-H1(PD-L1) pathway to activate anti-tumor immunity", Curr Opin Immunol., 24, pp. 207-212 (2012).
Tormo et al., "Targeted activation of innate immunity for therapeutic induction of autophagy and apoptosis in melanoma cells", Cancer Cell, vol. 16, No. 2, pp. 103-114 (2009).
Tumeh et al., "PD-1 blockade induces responses by inhibiting adaptive immune resistance", Nature, vol. 515, No. 7258, pp. 568-571 (2014).
Verardi et al., "A vaccinia virus renaissance: new vaccine and immunotherapeutic uses after smallpox eradication", Human vaccines & immunotherapeutics, 8, pp. 961-970 (2012).
Verheust et al., "Biosafety aspects of modified vaccinia virus Ankara (MVA)-based vectors used for gene therapy or vaccination," Vaccine, 30, pp. 2623-2632 (2012).
Vijaysri et al., "Vaccinia Viruses with Mutations in the E3L Gene as Potential Replication-Competent, Attenuated Vaccines: Intra-Nasal Vaccination," Vaccine, vol. 26, No. 5, p. 664-676 (Jan. 30, 2008).
Volz, et al., "Protective Efficacy of Recombinant Modified Vaccinia Virus Ankara Delivering Middle East Respiratory Syndrome Coronavirus Spike Glycoprotein," Journal of Virology, vol. 89, pp. 8651-8656 (Aug. 2015).
Waibler et al., "Modified Vaccinia Virus Ankara Induces Toll-Like Receptor-Independent Type I Interferon Responses," Journal of Virology, vol. 81, No. 22, p. 12101-12110 (Nov. 2007).
Wang et al., Abstracts-Adaptive Immunity and Vaccination 034, Recombinant replication competent attenuated vaccinia virus expressing human Flt3L for cancer immunotherapy, Journal of Investigative Dermatology vol. 136, No. 5 May 2016 p. S6.
Wang W. et al., Recombinant replication competent attenuated vaccinia virus expressing human Flt3L for cancer immunotherapy. Society for Investigative Dermatology (SID) Annual Meeting. May 14 2016, p. S6, vol. 136, No. 034.
Weaver et al., "The identification and characterization of a monoclonal antibody to the vaccinia virus E3 protein", Virus Res., 130, pp. 269-274 (2007).
Wing et al., "CTLA-4 control over Foxp3 regulatory T-cell function", Science, 322, pp. 271-275 (2008).
Wolchok et al., "Ipilimumab monotherapy in patients with pretreated advanced melanoma: a randomised, double-blind, multicentre, phase 2, dose-ranging study," Lancet Oncol., 11, pp. 155-164 (2010).
Wolchok et al., "Nivolumab plus ipilimumab in advanced melanoma", The New England journal of medicine, 369, pp. 122-133 (2013).

(56) References Cited

OTHER PUBLICATIONS

Woo et al., "STING-dependent cytosolic DNA sensing mediates innate immune recognition of immunogenic tumors", Immunity, vol. 41, No. 5, pp. 830-842 (2014).
Wu et al., "Cyclic GMP-AMP is an endogenous second messenger in innate immune signaling by cytosolic DNA", Science, 339, pp. 826-830 (2013).
Wyatt et al., "Enhanced cell surface expression, immunogenicity and genetic stability resulting from a spontaneous truncation of HIV Env expressed by a recombinant MVA", Virology, 372, pp. 260-272 (2008).
Yong, et al., "Recent Advances in the Vaccine Development Against Middle East Respiratory Syndrome-Coronavirus," Frontiers in Microbiology, vol. 10, 18 pages (Aug. 2, 2019).
Zaki, et al., "Isolation of a Novel Coronavirus from a Man with Pneumonia in Saudi Arabia," The New England Journal of Medicine, vol. 367, pp. 1814-1820 (Nov. 8, 2012).
Zamarin et al., "Localized oncolytic virotherapy overcomes systemic tumor resistance to immune checkpoint blockade immunotherapy", Science translational medicine, vol. 6, No. 226, pp. 1-12 (2014).
Zhang, et al., "A DNA vaccine induces SARS coronavirus neutralization and protective immunity in mice," Nature, vol. 428, pp. 561-564 (Apr. 2004).
Zhou, et al., "A pneumonia outbreak associated with a new coronavirus of probable bat origin," Nature, 23 pages (Feb. 3, 2020).
Zurkova K. et al., The expression of the soluble isoform of hFlt3 ligand by recombinant vaccinia virus enhances immunogenicity of the vector. Oncology Reports. May 1 2009, pp. 1335-1343, vol. 21, No. 5.

\* cited by examiner

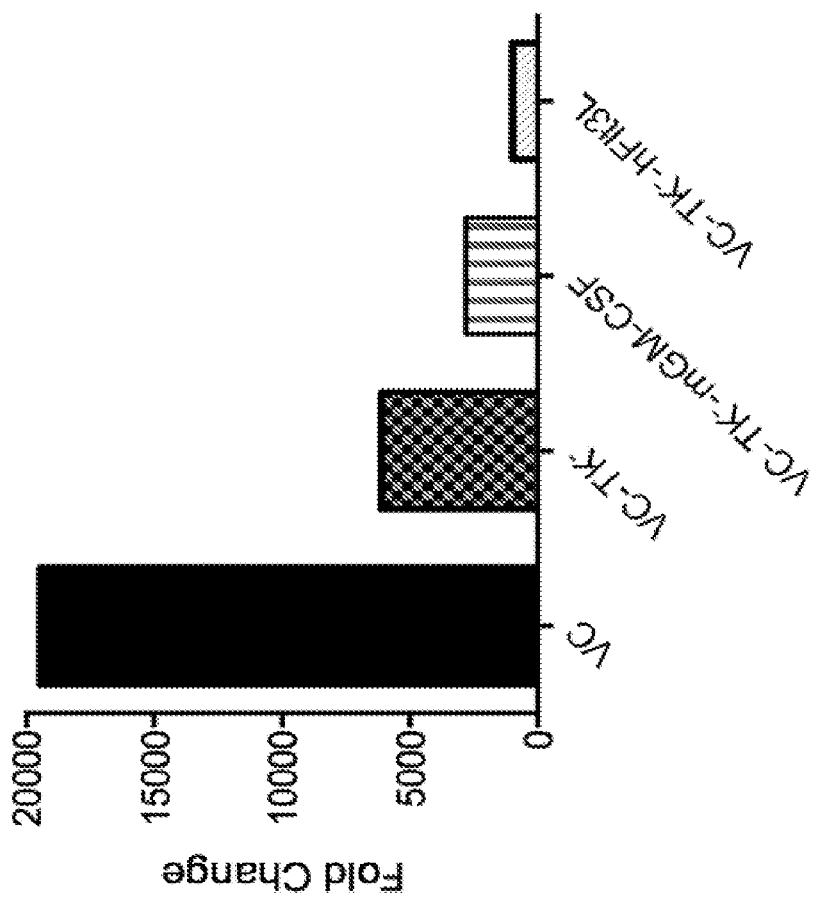
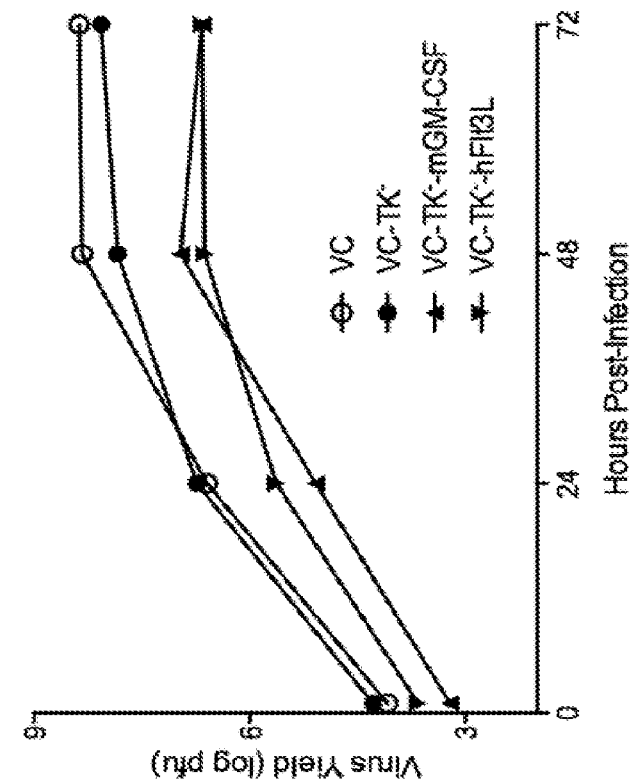
FIG. 5A
FIG. 5B

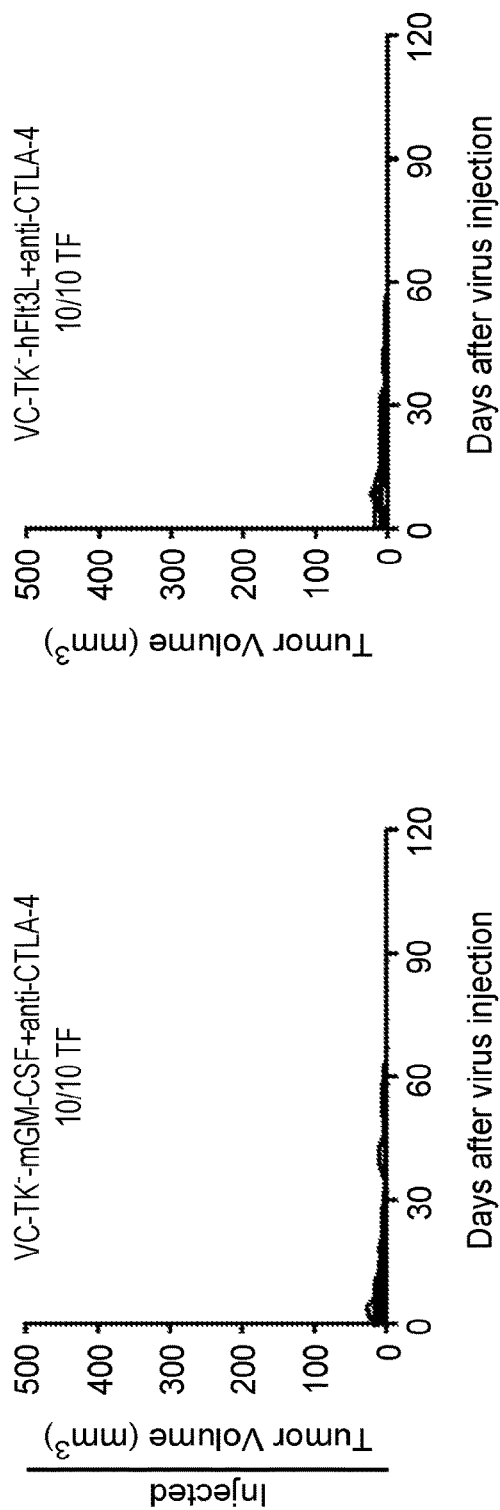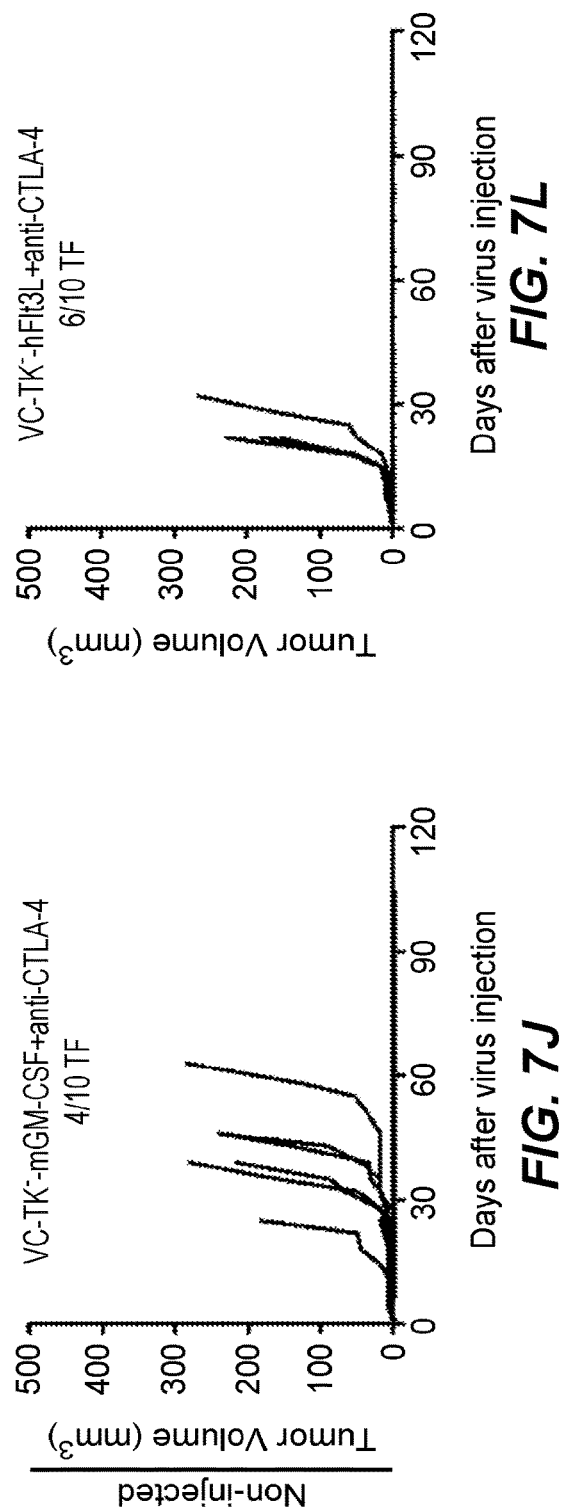

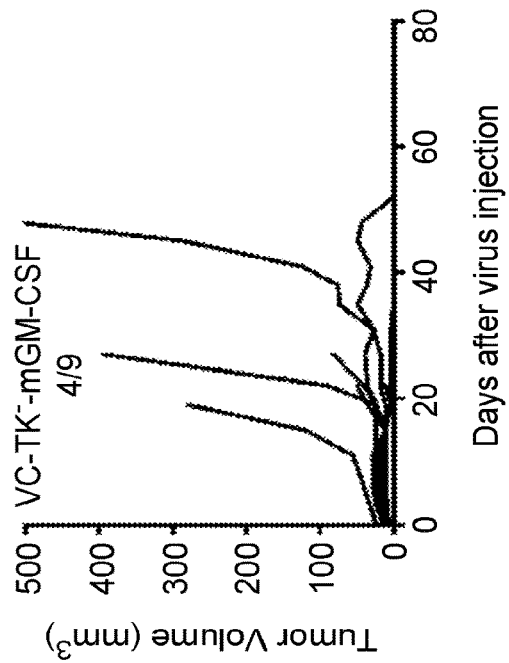
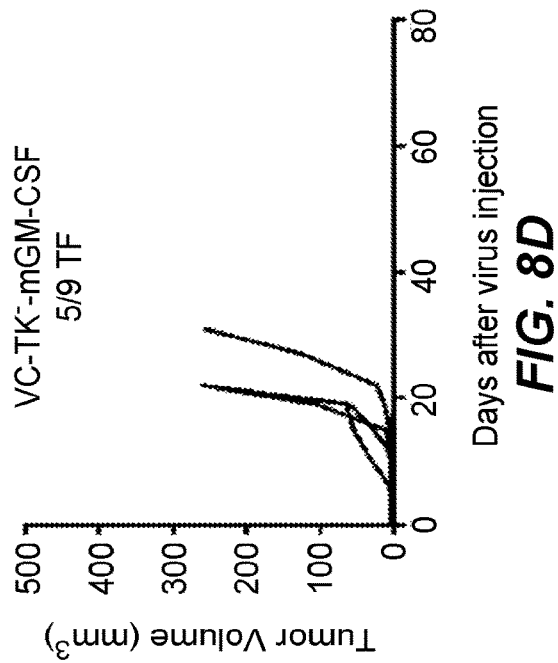
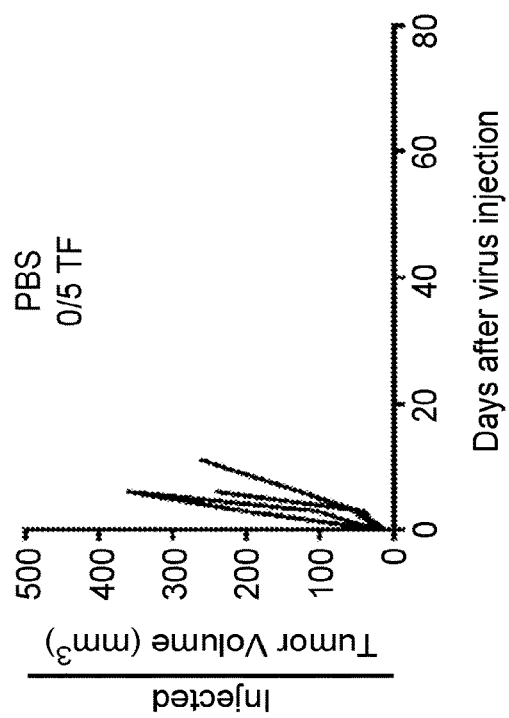
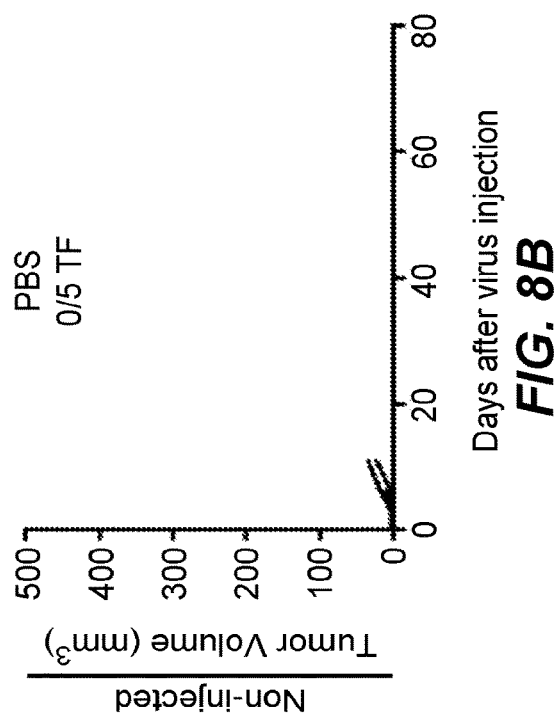

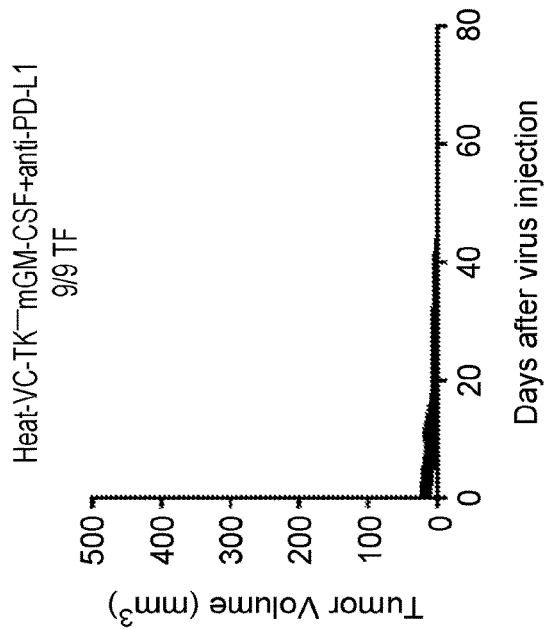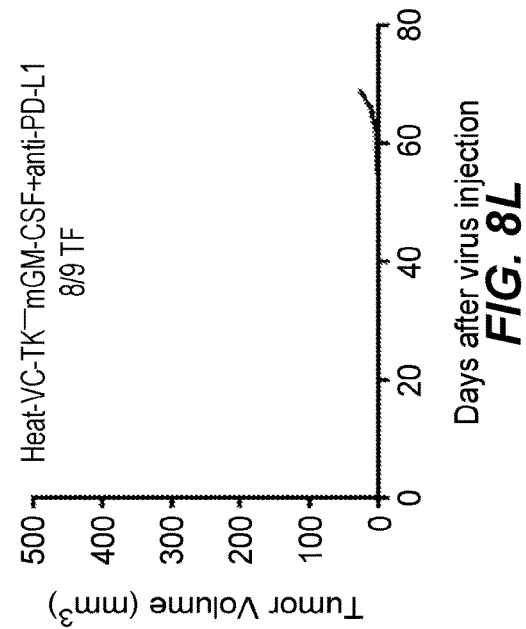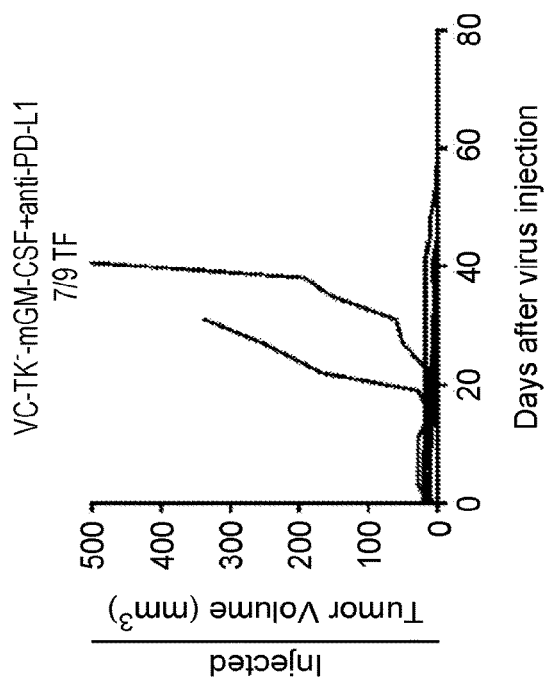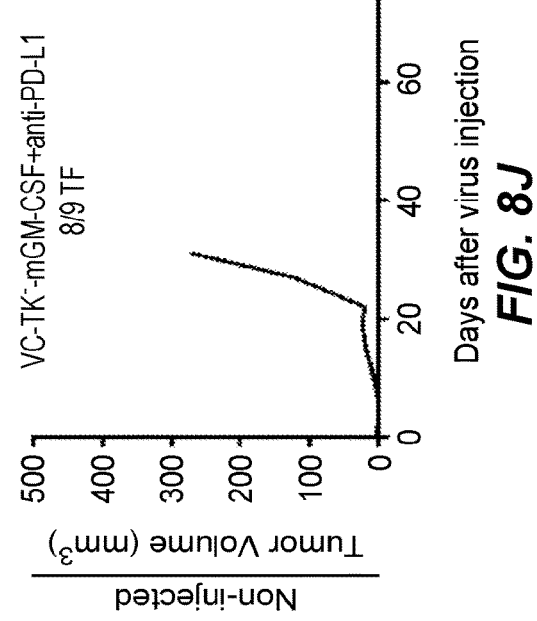

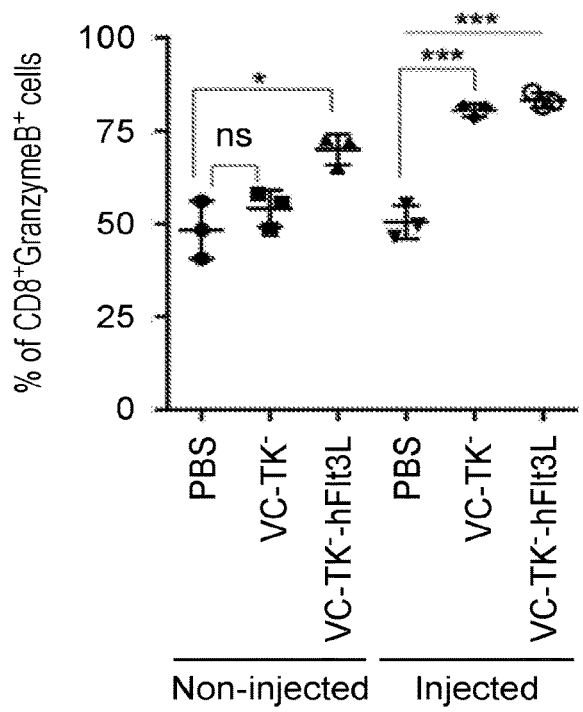
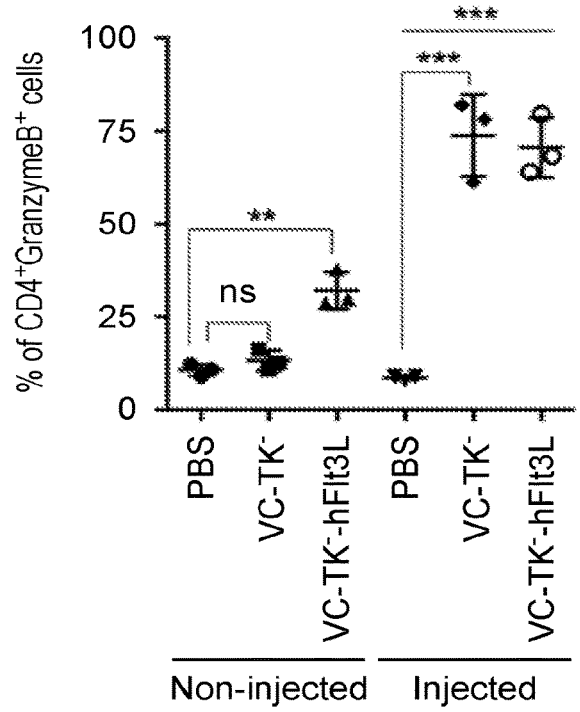
FIG. 10C
FIG. 10D

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtgaagacg ataaattaat gatc                                            24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgtcatcat gaacggcgga                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccttcgttt gccatacgct                                                 20
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaacgggact atggacgcat                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcggtttcct cacccaatcg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acctgatgga taaaaaggcg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcattgtgg tctacagcct                                              20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgtttcaca gtccgtttcc g                                            21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aacgacctat ctcctcctgc                                              20

<210> SEQ ID NO 10
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggctgaaag gcacatttgg                                              20
```

REPLICATION COMPETENT ATTENUATED VACCINIA VIRUSES WITH DELETION OF THYMIDINE KINASE WITH AND WITHOUT THE EXPRESSION OF HUMAN FLT3L OR GM-CSF FOR CANCER IMMUNOTHERAPY

RELATED APPLICATIONS

This application is a continuation of U.S. patent application Ser. No. 16/079,217, filed Aug. 23, 2018, which is a National Stage Application of PCT/US2017/019548, filed Feb. 25, 2017, which claims the benefit of and priority to U.S. Provisional Application Ser. No. 62/300,066, filed Feb. 25, 2016, the entire contents of each of which are incorporated herein by reference.

GOVERNMENT SUPPORT

The invention was made in part with government support under grants AI073736, AI095692, CA008748 and CA56821 awarded by the National Institutes of Health. The U.S. government has rights in this invention.

SEQUENCE LISTING

The instant application contains a Sequence Listing which has been submitted electronically in ASCII format and is hereby incorporated by reference in its entirety. Said ASCII copy, created on Feb. 23, 2017, is named 11000_005154-WO0_SL.txt and is 2,658 bytes in size.

FIELD OF THE INVENTION

The present invention relates generally to the fields of oncology, virology and immunotherapy. More particularly, it concerns the use of poxviruses, specifically the replication competent but attenuated vaccinia virus (1000 times attenuated compared to wild type vaccinia and therefore safe) with deletion of thymidine kinase (VC-TK$^-$) with and without the expression of human Flt3L or GM-CSF as oncolytic and immunotherapy. (VC-TK$^-$ is 1000 times less virulent compared to wild type vaccinia and therefore safe) The foregoing poxviruses can also be used in combination with immune checkpoint blocking agents. The foregoing poxviruses can also be inactivated via Heat or UV-treatment and the inactivated virus can be used as immunotherapy either alone or in combination with immune checkpoint blocking agents.

BACKGROUND

Immune System and Cancer

Malignant tumors are inherently resistant to conventional therapies and present significant therapeutic challenges. Immunotherapy has become an evolving area of research and an additional option for the treatment of certain types of cancers. The immunotherapy approach rests on the rationale that the immune system may be stimulated to identify tumor cells, and target them for destruction.

Numerous studies support the importance of the differential presence of immune system components in cancer progression (Jochems and Schlom, Exp Biol Med, 236(5): 567-579 (2011)). Clinical data suggest that high densities of tumor-infiltrating lymphocytes are linked to improved clinical outcome (Mlecnik et al., Cancer Metastasis Rev.; 30: 5-12, (2011)). The correlation between a robust lymphocyte infiltration and patient survival has been reported in various types of cancer, including melanoma, ovarian, head and neck, breast, urothelial, colorectal, lung, hepatocellular, gallbladder, and esophageal cancer (Angell and Galon, Current Opinion in Immunology, 25:1-7, (2013)). Tumor immune infiltrates include macrophages, dendritic cells (DC), mast cells, natural killer (NK) cells, naive and memory lymphocytes, B cells and effector T cells (T lymphocytes), primarily responsible for the recognition of antigens expressed by tumor cells and subsequent destruction of the tumor cells by T cells.

Despite presentation of antigens by cancer cells and the presence of immune cells that could potentially react against tumor cells, in many cases the immune system does not get activated or is affirmatively suppressed. Key to this phenomenon is the ability of tumors to protect themselves from immune response by coercing cells of the immune system to inhibit other cells of the immune system. Tumors develop a number of immunomodulatory mechanisms to evade antitumor immune responses. For example, tumor cells secrete immune inhibitory cytokines (such as TGF-β) or induce immune cells, such as CD4$^+$ T regulatory cells and macrophages, in tumor lesions to secrete these cytokines. Tumors have also the ability to bias CD4$^+$ T cells to express the regulatory phenotype. The overall result is impaired T-cell responses and induction of apoptosis or reduced anti-tumor immune capacity of CD8$^+$ cytotoxic T cells. Additionally, tumor-associated altered expression of MEW class I on the surface of tumor cells makes them 'invisible' to the immune response (Garrido et al. *Cancer Immunol. Immunother.* 59(10), 1601-1606 (2010). Inhibition of antigen-presenting functions and dendritic cell (DC) additionally contributes to the evasion of anti-tumor immunity (Gerlini et al. *Am. J. Pathol.* 165(6), 1853-1863 (2004).

Moreover, the local immunosuppressive nature of the tumor microenvironment, along with immune editing, can lead to the escape of cancer cell subpopulations that do not express the target antigens. Thus, finding an approach that would promote the preservation and/or restoration of antitumor activities of the immune system would be of considerable therapeutic benefit.

Immune checkpoints have been implicated in the tumor-mediated downregulation of anti-tumor immunity. It has been demonstrated that T cell dysfunction occurs concurrently with an induced expression of the inhibitory receptors, CTLA-4 and programmed death 1 polypeptide (PD-1), members of the CD28 family receptors. Nevertheless, despite extensive research in recent years, the success of immunotherapy in a clinical setting has been limited. Few therapeutic agents have been approved by regulatory authorities, and among those, the benefit has been observed only in a minority of patients. In recent years, immune checkpoints have been implicated in the downregulation of anti-tumor immunity and used as therapeutic targets. Studies have shown that T cell dysfunction occurs concurrently with an induced expression of the inhibitory receptor, programmed death 1 polypeptide (PD-1). PD-1 is an inhibitory member of the CD28 family of receptors that in addition to PD-1 includes without limitation CD28, CTLA-4, ICOS and BTLA. However, to date, these approaches have met with limited success. While promise regarding the use of immunotherapy in the treatment of melanoma has been underscored by the clinical use and even regulatory approval of anti-CTLA-4 (ipilimumab) and anti-PD-1 drugs (pembrolizumab and nivolumab) the response of patients to these immunotherapies has been limited. Recent clinical trials, focused on blocking these inhibitory signals in T cells (e.g., CTLA-4, PD-1, and the ligand of PD-1 PD-L1), have shown that reversing T cell suppression is critical for successful immunotherapy (Sharma and Allison, *Science* 348(6230), 56-61 (2015); Topalian et al., Curr Opin Immunol. 24(2), 202-217 (2012)). These observations highlight the need for development of novel therapeutic approaches for harnessing the immune system against cancer.

Melanoma

Melanoma, one of the most deadly cancers, is the fastest growing cancer in the US and worldwide. Its incidence has increased by 50% among young Caucasian women since 1980, primarily due to excess sun exposure and the use of tanning beds. According to the American Cancer Society, approximately 76,380 people in the US will be diagnosed with melanoma and 10,130 people (or one person per hour) are expected to die of melanoma in 2016. In most cases, advanced melanoma is resistant to conventional therapies, including chemotherapy and radiation. As a result, people with metastatic melanoma have a very poor prognosis, with a life expectancy of only 6 to 10 months. The discovery that about 50% of melanomas have mutations in BRAF (a key tumor-promoting gene) opened the door for targeted therapy in this disease. Early clinical trials with BRAF inhibitors showed remarkable, but unfortunately not sustainable, responses in patients with melanomas with BRAF mutations. Therefore, alternative treatment strategies for these patients, as well as others with melanoma without BRAF mutations, are urgently needed.

Human pathological data indicate that the presence of T-cell infiltrates within melanoma lesions correlates positively with longer patient survival (Oble et al. *Cancer Immun.* 9, 3 (2009)). The importance of the immune system in protection against melanoma is further supported by partial success of immunotherapies, such as the immune activators IFN-α2b and IL-2 (Lacy et al. *Expert Rev Dermatol* 7(1):51-68 (2012)) as well as the unprecedented clinical responses of patients with metastatic melanoma to immune checkpoint therapy, including anti-CTLA-4 and anti-PD-1/PD-L1 either agent alone or in combination therapy (Sharma and Allison, Science 348(6230), 56-61 (2015); Hodi et al., NEJM 363(8), 711-723 (2010); Wolchok et al., Lancet Oncol. 11(6), 155-164 (2010); Topalian et al., NEJM 366(26), 2443-2454 (2012); Wolchok et al., NEJM 369(2), 122-133 (2013); Hamid et al., NEJM 369(2), 134-144 (2013); Tumeh et al., Nature 515(7528), 568-571 (2014). However, many patients fail to respond to immune checkpoint blockade therapy alone. The addition of virotherapy might overcome resistance to immune checkpoint blocking agents, which is supported by animal tumor models (Zamarin et al., Sci Transl Med 6(226), 2014).

Poxviruses

Poxviruses, such as engineered vaccinia viruses, are in the forefront as oncolytic therapy for metastatic cancers (Kim et al., 2009). Vaccinia viruses are large DNA viruses, which have a rapid life cycle (Moss et al., 2007). Poxviruses are well suited as vectors to express multiple transgenes in cancer cells and thus to enhance therapeutic efficacy (Breitbach et al., 2012). Preclinical studies and clinical trials have demonstrated efficacy of using oncolytic vaccinia viruses and other poxviruses for treatment of advanced cancers refractory to conventional therapy (Park et al., 2008; Kim et al., 2007; Thorne et al., 2007). Poxvirus-based oncolytic therapy has the advantage of killing cancer cells through the combination of cell lysis, apoptosis, and necrosis. It also triggers innate immune sensing pathway that facilitates the recruitment of immune cells to the tumors and the development of anti-tumor adaptive immune responses. The current oncolytic vaccinia strains in clinical trials (JX-594, for example) use wild-type vaccinia with deletion of thymidine kinase to enhance tumor selectivity, and with expression of transgenes such as granulocyte macrophage colony stimulating factor (GM-CSF) to stimulate immune responses (Breitbach et al., 2012, Curr Pharm Biotechnol). Many studies have shown however that wild-type vaccinia has immune suppressive effects on antigen presenting cells (APCs) (Engelmayer et al., 1999; Jenne et al., 2000; Deng et al., 2006; Li et al., 2005; ref from Deng et al., J VI 2006 paper) and thus adds to the immunosuppressive and immunoevasive effects of tumors themselves.

Poxviruses however are extraordinarily adept at evading and antagonizing multiple innate immune signaling pathways by encoding proteins that interdict the extracellular and intracellular components of those pathways (Seet et al. Annu. Rev. Immunol. 21377-423 (2003)). Chief among the poxvirus antagonists of intracellular innate immune signaling is the vaccinia virus duel Z-DNA and dsRNA-binding protein E3, which can inhibit the PKR and NF-κB pathways (Cheng et al. Proc. Natl. Acad. Sci. USA 894825-4829 (1992); Deng et al. J. Virol. 809977-9987 (2006)) that would otherwise be activated by vaccinia virus infection. A mutant vaccinia virus lacking the E3L gene (ΔE3L) has a restricted host range, is highly sensitive to IFN, and has greatly reduced virulence in animal models of lethal poxvirus infection (Beattie et al. Virus Genes. 1289-94 (1996); Brandt et al. Virology 333263-270 (2004)). Recent studies have shown that infection of cultured cell lines with ΔE3L virus elicits proinflammatory responses that are masked during infection with wild-type vaccinia virus (Deng et al. J. Virol. 809977-9987 (2006); Langland et al. J. Virol. 8010083-10095). The inventors have reported that infection of a mouse epidermal dendritic cell line with wild-type vaccinia virus attenuated proinflammatory responses to the TLR agonists lipopolysaccharide (LPS) and poly(I:C), an effect that was diminished by deletion of E3L. Moreover, infection of the dendritic cells with ΔE3L virus triggered NF-κB activation in the absence of exogenous agonists (Deng et al. J. Virol. 809977-9987 (2006)). The inventors of the present disclosure have also showed that whereas wild-type vaccinia virus infection of murine keratinocytes does not induce the production of proinflammatory cytokines and chemokines, infection with ΔE3L virus does induce the production of IFN-β, IL-6, CCL4 and CCL5 from murine keratinocytes, which is dependent on the cytosolic dsRNA-sensing pathway mediated by the mitochondrial antiviral signaling protein (MAVS; an adaptor for the cytosolic RNA sensors RIG-I and MDA5) and the transcription factor IRF3 (Deng et al., J Virol. 2008 November; 82(21): 10735-10746.). See also international Application PCT/US2016/019663 filed by the inventor and co-workers on Feb. 25, 2016; and provisional application No. 62/149,484 filed on Apr. 17, 2015 and its corresponding international application, PCT/US2016/028184. These applications are herein incorporated by reference in their entirety.

E3LΔ83N virus with deletion of the Z-DNA-binding domain is 1,000-fold more attenuated than wild-type vaccinia virus in an intranasal infection model (Brandt et al., 2001). E3LΔ83N also has reduced neurovirulence compared with wild-type vaccinia in an intra-cranial inoculation model (Brandt et al., 2005). A mutation within the Z-DNA binding domain of E3 (Y48A) resulting in decreased Z-DNA-binding leads to decreased neurovirulence (Kim et al., 2003). Although the N-terminal Z-DNA binding domain of E3 is important in viral pathogenesis, how it affects host innate immune sensing of vaccinia virus is not well understood. The inventors have previously shown that myxoma virus but not wild-type vaccinia infection of murine plasmacytoid dendritic cells induces type I IFN production via the TLR9/MyD88/IRF5/IRF7-dependent pathway (Dai et al., 2011). Myxoma virus E3 ortholog M029 retains the dsRNA-binding domain of E3 but lacks the Z-DNA binding domain of E3. It was found that the Z-DNA-binding domain of E3 (but probably not Z-DNA-binding activity per se) plays an important role in inhibiting poxviral sensing in murine and human pDCs (Dai et al., 2011; Cao et al., 2012).

Deletion of E3L sensitizes vaccinia virus replication to IFN inhibition in permissive RK13 cells and results in a host range phenotype, whereby ΔE3L cannot replicate in HeLa or BSC40 cells (Chang et al., 1995). The C-terminal dsRNA-binding domain of E3 is responsible for the host range effects, whereas E3LΔ83N virus with deletion of the N-terminal Z-DNA-binding domain is replication competent in HeLa and BSC40 cells (Brandt et al., 2001). Because E3LΔ83N is 1000-fold more attenuated than wild-type vaccinia, in this application, the inventors explored its use as an attenuated replication competent vaccinia viral vector for further construction of immune-stimulating immunotherapeutic agent against various cancers.

Vaccinia virus (Western Reserve strain; WR) with deletion of thymidine kinase is highly attenuated in non-dividing cells but is replicative in transformed cells (Buller et al., 1988). TK-deleted vaccinia virus selectively replicates in tumor cells in vivo (Puhlmann et al., 2000). Thorne et al. showed that compared with other vaccinia strains, WR strain has the highest burst ratio in tumor cell lines relative to normal cells (Thorne et al., 2007). The inventors selected a derivative of this strain, vaccinia E3LΔ83N WR strain as their vector for further modification.

Human Flt3L (Fms-like tyrosine kinase 3 ligand), a type I transmembrane protein that stimulates the proliferation of bone marrow cells, was cloned for in 1994 (Lyman et al., 1994). The use of hFlt3L has been explored in various preclinical and clinical settings including stem cell mobilization in preparation for bone marrow transplantation, cancer immunotherapy such as expansion of dendritic cells, as well as an vaccine adjuvant. Recombinant human Flt3L (rhuFlt3L) has been tested in more than 500 human subjects and is bioactive, safe, and well tolerated (Fong et al., 1998; Maraskovsky et al., 2000; Shackleton et al., 2004; He et al., 2014; Anandasabapathy et al., 2015). Much progress has been recently made in the understanding of the critical role of the growth factor Flt3L in the development of DC subsets, including CD8α$^+$/CD103$^+$ DCs and pDCs (McKenna et al., 2000; Waskow et al., 2008; Liu et al., 2007; 2009; Naik et al., 2006; Ginhoux et al., 2009).

SUMMARY OF THE DISCLOSURE

In the present disclosure, the inventors generated recombinant E3LΔ83N-TK$^-$ virus and also built a construct of the same virus expressing human Flt3L, with the goal of delivering this growth factor to the tumor microenvironment to facilitate recruitment, differentiation and function of immune cells, including CD103$^+$/CD8α dendritic cells (DCs). A similar goal was pursued with E3LΔ83N-TK$^-$ expressing GM-CSF. However, experiments were also conducted with "naked" E3LΔ83N-TK$^-$ and with inactivated (specifically heat-inactivated) virus and viral constructs with favorable results, especially when administered in conjunction with checkpoint blockade inhibition therapy.

The present disclosure concerns methods and compositions for the treatment of solid tumors using a replication competent attenuated vaccinia virus either alone or in combination with immune checkpoint blocking agents. In some embodiments, methods and compositions involve deletion of Z-DNA-binding domain of E3Land thymidine kinase (TK) gene from wild-type vaccinia (Western Reserve strain, WR) and the expression of GM-CSF or Flt3L under vaccinia promoter.

This invention relates to the discovery that E3LΔ83N-TK$^-$ is attenuated in vitro and in vivo, and therefore it is a safer oncolytic virus compared with vaccinia comprising only TK deletion. Recombinant E3LΔ83N-TK- viruses expressing either GM-CSF or Flt3L may have an added benefit of immune stimulation. Infection by these viruses induces cancer cell death, which leads to tumor antigen release. Intratumoral injection of E3LΔ83N-TK$^-$ (VC-TK$^-$), E3LΔ83N-TK$^-$-mGM-CSF (VC-TK$^-$-mGM-CSF), E3LΔ83N-TK$^-$-hFlt3L(VC-TK$^-$-hFlt3L) leads to tumor regression and eradication of the injected tumor, and to the generation of antitumoral immunity. In addition, the combination of intratumoral delivery of either E3LΔ83N-TK$^-$-mGM-CSF or E3LΔ83N-TK$^-$-hFlt3L with immune checkpoint blocking agent dramatically improved survival (both number survived and duration) compared with virotherapy alone. Finally, intratumoral delivery of inactivated E3LΔ83N-TK$^-$-mGM-CSF after heating the virus at 55° C. (Heat-VC-TK$^-$-mGM-CSF) leads to more efficient tumor eradication at the contralateral non-injected site than the live virus. It is possible that alternating intratumoral delivery of the live virus with the inactivated virus might achieve better efficacies than either agent alone.

Therefore, E3LΔ83N-TK$^-$, E3LΔ83N-TK$^-$-GM-CSF, E3LΔ83N-TK$^-$-hFlt3L viruses, replicative or inactivated, can be used as oncolytic therapy and immunotherapy for the treatment of solid tumors. (It is understood that human GM-CSF would be used in viral constructs for human use. Results in mice with mouse GM-CSF are relevant to the human application of the present substances and compositions as the animal models used herein are well-accepted.) Additionally, the inventors of the present disclosure have shown that the combination of intratumoral delivery of oncolytic virus with immune checkpoint blocking agent leads to more efficient tumor eradication and better survival than either agent alone.

The recombinant vaccinia viruses can be administered intratumorally, intravenously, intraperitoneally, or intracranially or via a combination of localized (e.g., intratumoral) injection and a systemic or in any event more diffuse injection. The localized (e.g., intratumoral) injection of viruses can be used for various stages of tumors. For early stage cancer, virotherapy can be used 2-3 weeks prior to surgical removal of the tumor. During that time frame, the host would have developed systemic anti-tumor adaptive immunity. For advanced cancer, virotherapy can be used in combination with other treatment modalities, including surgery, chemotherapy, targeted therapy, radiation, and immune checkpoint therapy, which will be detailed below.

The present inventors hypothesized that intratumoral injection of one or more of E3LΔ83N-TK$^-$, E3LΔ83N-TK$^-$-GM-CSF, and E3LΔ83N-TK$^-$-hFlt3L viruses would provide additional beneficial effects to a PD-1 or CTLA-4 targeting approach, through altering tumor immune suppressive environment via the activation of immune cells including dendritic cells and macrophages, as well as facilitating tumor antigen presentation. Indeed, it was observed that treatment with a combination of VC-TK$^-$-GM-CSF and a checkpoint blockade inhibitor leads to development of immunity against a subsequent challenge with heterologous tumor. Similar results were observed with heat-inactivated viral construct combined or, surprisingly, even when not combined with immune checkpoint blockade therapy.

In further studies, the antitumor immunity of the TK⁻ virus and to a greater extent the viral-hFlt3L construct was found to include activation of effector CD8⁺ and CD4⁺ T cells (with the construct being more effective), leading to the expectation that similar results qualitatively would be observed after injection of viral GM-CSF construct. Further, the antitumor immunity of the viral-hFlt3L construct also led to an increase of CD103⁺ dendritic cells.

The foregoing antitumor results are not limited to melanoma but extend to other solid tumors such as breast cancer and colon carcinoma. Interestingly, certain viruses are more effective in one type of cancer and other viruses are more effective in another. Thus the use of the present therapies is subject to optimization. However, this does not detract from the utility of the present therapies, all the more because in cancer response to most therapeutic modalities is subject to case-by-case variability depending on differences in disease, the presence or absence of tumor infiltrating immune cells, in genetic and epigenetic factors, and in the use or nonuse of prior therapies. Furthermore, GM-CSF and FLt3L viral constructs have shown, or in light of the aforedescribed studies, are expected to show efficacy against established tumor models, which model advanced stage tumors.

In one aspect, the disclosure is directed to methods for treating a solid malignant tumor in a subject comprising delivering to tumor cells of the subject an amount of one or more of E3LΔ83N-TK⁻, E3LΔ83N-TK⁻-GM-CSF, and E3LΔ83N-TK⁻-hFlt3L viruses and viral constructs, including replicative (live) and inactivated versions thereof, effective to induce the immune system of the subject to mount an immune response against the tumor, for example as set forth above in this Summary so as to accomplish one or more of the following (regardless of order): reduce the size of the tumor, eradicate the tumor, inhibit growth of the tumor, or inhibit metastasis or metastatic growth of the tumor and thereby treat the tumor.

In another aspect, the disclosure is directed to an active substance selected from the group consisting of E3LΔ83N-TK⁻, E3LΔ83N-TK⁻-GM-CSF, and E3LΔ83N-TK⁻-hFlt3L, in replicative or inactivated form. These substances are each useful as sole active ingredients or in combination with two or more of them and optionally in combination with other therapeutic modalities, in an amount or in amounts effective to treat a solid malignant tumor or to elicit in the treated subject an immune response against the tumor, upon local administration to the tumor. The immune response may include one or more of the following immunological effects
  oncolysis of tumor cells and release of tumor antigen;
  an increase in cytotoxic CD8⁺ T cells within the tumor and/or in tumor-draining lymph nodes;
  induction of maturation of dendritic cells infiltrating said tumor or circulating in remote locations within the patient's body through induction of type I IFN;
  induction of effector CD4⁺ T cells in the subject recognizing tumor cells within the tumor and/or in tumor draining lymph nodes;

In a related aspect, the disclosure is directed to compositions comprising an effective amount for treating a solid malignant tumor or for eliciting in a patient an immune response against the tumor an active ingredient comprising one or more of E3LΔ83N-TK⁻, E3LΔ83N-TK⁻-GM-CSF, and E3LΔ83N-TK⁻-hFlt3L viruses and viral constructs, including replicative and inactivated versions thereof and a pharmaceutically acceptable excipient.

In another aspect, the disclosure is directed to a method for treating a malignant tumor comprising:
  delivering to tumor cells of the subject an amount of live or inactivated one or more of E3LΔ83N-TK⁻, E3LΔ83N-TK⁻-GM-CSF, and E3LΔ83N-TK⁻-hFlt3L viruses effective to induce the immune system of the subject to mount an immune response against the tumor.

In some embodiments one or more of the following specific features are also present:
  the recruitment and activation of effector CD4⁺ and CD8⁺ T cells is accompanied;
  the tumor is melanoma or colon carcinoma or breast carcinoma;
  a regimen of periodic delivery of one or more of E3LΔ83N-TK⁻, E3LΔ83N-TK⁻-GM-CSF, and E3LΔ83N-TK⁻-hFlt3L viruses is continued until it induces tumor regression or eradication;
  a regimen of periodic delivery of one or more of E3LΔ83N-TK⁻, E3LΔ83N-TK⁻-GM-CSF, and E3LΔ83N-TK⁻-hFlt3L viruses is continued for several weeks, months or years or indefinitely as long as benefits persist;
  a regimen of periodic delivery of one or more of E3LΔ83N-TK⁻, E3LΔ83N-TK⁻-GM-CSF, and E3LΔ83N-TK⁻-hFlt3L viruses is continued indefinitely until the maximum tolerated dose is reached;
  delivery of one or more of E3LΔ83N-TK⁻, E3LΔ83N-TK⁻-GM-CSF, and E3LΔ83N-TK⁻-hFlt3L viruses is by parenteral injection;
  delivery of one or more of E3LΔ83N-TK⁻, E3LΔ83N-TK⁻-GM-CSF, and E3LΔ83N-TK⁻-hFlt3L viruses is by intratumoral injection;
  delivery of the one or more of E3LΔ83N-TK⁻, E3LΔ83N-TK⁻-GM-CSF, and E3LΔ83N-TK⁻-hFlt3L viruses is by intravenous injection;
  the subject is a human;
  E3L≠83N-TK⁻, E3LΔ83N-TK⁻-GM-CSF, and/or E3LΔ83N-TK⁻-hFlt3L viruses is delivered at a dosage per administration within the range of about $10^5$-$10^{10}$ plaque-forming units (pfu);
  E3LΔ83N-TK⁻, E3LΔ83N-TK⁻-GM-CSF, and/or E3LΔ83N-TK⁻-hFlt3L viruses is delivered at a dosage per administration within the range of about $10^6$ to about $10^9$ plaque-forming units (pfu);
  the amount delivered is sufficient to infect all tumor cells;
  the delivery is repeated with a frequency within the range from once per month to two times per week;
  the treatment continues for a period of weeks, months or years;
  the delivery is repeated with a frequency within the range from once per month to two times per week;
  the melanoma is metastatic melanoma.

Delivery of E3LΔ83N-TK⁻, E3LΔ83N-TK⁻-GM-CSF, E3LΔ83N-TK⁻-hFlt3L viruses in the locale of the tumor induces the immune system of a subject afflicted with a malignant solid tumor to mount an immune response against the tumor. Stimulation of the subject's immune system against the tumor can be manifest (and may indeed be tested) by one or more of the following immunological effects
  oncolysis of tumor cells and release of tumor antigen;
  an increase in cytotoxic CD8⁺ T cells within the tumor and/or in tumor-draining lymph nodes;
  oncolysis and release of tumor antigens;
  induction of effector T cells in the subject recognizing tumor cells within the tumor and/or in tumor draining lymph nodes.

In certain embodiments, present invention relates to an isolated and purified active substance comprising E3LΔ83N-TK⁻-hFlt3L in replicative or inactivated form suitable for use as an immunotherapeutic agent against a malignant solid tumor.

In yet further aspects, the invention relates to a method for treating a subject afflicted with one or more solid malignant tumors, the method comprising delivering to cells of the tumor replication competent or inactivated E3LΔ83N-TK⁻-hFlt3L virus and thereby treating the tumor.

In certain embodiments, the amount is effective to accomplish one or more of the following:
a. induce the immune system of the subject to mount an immune response against the tumor;
b. reduce the size of the tumor;
c. eradicate the tumor;
d. inhibit growth of the tumor;
e. inhibit metastasis of the tumor; and
f. reduce or eradicate metastatic tumor.

In other embodiments, the tumor includes tumor located at the site of delivery, or tumor located both at said site and elsewhere in the body of the subject.

In yet further embodiments, the immune response comprises one or more of the following:
a. oncolysis of tumor cells and release of tumor antigen;
b. increase in cytotoxic CD8⁺ T cells within the tumor and/or in tumor-draining lymph nodes;
c. induction of maturation of dendritic cells infiltrating said tumor through induction of type I IFN;
d. induction of activated CD4⁺ effector T cells in the subject recognizing tumor cells within the tumor or systemically.

In additional embodiments, the tumor is primary or metastatic melanoma or breast carcinoma or colon carcinoma.

In yet additional aspects the invention relates to a method for treating a solid malignant tumor in a subject comprising delivering to tumor cells of the subject an amount of replication competent or inactivated E3LΔ83N-TK⁻-hFlt3L virus effective to induce the immune system of the subject to mount an immune response against the tumor.

In certain embodiments, the immune response is systemic.

In additional embodiments, the immune response effects or contributes to one or more of the following: reduction of the size of the tumor, eradication of the tumor, inhibition of tumor or metastatic growth.

In further embodiments, the virus is effective to accomplish one or more of the following:
a. induce the immune system of the subject to mount an immune response against the tumor;
g. b. reduce the size of the tumor;
h. c eradicate the tumor;
i. d. inhibit growth of the tumor;
j. e. inhibit metastasis of the tumor; and
reduce or eradicate metastatic tumor.

In yet additional aspects the invention relates to method for treating a malignant tumor in a subject, the method comprising delivering to tumor cells of the subject replication competent or inactivated E3LΔ83N-TK⁻-hFlt3L virus in an amount effective to induce the immune system of the subject to mount an immune response against the tumor and conjointly administering or having administered to the subject a second amount of an immune checkpoint blocking agent effective to block immune suppressive mechanisms within the tumor elicited by tumor cells, stromal cells, or tumor infiltrating immune cells.

In yet additional aspects the invention relates to a method for treating a malignant tumor in a subject, the method comprising delivering or having delivered to tumor cells of the subject replication competent or inactivated E3LΔ83N-TK--hFlt3L virus in an amount effective to induce the immune system of the subject to mount an immune response against the tumor and conjointly administering or having administered to the subject a second amount of an immune checkpoint blocking agent effective to block immune suppressive mechanisms within the tumor elicited by tumor cells, stromal cells, or tumor infiltrating immune cells.

In certain embodiments, the conjoint administration is effective to accomplish one or more of the following:
a. induce the immune system of the subject to mount an immune response against the tumor;
b. reduce the size of the tumor;
c. eradicate the tumor;
d. inhibit growth of the tumor;
e. inhibit metastasis of the tumor; and
f. reduce or eradicate metastatic tumor.

In yet additional aspects the tumor is primary or metastatic malignant melanoma or breast carcinoma or colon carcinoma. In yet additional aspects the virus is heat-inactivated.

In yet additional aspects the invention relates to a composition comprising an effective amount for treating a patient afflicted with a solid malignant tumor an active ingredient comprising E3LΔ83N-TK⁻-hFlt3L, in replicative or inactivated form, or both, and a pharmaceutically acceptable excipient.

In yet additional aspects the amount is effective to accomplish one or more of the following: reduce the size of the tumor, eradicate the tumor, inhibit growth of the tumor, or inhibit metastasis or metastatic growth of the tumor and thereby treat the tumor.

In yet additional aspects the amount is effective to elicit in the treated subject an immune response against the tumor and any metastases thereof, upon local delivery to tumor cells of the subject.

In yet additional aspects the immune response includes one or more of the following:
an increase in cytotoxic CD8⁺ T cells within the tumor and/or in tumor-draining lymph nodes;
induction of maturation of dendritic cells infiltrating said tumor or circulating in remote locations within the patient's body through induction of type I IFN;
induction of effector CD4⁺ T cells in the subject recognizing tumor cells within the tumor and/or in tumor draining lymph nodes.

In yet additional aspects the invention relates to an isolated purified active substance selected from the group consisting of E3LΔ83N-TK⁻, E3LΔ83N-TK⁻-GM-CSF, and E3LΔ83N-TK⁻-Flt3L, in replicative or inactivated form, suitable for use as a immunotherapeutic agent against a malignant solid tumor.

In yet additional aspects the invention relates to a composition comprising an effective amount for treating a patient afflicted with a solid malignant tumor of an active ingredient comprising one or more of E3LΔ83N-TK⁻, E3LΔ83N-TK⁻-GM-CSF, and E3LΔ83N-TK⁻-hFlt3L viruses and viral constructs, each optionally in replicative or inactivated form, and a pharmaceutically acceptable excipient.

In yet additional aspects the composition contains two or more of said viruses and viral constructs.

In yet additional aspects the amount is effective to accomplish one or more of the following: reduce the size of the tumor, eradicate the tumor, inhibit growth of the tumor, or inhibit metastasis or metastatic growth of the tumor and thereby treat the tumor.

In yet additional aspects the amount is effective to elicit in the treated subject an immune response against the tumor and other tumors in the treated subject's body, upon local delivery to tumor cells of the subject.

In yet additional aspects the immune response may include one or more of the following:
- an increase in cytotoxic $CD8^+$ T cells within the tumor and/or in tumor-draining lymph nodes;
- induction of maturation of dendritic cells infiltrating said tumor or circulating in remote locations within the patient's body through induction of type I IFN;
- induction of effector $CD4^+$ T cells in the subject recognizing tumor cells within the tumor and/or in tumor draining lymph nodes.

In yet additional aspects the invention relates to a method for treating a solid malignant tumor in a subject comprising delivering to tumor cells of the subject an amount of one or more of E3LΔ83N-TK$^-$, E3LΔ83N-TK$^-$-GM-CSF, and E3LΔ83N-TK$^-$-hFlt3L viruses and viral constructs, each optionally in replicative or inactivated form, effective to induce the immune system of the subject to mount an immune response against the tumor.

In yet additional aspects the invention relates to a method for treating a solid malignant tumor in a subject comprising delivering to tumor cells of the subject an amount of one or more of E3LΔ83N-TK$^-$, E3LΔ83N-TK$^-$-GM-CSF, and E3LΔ83N-TK$^-$-hFlt3L viruses and viral constructs, including replicative and inactivated versions of each of the foregoing, effective to accomplish one or more of the following (regardless of order):
a. induce the immune system of the subject to mount an immune response against the tumor;
b. reduce the size of the tumor;
c. eradicate the tumor;
d. inhibit growth of the tumor;
e. inhibit metastasis of the tumor; and
f. reduce or eradicate metastatic tumor.

In yet additional aspects the immune response may include one or more of the following immunological effects
- an increase in cytotoxic $CD8^+$ T cells within the tumor and/or in tumor-draining lymph nodes;
- induction of maturation of dendritic cells infiltrating said tumor or circulating in remote locations within the patient's body through induction of type I IFN;
- induction of effector T cells in the subject recognizing tumor cells within the tumor and/or in tumor draining lymph nodes.

In yet additional aspects the invention relates to a method for treating a malignant tumor in a subject, the method comprising delivering or having delivered to the subject tumor cells of the subject replication competent or inactivated E3LΔ83N-TK$^-$, E3LΔ83N-TK$^-$-GM-CSF, and E3LΔ83N-TK$^-$-hFlt3L viruses or viral constructs, each optionally in replicative or inactivated form, in an amount effective to induce the immune system of the subject to mount an immune response against the tumor and conjointly administering or having administered to the subject a second amount of an immune checkpoint blocking agent effective to block immune suppressive mechanisms within the tumor elicited by tumor cells, stromal cells, or tumor infiltrating immune cells.

In yet additional aspects the conjoint administration is effective to accomplish one or more of the following:

a) induce the immune system of the subject to mount an immune response against the tumor;
b) reduce the size of the tumor;
c) eradicate the tumor;
d) inhibit growth of the tumor;
e) inhibit metastasis of the tumor; and reduce or eradicate metastatic tumor.

In yet additional aspects the invention relates to a method for treating a malignant tumor in a subject, wherein the subject has been previously treated or dosed with replication competent or inactivated E3LΔ83N-TK$^-$, E3LΔ83N-TK$^-$-GM-CSF, and E3LΔ83N-TK$^-$-hFlt3L viruses or viral constructs, each optionally in replicative or inactivated form, in an amount effective to induce the immune system of the subject to mount an immune response against the tumor In yet additional embodiments, the method comprises delivering to the subject tumor cells of the subject an amount of an immune checkpoint blocking agent effective to block immune suppressive mechanisms within the tumor elicited by tumor cells, stromal cells, or tumor infiltrating immune cells.

In yet additional aspects the invention relates to a method for treating a malignant tumor in a subject, wherein the subject has been previously treated or dosed with an amount of an immune checkpoint blocking agent effective to block immune suppressive mechanisms within the tumor elicited by tumor cells, stromal cells, or tumor infiltrating immune cells In yet additional embodiments, the method comprises delivering or having delivered to the subject tumor cells of the subject replication competent or inactivated E3LΔ83N-TK$^-$, E3LΔ83N-TK$^-$-GM-CSF, and E3LΔ83N-TK$^-$-hFlt3L viruses or viral constructs, each optionally in replicative or inactivated form, in an amount effective to induce the immune system of the subject to mount an immune response against the tumor.

In yet additional aspects the immune checkpoint blocking agent comprises CTLA-4, CD80, CD86, PD-1, PDL1, PDL2, LAG3, B7-H3, B7-H4, TIM3, ICOS, II DLBCL inhibitors, BTLA, or any combination thereof.

In yet additional aspects the immune checkpoint blocking agent comprises ipilimumab, nivolumab, pembrolizumab, pidilizumab, AMP-224, MPDL3280A, BMS-936559, MEDI4736, MSB 00107180, or any combination thereof.

BRIEF DESCRIPTION OF THE DRAWINGS

FIG. 4A shows a Western blot analysis of mGM-CSF expression in VC-TK$^-$-mGM-CSF-infected murine B16 melanoma cells and human SK-MEL-28 melanoma cells. FIG. 4A shows data from B16-F10 and SK-MEL-28 cells that were infected or mock infected with VC-TK$^-$-mGM-CSF. Cell lysates and supernatants were collected at various times post infection. Western blot analyses were performed using anti-mGM-CSF antibody and anti-GAPDH as a loading control. FIG. 4B shows a Western blot analysis of hFlt3L expression in VC-TK$^-$-hFlt3L-infected murine and human melanoma cells. B16-F10, SK-MEL-146, and SK-MEL-28 cells were infected or mock infected with VC-TK$^-$-hFlt3L. Cell lysates were collected at various times post infection. Western blot analysis of cell lysates was performed using anti-hFlt3L antibody and anti-GAPDH as a control.

FIG. 5A-B shows a one-step growth of VC, VC-TK$^-$, VC-TK$^-$-mGM-CSF, and VC-TK$^-$-hFlt3L in B16-F10 melanoma cells. B16-F10 melanoma cells were infected with VC, VC-TK$^-$, VC-TK$^-$-mGM-CSF, or VC-TK$^-$-hFlt3L at a MOI of 0.1. Cells were collected at various times post infection and viral yields were determined by titrating on BSC40 cells. Viral yields (log pfu) were plotted against hours post infection in (FIG. 5A). The fold changes of viral yields at 72 h over those at 1 h post infection were plotted in (FIG. 5B).

FIG. 7A-L shows a series of graphical representations of intratumoral injection of VC-TK$^-$, VC-TK$^-$-mGM-CSF, or VC-TK$^-$-hFlt3L alone or in combination with intraperitoneal delivery of anti-CTLA-4 antibody in a B16-F10 melanoma bilateral implantation model. B16-F10 melanoma cells ($5 \times 10^5$) were implanted intradermally into the shaved skin on the right flank, and ($1 \times 10^5$) cells were implanted to the left flank. At 7 days post implantation, the right side tumors (about 3 mm in diameter) were injected twice weekly with either PBS, VC-TK$^-$, VC-TK$^-$-mGM-CSF, or VC-TK$^-$-hFlt3L ($2 \times 10^7$ pfu). Some groups of mice were treated with a combination of intratumoral delivery of either VC-TK$^-$-mGM-CSF, or VC-TK$^-$-hFlt3L ($2 \times 10^7$ pfu) and intraperitoneal delivery of anti-CTLA-4 antibody (100 µg/mouse) twice weekly. Tumor sizes were measured and mouse survival was monitored over time. (FIG. 7A, B) graphs of volume of injected tumors (FIG. 7A) and non-injected tumors (FIG. 7B) at various days post injection with PBS (n=10). (FIG. 7C, D) graphs of volume of injected tumors (FIG. 7C) and non-injected tumors (FIG. 7D) at various days post injection with VC-TK$^-$ (n=10). (FIG. 7E, F) graphs of volume of injected tumors (FIG. 7E) and non-injected tumors (FIG. 7F) at various days post injection with VC-TK$^-$-mGM-CSF (n=10). (FIG. 7G, H) graphs of volume of injected tumors (FIG. 7G) and non-injected tumors (FIG. 7H) at various days post injection with VC-TK$^-$-hFlt3L. (FIG. 7I, J) graphs of volume of injected tumors (FIG. 7I) and non-injected tumors (FIG. 7J) at various days post injection with VC-TK$^-$-mGM-CSF with intraperitoneal delivery of anti-CTLA-4 antibody (n=10). (FIG. 7K, L) graphs of volume of injected tumors (FIG. 7K) and non-injected tumors (FIG. 7L) at various days post injection with VC-TK$^-$-hFlt3L with intraperitoneal delivery of anti-CTLA-4 antibody.

FIG. 8A-O shows a series of graphical representations of intratumoral delivery of live VC-TK$^-$-mGM-CSF, Heat-inactivated VC-TK$^-$-mGM-CSF, live plus Heat-inactivated E3LΔ83N-TK$^-$-mGM-CSF with or without intraperitoneal delivery anti-PD-L1 antibody in a B16-F10 melanoma bilateral implantation model. B16-F10 melanoma cells were implanted bilaterally as described above in FIG. 6. At 7 days post implantation, the right side tumors (about 3 mm in diameter) were injected with either PBS, live VC-TK$^-$-mGM-CSF ($2 \times 10^7$ pfu), Heat-inactivated VC-TK$^-$-mGM-CSF (an equivalent of $2 \times 10^7$ pfu), live ($1 \times 10^7$ pfu) plus Heat-inactivated VC-TK$^-$-mGM-CSF (an equivalent of $1 \times 10^7$ pfu), with or without intraperitoneal delivery of anti-PD-L1 antibody (200 µg/mouse) twice weekly. Tumor size was measured and mouse survival was monitored over time. FIG. 8A-B are graphs showing the volume of injected tumors (FIG. 8A) and non-injected tumors (FIG. 8B) at various days post injection with PBS (n=5). FIGS. 8 C, D are graphs showing the volume of injected tumors (FIG. 8C) and non-injected tumors (FIG. 8D) at various days post injection with VC-TK$^-$-mGM-CSF (n=9). FIGS. 8 I, J are graphs showing the volume of injected tumors (FIG. 8I) and non-injected tumors (FIG. 8J) at various days post injection with VC-TK$^-$-mGM-CSF in the presence of systemic delivery of anti-PD-L1 antibody (n=9). FIG. 8K, L are graphs showing the volume of injected tumors (FIG. 8K) and non-injected tumors (FIG. 8L) at various days post injection with Heat-inactivated VC-TK$^-$-mGM-CSF in the presence of systemic delivery of anti-PD-L1 antibody (n=9). FIGS. 8 M, N are graphs showing the volume of injected tumors (FIG. 8M) and non-injected tumors (FIG. 8N) at various days post injection with live+ inactivated VC-TK$^-$-mGM-CSF in the presence of systemic delivery of anti-PD-L1 antibody (n=9). FIG. 8O is a Kaplan-Meier survival curve of mice treated with PBS, live VC-TK$^-$-mGM-CSF, Heat-inactivated VC-TK$^-$-mGM-CSF, live+Heat-inactivated VC-TK⁻-mGM-CSF, VC-TK⁻-mGM-CSF+anti-PD-L1, Heat-inactivated VC-TK⁻-mGM-CSF+anti-PD-L1, or live+Heat-inactivated VC-TK⁻-mGM-CSF+anti-PD-L1 antibody. Survival data were analyzed by log-rank (Mantel-Cox) test. *, P<0.05; ****, P<0.0001.

FIG. 10A-D is a series of graphical representations of data collected after intratumoral injection of VC-TK– or VC-TK⁻-hFlt3L which shows that VC-TK⁻-hFlt3L is more effective than VC-TK⁻ virus in activating both $CD8^+$ and $CD4^+$ T cells in both injected and non-injected tumors in a bilateral melanoma model. FIG. 10A consists of representative flow cytometry dot plots of $CD8^+$Granzyme $B^+$ cells in injected (right plot) and non-injected (left plot) tumors of mice treated variously with PBS, VC-TK⁻, or VC-TK⁻-hFlt3L. FIG. 10B consists of dot plots of $CD4^+$Granzyme $B^+$ cells in injected (right plot) and non-injected (left plot) tumors of mice treated variously with PBS, VC-TK⁻, or VC-TK⁻-hFlt3L. FIG. 10C consists of two plots of the percentage of $CD8^+$Granzyme $B^+$ cells in injected (right) and non-injected (left) tumors of mice treated variously with PBS, VC-TK⁻, or VC-TK⁻-hFlt3L. (*, p<0.05, *, p<0.001). Data are means±SEM (n=3). FIG. 10D consists of two plots of the percentage of $CD4^+$Granzyme $B^+$ cells in injected (right) and non-injected (left) tumors of mice treated variously with PBS, VC-TK⁻, or VC-TK⁻-hFlt3L. (, p<0.01, ***, p<0.001). Data are means±SEM (n=3).

FIG. 12A is a graph showing percentages of $CD103^+$ DCs out of CD45+ cells in both injected and non-injected tumors of mice treated with PBS, Heat-MVA, VC-TK–, VC-TK⁻-mGM-CSF, or VC-TK⁻hFlt3L (*, p<0.05). Data are means+/−SEM (n=3-4). FIG. 12B is a graph showing percentages of $CD11b^+$ DCs out of CD45+ cells in both injected and non-injected tumors (*, p<0.05). Data are means+/−SEM (n=3-4).

FIG. 13A-B are graphs of the initial respective tumor volumes (injected and non-injected) prior to the first injections. (FIG. 13 C, D are graphs of the respective tumor volumes (injected and non-injected) at day 18 post the first injections. (*, P<0.05; **, P<0.0001). (E) Kaplan-Meier survival curve of mice treated with PBS, VC-TK⁻, or Heat-iMVA. Survival data were analyzed by log-rank (Mantel-Cox) test. (*, P<0.001).

(FIG. 14 A, B, C) are graphs of volume of injected tumors at various days post injection with PBS (A; n=10), or with Heat-iMVA (B, n=10), or with VC-TK⁻-hFlt3L (C; n=8). FIG. 14D is a graph of initial tumor volumes of injected tumors at the time of first injection. FIG. 14E is a Kaplan-Meier survival curve of mice treated with PBS, Heat-iMVA, or VC-TK⁻-hFlt3L. Survival data were analyzed by log-rank (Mantel-Cox) test. (*, P<0.001 for VC-TK⁻-hFlt3L vs. PBS; **, P<0.0001 for Heat-iMVA vs. PBS).

DETAILED DESCRIPTION

Definitions

Figure 1A:
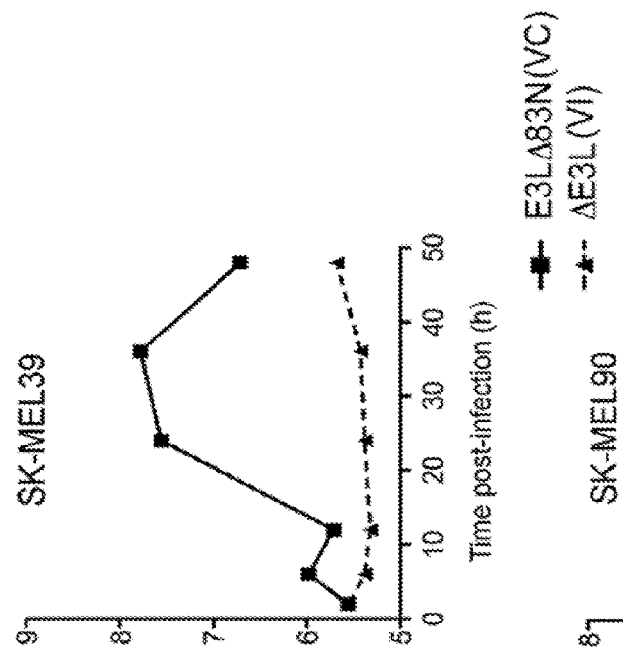
FIG. 1A-D is a series of graphs showing a one-step growth of E3LΔ83N (VC) and ΔE3L (VI) vaccinia viruses in murine and human melanoma cell lines. Murine B16-F10 melanoma cells and human melanoma cells SK-MEL39, SK-MEL188, and SK-MEL90 were infected with either E3LΔ83N (VC) or ΔF3L (VI) at a MOI of 5. Cells were collected at various times post infection and viral yields (log pfu) were determined.
Figure 1B:
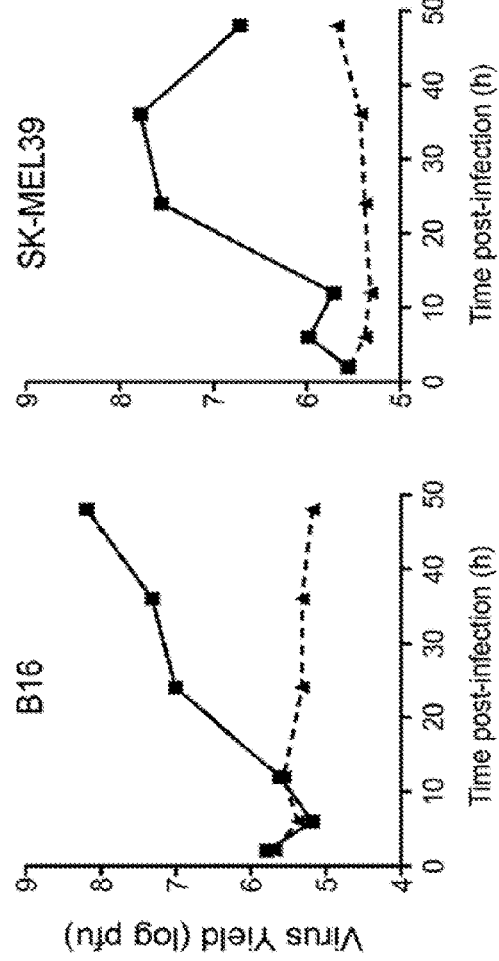
Figure 1C:
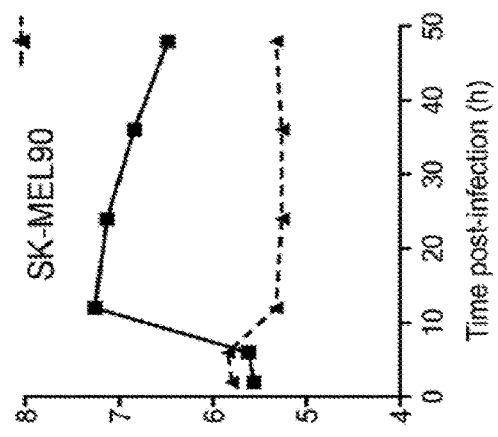
Figure 1D:
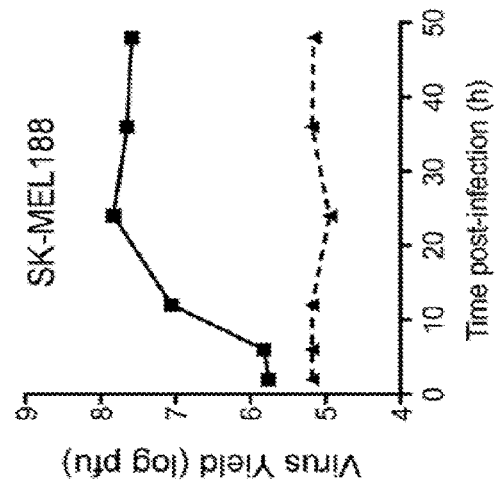

As used herein, the following terms shall have the meanings ascribed to them below unless the context clearly indicates otherwise:

"Cancer" refers to a class of diseases of humans and animals characterized by uncontrolled cellular growth. Unless otherwise explicitly indicated, the term "cancer" may be used herein interchangeably with the terms "tumor," "malignancy," "hyperproliferation" and "neoplasm(s);" the term "cancer cell(s)" is interchangeable with the terms "tumor cell(s)," "malignant cell(s)," "hyperproliferative cell(s)," and "neoplastic cell(s)".

"Melanoma" refers to a malignant neoplasm originating from cells that are capable of producing melanin. The term melanoma is synonymous with "malignant melanoma". Melanoma metastasizes widely, involving a patient's lymph nodes, skin, liver, lungs and brain tissues.

"Solid tumor" refers to all neoplastic cell growth and proliferation, and all pre-cancerous and cancerous cells and tissues, except for hematologic cancers such as lymphomas, leukemias and multiple myeloma. Examples of solid tumors include, but are not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Some of the most common solid tumors for which the compositions and methods of the present disclosure would be useful include: head-and-neck cancer, rectal adenocarcinoma, glioma, medulloblastoma, urothelial carcinoma, pancreatic adenocarcinoma, endometrial cancer, ovarian cancer, prostate adenocarcinoma, non-small cell lung cancer (squamous and adenocarcinoma), small cell lung cancer, melanoma, breast carcinoma, renal cell carcinoma, and hepatocellular carcinoma.

"Metastasis" refers to the spread of cancer from its primary site to neighboring tissues or distal locations in the body. Cancer cells can break away from a primary tumor, penetrate into lymphatic and blood vessels, circulate through the bloodstream, and grow in in normal tissues elsewhere in the body. Metastasis is a sequential process, contingent on tumor cells (or cancer stem cells) breaking off from the primary tumor, traveling through the bloodstream or lymphatics, and stopping at a distant site. Once at another site, cancer cells re-penetrate through the blood vessels or lymphatic walls, continue to multiply, and eventually form a new tumor (metastatic tumor). In some embodiments, this new tumor is referred to as a metastatic (or secondary) tumor.

"Immune response" refers to the action of one or more of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, etc. An immune response may include a cellular response, such as a T cell response that is an alteration (modulation, e.g., significant enhancement, stimulation, activation, impairment, or inhibition) of cellular function that is a T cell function. A T cell response may include generation, proliferation or expansion, or stimulation of a particular type of T cell, or subset of T cells, for example, $CD4^+$ helper, $CD8^+$ cytotoxic, or natural killer (NK) cells. Such T cell subsets may be identified by detecting one or more cell receptors or cell surface molecules (e.g., CD or cluster of differentiation molecules). A T cell response may also include altered expression (statistically significant increase or decrease) of a cellular factor, such as a soluble mediator (e.g., a cytokine, lymphokine, cytokine binding protein, or interleukin) that influences the differentiation or proliferation of other cells. For example, Type I interferon (IFN-$\alpha/\beta$) is a critical regulator of the innate immunity (Huber et al. *Immunology* 132(4):466-474 (2011). Animal and human studies have shown a role for IFN-$\alpha/\beta$ in directly influencing the fate of both $CD4^+$ and $CD8^+$ T cells during the initial phases of antigen recognition anti-tumor immune response. IFN Type I is induced in response to activation of dendritic cells, in turn a sentinel of the innate immune system.

"Tumor immunity" refers to one or more processes by which tumors evade recognition and clearance by the immune system. Thus, as a therapeutic concept, tumor immunity is "treated" when such evasion is attenuated or eliminated, and the tumors are recognized and attacked by the immune system (the latter being termed herein "anti-tumor immunity"). An example of tumor recognition is tumor binding, and examples of tumor attack are tumor reduction (in number, size or both) and tumor clearance.

"T cell" refers to a thymus derived lymphocyte that participates in a variety of cell-mediated adaptive immune reactions.

"Helper T cell" refers to a $CD4^+$ T cell; helper T cells recognize antigen bound to MHC Class II molecules. There are at least two types of helper T cells, Th1 and Th2, which produce different cytokines.

"Cytotoxic T cell" refers to a T cell that usually bears CD8 molecular markers on its surface (CD8+) (but may also be CD4+) and that functions in cell-mediated immunity by destroying a target cell having a specific antigenic molecule on its surface. Cytotoxic T cells also release Granzyme, a serine protease that can enter target cells via the perforin-formed pore and induce apoptosis (cell death). Granzyme serves as a marker of cytotoxic phenotype. Other names for cytotoxic T cell include CTL, cytolytic T cell, cytolytic T lymphocyte, killer T cell, or killer T lymphocyte. Targets of cytotoxic T cells may include virus-infected cells, cells infected with bacterial or protozoal parasites, or cancer cells. Most cytotoxic T cells have the protein CD8 present on their cell surfaces. CD8 is attracted to portions of the Class I MHC molecule. Typically, a cytotoxic T cell is a CD8+ cell.

"Tumor-infiltrating lymphocytes" refers to white blood cells of a subject afflicted with a cancer (such as melanoma), that are resident in or otherwise have left the circulation (blood or lymphatic fluid) and have migrated into a tumor.

"Immune checkpoint inhibitor(s)" or "immune checkpoint blocking agent" refers to molecules that completely or partially reduce, inhibit, interfere with or modulate the activity of one or more checkpoint proteins. Checkpoint proteins regulate T-cell activation or function. Checkpoint proteins include, but are not limited to CTLA-4 and its ligands CD80 and CD86; PD-1 and its ligands PDL1 and PDL2; LAG3, B7-H3, B7-H4, TIM3, ICOS, and BTLA (Pardoll et al. *Nature Reviews Cancer* 12: 252-264 (2012)).

"Parenteral" when used in the context of administration of a therapeutic substance includes any route of administration other than administration through the alimentary tract. Particularly relevant for the methods disclosed herein are intravenous (including for example through the hepatic portal vein), intratumoral or intrathecal administration.

"Antibody" refers to an immunoglobulin molecule which specifically binds to an antigen or to an antigen-binding fragment of such a molecule. Thus, antibodies can be intact immunoglobulins derived from natural sources or from recombinant sources and can be immunoreactive (antigen-binding) fragments or portions of intact immunoglobulins. The antibodies may exist in a variety of forms including, for example, polyclonal antibodies, monoclonal antibodies, Fv, Fab and F(ab)2, as well as single chain antibodies (scFv) humanized antibodies, chimeric antibodies, human recombinant antibodies and bi- and tri-specific antibodies.

"Oncolytic virus" refers to a virus that preferentially infects cancer cells, replicates in such cells, and induces lysis of the cancer cells through its replication process. Nonlimiting examples of naturally occurring oncolytic viruses include vesicular stomatitis virus, reovirus, as well as viruses engineered to be oncoselective such as adenovirus, Newcastle disease virus and herpes simplex virus (See, e.g., Nemunaitis, J. *Invest New Drugs*. 17(4):375-86 (1999); Kirn, D H et al. *Nat Rev Cancer*. 9(1):64-71(2009); Kirn et al. *Nat. Med*. 7:781 (2001); Coffey et al. *Science* 282:1332 (1998)). Vaccinia virus infects many types of cells but replicates preferentially in tumor cells due to the fact that tumor cells (i) have a metabolism that favors replication, (ii) exhibit activation of certain pathways that also favor replication and (iii) create an environment that evades the innate immune system, which also favors viral replication.

"Heat-inactivated" with particular reference to vaccinia viruses, including viral constructs harboring heterologous genes, such as GM-CSF and Flt3L, refers to a virus which has been further treated by exposure to heat under conditions that do not destroy its immunogenicity or its ability to enter target cells (tumor cells) but remove residual replication ability of the virus as well as factors that inhibit the host's immune response (for example, such factors as inhibit the induction of IFN Type I in infected cells). An example of such conditions is exposure to a temperature within the range of about 50 to about 60° C. for a period of time of about an hour. Other times and temperatures can be determined with routine experimentation and IFN Type I induction in infected cDC's can be compared to the Heat-inactivated virus used in experiments described herein and should be higher than that of vaccinia virus.

"UV-inactivated" with particular reference to vaccinia viruses, including viral constructs harboring heterologous genes, such as GM-CSF and Flt3L, refers to a virus which has been inactivated by exposure to UV under conditions that do not destroy its immunogenicity or its ability to enter target cells (tumor cells) but remove residual replication ability of the virus. An example of such conditions, which can be useful in the present methods, is exposure to UV using for example a 365 nm UV bulb for a period of about 30 min to about 1 hour (Tsung et al. *J Virol* 70,165-171 (1996); Drillien, R. et al. J Gen Virol 85: 2167-2175 (2004)).

"Subject" means any animal (mammalian, human or other) patient that can be afflicted with cancer.

"Therapeutically effective amount" or "effective amount" refers to a sufficient amount of an agent when administered at one or more dosages and for a period of time sufficient to provide a desired biological result in alleviating, curing or palliating a disease. In the present disclosure, an effective amount of the E3LΔ83N-TK$^-$, E3LΔ83N-TK$^-$-mGM-CSF, and E3LΔ83N-TK$^-$-hFlt3L and corresponding inactivated viruses is an amount that (administered for a suitable period of time and at a suitable frequency) accomplishes one or more of the following: reduces the number of cancer cells; or reduces the tumor size or eradicates the tumor; inhibits (i.e., slows down or stops) cancer cell infiltration into peripheral organs; inhibits (i.e., slows down or stops) metastatic growth; inhibits (i.e., stabilizes or arrests) tumor growth; allows for treatment of the tumor, and induces an immune response against the tumor. An appropriate therapeutic amount in any individual case may be determined by one of ordinary skill in the art using routine experimentation in light of the present disclosure. Such determination will begin with amounts found effective in vitro and amounts found effective in animals. The therapeutically effective amount will be initially determined based on the concentration or concentrations found to confer a benefit to cells in culture. Effective amounts can be extrapolated from data within the cell culture and can be adjusted up or down based on factors such as detailed herein. An example of an effective amount range is from $10^5$ viral particles to about $10^{12}$ viral particles per administration.

With particular reference to the viral-based immunostimulatory agents disclosed herein, "therapeutically effective amount" or "effective amount" refers to an amount of a composition comprising E3LΔ83N-TK$^-$, E3LΔ83N-TK$^-$-GM-CSF, E3LΔ83N-TK$^-$-hFlt3L and/or a corresponding inactivated virus sufficient to reduce, inhibit, or abrogate tumor cell growth, thereby reducing or eliminating the tumor, or sufficient to inhibit, reduce or abrogate metastatic spread either in vitro or in a subject or to elicit an immune response against the tumor that will eventually result in one or more of reduction, inhibition and/or abrogation as the case may be. The reduction, inhibition, or eradication of tumor cell growth may be the result of necrosis, apoptosis, or an immune response or a combination of two or more of the foregoing. The amount that is therapeutically effective may vary depending on such factors as the particular E3LΔ83N-TK$^-$, E3LΔ83N-TK$^-$-GM-CSF,E3LΔ83N-TK$^-$-hFlt3L and/or corresponding inactivated viruses used in the composition, the age and condition of the subject being treated, the extent of tumor formation, the presence or absence of other therapeutic modalities, and the like. Similarly, the dosage of the composition to be administered and the frequency of its administration will depend on a variety of factors, such as the potency of the active ingredient, the duration of its activity once administered, the route of administration, the size, age, sex and physical condition of the subject, the risk of adverse reactions and the judgment of the medical practitioner. The compositions are administered in a variety of dosage forms, such as injectable solutions.

With particular reference to combination therapy with an immune checkpoint inhibitor, "therapeutically effective amount" for an "immune checkpoint blocking or blockade agent" shall mean an amount of an immune checkpoint blocking agent sufficient to block an immune checkpoint from averting apoptosis response in tumor cells of the subject being treated. There are several immune checkpoint blocking agents approved, in clinical trials or still otherwise under development including CD28 inhibitors such as CTL4 inhibitors (e.g., ipilimumab), PD-1 inhibitors (e.g., nivolumab, pembrolizumab, pidilizumab, lambrolizumab), II DLBCL inhibitors such as AMP-224, PD-L1 inhibitors (MPDL3280A, BMS-936559, MEDI4736, MSB 00107180) ICOS and BTLA or decoy molecules of them. Dosage ranges of the foregoing are known in or readily within the skill in the art as several dosing clinical trials have been completed, making extrapolation to other agents possible.

Preferably, the tumor expresses the particular checkpoint. While this is desirable, it is not strictly necessary as immune checkpoint blocking agents block more generally immune suppressive mechanisms within the tumors, elicited by tumor cells, stromal cell, and tumor infiltrating immune cells.

For example, the CTLA4 inhibitor ipilimumab, when administered as adjuvant therapy after surgery in melanoma is administered at 1-2 mg/mL over 90 minutes for a total infusion amount of 3 mg/kg every three weeks for a total of 4 doses. This therapy is often accompanied by severe even life-threatening immune-mediated adverse reactions, which limits the tolerated dose as well as the cumulative amount that can be administered. This and other checkpoint blockade inhibitors, administered alone, are commonly given in amounts per dose ranging between 1 and 3 mg/mL(as shown below). It is anticipated that it will be possible to reduce the dose and/or cumulative amount of ipilimumab when it is administered conjointly with one or more of E3LΔ83N-TK$^-$, E3LΔ83N-TK$^-$-GM-CSF, and E3LΔ83N-TK$^-$-hFlt3L viruses. In particular, in light of the experimental results set forth below, it is anticipated that it will be further possible to reduce the CTLA4 inhibitor's dose if it is administered directly to the tumor simultaneously or sequentially with one or more of E3LΔ83N-TK$^-$, E3LΔ83N-TK$^-$-GM-CSF, and E3LΔ83N-TK$^-$-hFlt3L viruses and corresponding inactivated viral constructs. Accordingly, the amounts provided above for ipilimumab will be a starting point for determining the particular dosage and cumulative amount to be given to a patient in conjoint administration but dosing studies will be required to determine optimum amounts.

Pembrolizumab is prescribed for administration as adjuvant therapy in melanoma diluted to 25 mg/mL is administered at a dosage of 2 mg/kg over 30 minutes every three weeks.

Nivolumab is prescribed for administration at 3 mg/kg as an intravenous infusion over 60 minutes every two weeks. For therapeutic uses/applications human GM-CSF will be utilized. In the Examples described herein, mouse GM-CSF described as mGM-CSF is used in the model/experimental systems. Additionally, it is expected that multiple treatments with any one or more of the viruses of the present disclosure can be administered in multiple doses until the tumors resolve or are no longer responding to the treatment.

It will be understood that the foregoing combination therapies of one or more viruses with a checkpoint blockade inhibitor can be administered by one or more practitioners acting under each other's instructions or operating as a team.

"Pharmaceutically acceptable carrier and/or diluent" includes any and all solvents, dispersion media, coatings, antibacterial and antifungal agents, isotonic and absorption delaying agents and the like. The use of such media and agents for biologically active substances is well known in the art. Supplementary active ingredients, such as antimicrobials, can also be incorporated into the compositions.

"Delivering" used in connection with depositing one or more of E3LΔ83N-TK$^-$, E3LΔ83N-TK$^-$-GM-CSF, and E3LΔ83N-TK$^-$-Flt3L viruses of the present disclosure in the tumor microenvironment whether this is done by local administration to the tumor or by for example intravenous route. The term focuses on E3LΔ83N-TK$^-$, E3LΔ83N-TK$^-$-GM-CSF, E3LΔ83N-TK$^-$-hFlt3L viruses that reaches the tumor itself. "Delivering" is synonymous with administering but it is used with a particular administration locale in mind e.g. intratumoral.

In the present disclosure, the inventors generated recombinant E3LΔ83N-TK$^-$ virus expressing human Flt3L, with the goal of delivering this growth factor to the tumor microenvironment to facilitate recruitment, differentiation and function of immune cells, including CD103$^+$/CD8α dendritic cells (DCs). A somewhat similar strategy has been used and proven to be effective in the clinical development of JX-594 by Jennerex, in which vaccinia virus is engineered to express a transgene encoding granulocyte-macrophage colony stimulating factor (GM-CSF) with the deletion of vaccinia thymidine kinase (TK) gene to increase tumor selectivity. GM-CSF is another important growth factor for DC homeostasis at the peripheral non-lymphoid tissues (King et al., 2010; Greter et al., 2012). Melanoma vaccine (GVAX) comprises lethally irradiated allogeneic melanoma cells secreting GM-CSF has shown some clinical benefit (Dranoff et al., 2003). Curran and Allison showed that the combination of B16-GMCSF (GVAX) or B16-Flt3L (F13 VAX) with CTLA-4 blocking agent eradicated established melanoma in about 60% of the mice if the vaccines were administered at distal sites from the tumors (Curran and Allison, 2009). However, when the vaccines were administered to the tumors in combination with CTLA-4 blocking agent, GVAX was ineffective in tumor eradication, whereas Fl3 VAX treatment resulted in 75% of tumor-free mice. One potential explanation is that GM-CSF administration to the tumors might induce myeloid suppressor cell generation within the tumor (Serafini et al., 2004). With the concern that administration of GM-CSF to the tumors might induce immune tolerance, inventors of the present disclosure performed head-to-head comparisons of two recombinant viruses, with VC-TK$^-$ as a vector expressing hFlt3L or GM-CSF, and vector alone, for eradication of established B16 melanoma. The inventors discovered that VC-TK$^-$-hFlt3L is more efficacious than VC-TK$^-$-mGM-CSF or vector alone in eradicating or controlling tumor growth (Example 6). As described in Example 6, the inventors showed that while intratumor injection of attenuated replication competent VC-TK$^-$, VC-TK$^-$-mGM-CSF, or VC-TK$^-$-hFlt3L can effectively eradicate injected tumors, intratumoral delivery of VC-TK$^-$-hFlt3L is more efficacious than VC-TK$^-$-mGM-CSF in delaying the growth of contralateral tumor and extending survival. This systemic effect of VC-TK$^-$-hFlt3L is important not only for the treatment of noninjected tumors, but also for the treatment of metastatic disease.

Additionally, the inventors of the present disclosure have shown that intratumoral delivery of oncolytic viruses overcomes the resistance to immune checkpoint blocking agents. As shown in Example 7, the combination of intratumoral delivery of either VC-TK$^-$-mGM-CSF, or VC-TK$^-$-hFlt3L with systemic delivery of anti-CTLA-4 antibody lead to the eradication of 10/10 injected tumors, and significant delay of the growth of contralateral non-injected tumors, as well as complete eradication of tumors in 40-60% of the cases. However, intratumoral delivery of VC-TK$^-$-hFlt3L in combination with anti-CTLA-4 antibody was more efficacious than VC-TK$^-$-mGM-CSF in combination with anti-CTLA-4 antibody in delaying the growth of contralateral tumor and extending survival of treated mice. These results indicate for the first time that VC-TK$^-$-hFlt3L may provide a successful and indeed a superior option for the treatment of melanoma patients, alone or in combination with immune checkpoint blocking agents.

In the present disclosure, the inventors further explored whether inactivated VC-TK$^-$-mGM-CSF strain can be used as cancer immunotherapeutic agent. In fact, they observed that intratumoral delivery of Heat-inactivated VC-TK$^-$-mGM-CSF is more efficacious in eradicating tumors and generating antitumoral adaptive immunity than live VC-TK$^-$-mGM-CSF (Example 8). Thus, as a treatment option, patients can be treated with Heat-inactivated VC-TK$^-$-mGM-CSF in order to achieve improved treatment results. It is anticipated that similar results will be observed if instead of heat-inactivating the virus, ultraviolet irradiation (UV) inactivation is employed instead.

Furthermore, the inventors of the present disclosure have shown that the combination of intratumoral injection of VC-TK$^-$-mGM-CSF or Heat-inactivated VC-TK$^-$-mGM-CSF with intraperitoneal delivery of immune checkpoint blocking agent leads to synergistic therapeutic effects (Example 9).

In one embodiment, the present disclosure relates to a method for eliciting an antitumor immune response in subjects with tumors comprising delivering to the tumor an effective amount of one or more of E3LΔ83N-TK$^-$, E3LΔ83N-TK$^-$-GM-CSF, and E3LΔ83N-TK$^-$-hFlt3L viruses. Stimulation of the immune system may be manifest by one or more of the following immunological effects:

an increase in cytotoxic CD8+ T cells within the tumor and/or in tumor-draining lymph nodes;

induction of maturation of dendritic cells infiltrating said tumor through induction of type I IFN;

induction of activated T helper cells in the subject recognizing tumor cells within the tumor and/or in tumor draining lymph nodes increase of CD103$^+$ dendritic cells in noninjected tumors of the subject (especially for the hFLT3L construct).

The foregoing one or more immunological effects may serve as early indicators of response of the subject to the treatment and may serve as monitors of the continued effectiveness of same.

In one embodiment, the present disclosure provides a method of treating a subject diagnosed with a solid tumor comprising delivering to the tumor a therapeutic effective amount of one or more of E3LΔ83N-TK$^-$, E3LΔ83N-TK$^-$-GM-CSF, and E3LΔ83N-TK$^-$-hFlt3L viruses.

In one embodiment, the present disclosure provides a method for inducing anti-tumor immunity in a subject diagnosed with cancer comprising administering to the subject a therapeutically effective amount of one or more of E3LΔ83N-TK$^-$, E3LΔ83N-TK$^-$-GM-CSF, and E3LΔ83N-TK$^-$-hFlt3L viruses. The methods of the present disclosure include induction of anti-tumor immunity that can reduce the size of the tumor, eradicate the tumor, inhibit growth of the tumor, inhibit metastasis or metastatic growth of the tumor, induce apoptosis of tumor cells or prolong survival of the subject (compared to untreated or conventionally treated subjects).

In another embodiment, the present disclosure provides a method for enhancing, stimulating, or eliciting, in a subject diagnosed with a solid malignant tumor, an anti-tumor immune response that may include an innate immune response and/or an adaptive immune response such as a T cell response by exposing the tumor to one or more of E3LΔ83N-TK$^-$, E3LΔ83N-TK$^-$-GM-CSF, and E3LΔ83N-TK$^-$-hFlt3L viruses in a therapeutically effective amount.

In specific embodiments, the present disclosure provides methods of eliciting an immune response that mediates adaptive immune responses both in terms of T-cell cytotoxicity directed against tumor cells and in terms of eliciting T helper cells also directed against tumor cells. The methods comprise administering to a subject afflicted with a solid tumor intratumorally or intravenously a composition comprising one or more of E3LΔ83N-TK$^-$, E3LΔ83N-TK$^-$-GM-CSF, and E3LΔ83N-TK$^-$-hFlt3L viruses wherein administration of said composition results in a tumor-specific immune response against the tumor and, eventually, in reduction, inhibition or eradication of tumor growth, in inhibition of metastatic growth, apoptosis of tumor cells and/or prolongation of the subject's survival. Indeed the present inventors have shown that cancer cells are being killed and that the immune response can migrate to remote locations, as would be the case with metastases.

In some embodiments, the present disclosure provides methods of eliciting an immune response that mediates adaptive immune responses both in terms of T-cell cytotoxicity directed against tumor cells and in terms of eliciting T helper cells also directed against tumor cells. The methods comprise administering to a subject parenterally a composition comprising one or more of E3LΔ83N-TK$^-$, E3LΔ83N-TK$^-$-mGM-CSF, and E3LΔ83N-TK$^-$-hFlt3L viruses wherein administration of said composition results in a tumor-specific immune response against the tumor and, eventually, in reduction, inhibition or eradication of tumor growth and/or in inhibition of metastatic growth, apoptosis of tumor cells and/or prolongation of survival of the treated subject. For intraperitoneal metastases, the viruses can be injected intraperitoneally. For brain metastasis, the viruses can be injected intratumorally under stereotactic guidance, or intrathecally.

Indeed the present inventors have shown that cancer cells are being killed and that the immune response can migrate to remote locations, as would be the case with metastases.

The present disclosure thus provides a method for treating a solid malignant tumor, delivering to a tumor of the subject an amount of E3LΔ83N-TK$^-$, E3LΔ83N-TK$^-$-GM-CSF, and/or E3LΔ83N-TK$^-$-hFlt3L virus effective to induce a therapeutic immune response in a subject diagnosed with solid tumor.

As is shown herein, current literature, and without wishing to be bound by theory, the following mechanisms are believed to contribute to anti-tumor effects of E3LΔ83N-TK$^-$, E3LΔ83N-TK$^-$-GM-CSF, and E3LΔ83N-TK$^-$-hFlt3L viruses: (i) oncolysis of tumor cells and release of tumor antigens; (ii) induction of cytotoxic CD8+ and effector CD4$^+$ T cells in the tumors and tumor draining lymph nodes; (iii) alteration of tumor immune suppressive environment through the release of viral DNA and RNA; and (iv) induction of anti-tumor antibodies.

Immune Response

In addition to induction of the immune response by up-regulation of particular immune system activities (such as antibody and/or cytokine production, or activation of cell mediated immunity), immune responses may also include suppression, attenuation, or any other down-regulation of detectable immunity, so as to reestablish homeostasis and prevent excessive damage to the host's own organs and tissues. In some embodiments, an immune response that is induced according to the methods of the present disclosure generates cytotoxic CD8$^+$ T cells or activated T helper cells or both that can bring about directly or indirectly the death, or loss of the ability to propagate, of a tumor cell.

Induction of an immune response by the methods of the present disclosure may be determined by detecting any of a variety of well-known immunological parameters (Takaoka et al., Cancer Sci. 94:405-11 (2003); Nagorsen et al., Crit. Rev. Immunol. 22:449-62 (2002)). Induction of an immune response may therefore be established by any of a number of well-known assays, including immunological assays, Such assays include, but need not be limited to, in vivo, ex vivo, or in vitro determination of soluble immunoglobulins or antibodies; soluble mediators such as cytokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, altered intracellular cation gradient or concentration (such as calcium); phosphorylation or dephosphorylation of cellular polypeptides; induction of specialized activities such as specific gene expression or cytolytic behavior; cellular differentiation by cells of the immune system, including altered surface antigen expression profiles, or the onset of apoptosis (programmed cell death); or any other criterion by which the presence of an immune response may be detected. For example, cell surface markers that distinguish immune cell types may be detected by specific antibodies that bind to CD4$^+$, CD8$^+$, or NK cells. Other markers and cellular components that can be detected include but are not limited to interferon γ (IFN-γ), tumor necrosis factor (TNF), IFN-α, IFN-β, IL-6, and CCL5. Common methods for detecting the immune response include, but are not limited to flow cytometry, ELISA, immunohistochemistry. Procedures for performing these and similar assays are widely known and may be found, for example in Letkovits (Immunology Methods Manual: The Comprehensive Sourcebook of Techniques, Current Protocols in Immunology, 1998).

Pharmaceutical Compositions and Preparations

Pharmaceutical compositions comprising E3LΔ83N-TK$^-$, E3LΔ83N-TK$^-$-GM-CSF, and/or E3LΔ83N-TK$^-$-hFlt3L viruses may contain a carrier or diluent, which can be a solvent or dispersion medium containing, for example, water, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be effected by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Pharmaceutical compositions and preparations comprising E3LΔ83N-TK$^-$, E3LΔ83N-TK$^-$-GM-CSF, and/or E3LΔ83N-TK$^-$-hFlt3L viruses may be manufactured by means of conventional mixing, dissolving, granulating, dragee-making, levigating, emulsifying, encapsulating, entrapping or lyophilizing processes. Pharmaceutical viral compositions may be formulated in conventional manner using one or more physiologically acceptable carriers, diluents, excipients or auxiliaries that facilitate formulating virus preparations suitable for in vitro, in vivo, or ex vivo use. The compositions can be combined with one or more additional biologically active agents (for example parallel administration of GM-CSF) and may be formulated with a pharmaceutically acceptable carrier, diluent or excipient to generate pharmaceutical (including biologic) or veterinary compositions of the instant disclosure suitable for parenteral or intra-tumoral administration. Suitable excipient vehicles include, for example, water, saline, dextrose, glycerol, ethanol, inert proteins, hydrophillic polymers, amino acids, fatty acids, surfactants, non-ionic surfactants, carbohydrates, dextrins, polyols, chelating agents, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins.

Many types of formulation are possible and well-known. The particular type chosen is dependent upon the route of administration chosen, as is well-recognized in the art. For example, systemic formulations will generally be designed for administration by injection, e.g., intravenous, as well as those designed for intratumoral delivery. Preferably, the systemic or intratumoral formulation is sterile.

Sterile injectable solutions are prepared by incorporating E3LΔ83N-TK$^-$, E3LΔ83N-TK$^-$-GM-CSF, and/or E3LΔ83N-TK$^-$-hFlt3L viruses in the required amount of the appropriate solvent with various other ingredients enumerated herein, as required, followed by suitable sterilization means. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum drying and freeze-drying techniques, which yield a powder of the inactive-E3LΔ83N-TK$^-$, E3LΔ83N-TK$^-$-GM-CSF, and/or E3LΔ83N-TK$^-$-hFlt3L viruses, and plus any additional desired ingredient from a previously sterile-filtered solution thereof.

Dosage of E3LΔ83N-TK$^-$, E3LΔ83N-TK$^-$-GM-CSF, E3LΔ83N-TK$^-$-hFlt3L Viruses

In general, the subject is administered a unit dosage of E3LΔ83N-TK$^-$, E3LΔ83N-TK$^-$-GM-CSF, and/or E3LΔ83N-TK$^-$-hFlt3L viruses in the range of about $10^5$ to about $10^{10}$ plaque forming units (pfu), although a lower or higher dose may be administered. In a preferred embodiment, dosage is about $10^6$-$10^9$ pfu. Typically, a unit dosage is administered in a volume within the range from 1 to 10 ml. The equivalence of pfu to virus particles can differ according to the specific pfu titration method used. Generally, pfu is equal to about 5 to 100 virus particles. A therapeutically effective amount of E3LΔ83N-TK$^-$, E3LΔ83N-TK$^-$-GM-CSF, E3LΔ83N-TK$^-$-hFlt3L viruses can be administered in one or more divided doses for a prescribed period of time and at a prescribed frequency of administration. For example, therapeutically effective amount of E3LΔ83N-TK$^-$, E3LΔ83N-TK$^-$-GM-CSF, E3LΔ83N-TK$^-$-hFlt3L viruses in accordance with the present disclosure may vary according to factors such as the disease state, age, sex, weight, and general condition of the subject, and the ability of E3LΔ83N-TK$^-$, E3LΔ83N-TK$^-$-GM-CSF, E3LΔ83N-TK$^-$-hFlt3L viruses to elicit a desired immunological response in the particular subject.

As is apparent to persons working in the field of cancer therapy, variation in dosage will necessarily occur depending for example on the condition of the subject being treated, route of administration and the subject's response to the therapy. In delivering E3LΔ83N-TK$^-$, E3LΔ83N-TK$^-$-GM-CSF, and/or E3LΔ83N-TK$^-$-hFlt3L viruses to a subject, the dosage will also vary depending upon such factors as the general medical condition, previous medical history, disease progression, tumor burden, ability to mount an immune response, and the like.

It may be advantageous to formulate compositions of present disclosure in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically or veterinary acceptable carrier.

Administration and Therapeutic Regimen of E3LΔ83N-TK$^-$, E3LΔ83N-TK$^-$-GM-CSF, and/or E3LΔ83N-TK$^-$-hFlt3L viruses Administration of one or more of E3LΔ83N-TK$^-$, E3LΔ83N-TK$^-$-GM-CSF, E3LΔ83N-TK$^-$-hFlt3L viruses can be achieved using a combination of routes, including parenteral, intratumoral, intrathecal or intravenous administration. In one embodiment, one or more of E3LΔ83N-TK$^-$, E3LΔ83N-TK$^-$-GM-CSF, E3LΔ83N-TK$^-$-hFlt3L viruses are administered directly into the tumor, e.g. by intratumoral injection, where a direct local reaction is desired. Additionally, administration routes of E3LΔ83N-TK$^-$, E3LΔ83N-TK$^-$-GM-CSF, and/or E3L483N-TK$^-$-hFlt3L viruses can vary, e.g., first administration using an intratumoral injection, and subsequent administration via an intravenous injection, or any combination thereof. A therapeutically effective amount of one or more of E3LΔ83N-TK$^-$, E3LΔ83N-TK$^-$-GM-CSF, and E3LΔ83N-TK$^-$-hFlt3L viruses injection can be administered for a prescribed period of time and at a prescribed frequency of administration. In certain embodiments, E3LΔ83N-TK⁻, E3LΔ83N-TK⁻-GM-CSF, E3LΔ83N-TK⁻-hFlt3L viruses can be used in conjunction with other therapeutic treatments. For example, E3LΔ83N-TK⁻, E3LΔ83N-TK⁻-GM-CSF, and/or E3LΔ83N-TK⁻-hFlt3L viruses can be administered in a neoadjuvant (preoperative) or adjuvant (postoperative) setting for subjects inflicted with bulky primary tumors. It is anticipated that such optimized therapeutic regimen will induce an immune response against the tumor, and reduce the tumor burden in a subject before or after primary therapy, such as surgery. Furthermore, E3LΔ83N-TK⁻, E3LΔ83N-TK⁻-GM-CSF, and E3LΔ83N-TK⁻-hFlt3L viruses can be administered in conjunction with other therapeutic treatments such as chemotherapy or radiation.

In certain embodiments, the E3LΔ83N-TK⁻, E3LΔ83N-TK⁻-GM-CSF, and E3LΔ83N-TK⁻-hFlt3L viruses are administered at least once weekly or monthly but can be administered more often if needed, such as two times weekly for several weeks, months, years or even indefinitely as long as benefit persist. More frequent administrations are contemplated if tolerated and if they result in sustained or increased benefits. Benefits of the present methods include but are not limited to the following: reduction of the number of cancer cells, reduction of the tumor size, eradication of tumor, inhibition of cancer cell infiltration into peripheral organs, inhibition or stabilization of metastatic growth, inhibition or stabilization of tumor growth, and stabilization or improvement of quality of life. Furthermore, the benefits may include induction of an immune response against the tumor, activation of T helper cells, an increase of cytotoxic $CD8^+$ T cells, or reduction of regulatory $CD4^+$ cells. For example, in the context of melanoma or, a benefit may be a lack of recurrences or metastasis within one, two, three, four, five or more years of the initial diagnosis of melanoma. Similar assessments can be made for colon cancer and other solid tumors.

In certain other embodiments, the tumor mass or tumor cells are treated with one or more of E3LΔ83N-TK⁻, E3LΔ83N-TK⁻-GM-CSF, and E3LΔ83N-TK⁻-hFlt3L viruses in vivo, ex vivo, or in vitro.

Kits

The present disclosure contemplates the provision of kits comprising one or more compositions comprising one or more of the E3LΔ83N-TK⁻, E3LΔ83N-TK⁻-GM-CSF, or E3LΔ83N-TK⁻-hFlt3L viruses described herein. The kit can comprise one or multiple containers or vials of the virus, together with instructions for the administration of the virus to a subject to be treated. The instructions may indicate a dosage regimen for administering the composition or compositions as provided below.

In some embodiments, the kit may also comprise an additional composition comprising a checkpoint inhibitor for conjoint administration with any of the virus compositions described herein.

EXAMPLES

Materials and Methods

Viruses and Cell Lines

E3LΔ83N (VC) and ΔF3L (VI) viruses were kindly provided by B. L. Jacobs (Arizona State University). They were propagated in BSC40 cells and viral titers were determined by plaque assay using BSC40 cells. VC-TK⁻, VC-TK⁻-mGM-CSF, VC-TK⁻-hFlt3L viruses were generated through homologous recombination at the thymidine kinase (TK) locus (see Example 2). These recombinant viruses were enriched through culturing in gpt selection medium and plaque purified in the presence of selection medium through more than five rounds. The pure recombinant clones were amplified in the absence of selection medium. After validation, the viruses were purified through a 36% sucrose cushion.

MVA virus was kindly provided by Gerd Sutter (University of Munich), propagated in BHK-21 (baby hamster kidney cell, ATCC CCL-10) cells. Heat-inactivated MVA and Heat-inactivated VC-TK⁻-mGM-CSF were generated by incubating purified respective viruses at 55° C. for 1 hour. Heat-inactivation led to reduction of infectivity by 1,000-fold.

BSC40 cells were cultured in Dulbecco's modified Eagle's medium (DMEM) supplemented containing 10% FBS, 0.1 mM nonessential amino acids (NEAA), and 50 mg/ml gentamycin. RK13 (rabbit kidney) cells were cultured in modified Eagle's medium containing 10% FBS, 0.1 mM nonessential amino acids, and 50 g/ml gentamicin. The murine melanoma cell line B16-F10 was originally obtained from I. Fidler (MD Anderson Cancer Center). B16-F10 cells were maintained in RPMI 1640 medium supplemented with 10% fetal bovine serum (FBS), 100 Units/ml penicillin, 100 µg/ml streptomycin, 0.1 mM NEAA, 2 mM L-glutamine, 1 mM sodium pyruvate, and 10 mM HEPES buffer. The human melanoma SK-MEL-39, SK-MEL-188, SK-MEL90, SK-MEL90, and SK-MEL-28 cells were cultured in MEM medium supplemented with 10% FBS and 4 mm L-Glutamine. All cells were grown at 37° C. in a 5% $CO_2$ incubator. Murine triple negative breast cancer cell line 4T1 was cultured in the RPMI medium with 10% FBS.

One-Step Growth in Cell Culture

B16-F10 cells and human melanoma cells were cultured overnight prior to infection with viruses, including ΔE3L (VI), E3LΔ83N (VC), VC-TK⁻, VC-TK⁻-mGM-CSF, VC-TK⁻-hFlt3L) at a low MOI. The inoculum was removed after 60 min; the cells were washed twice with PBS and then overlaid with medium. The cells were harvested at 1, 4, 12, 24, 48, and some cases 72 h after initial infection by scraping the cells into 1 ml of medium. After three cycles of freezing and thawing, the samples were sonicated and virus titers (for all of the viruses except for ΔE3L) were determined by serial dilution and infection of BSC40 cell monolayers. ΔE3L viral titers were determined on RK13 cells. Plaques were visualized by staining with 0.1% crystal violet in 20% ethanol.

Western Blot Analysis

Murine melanoma B16-F10 cells or human melanoma cells SK-MEL-28, SK-MEL146 ($1 \times 10^6$) were infected with E3LΔ83N-TK⁻-mGM-CSF or E3LΔ83N-TK⁻-hFlt3L viruses at a MOI (multiplicity of infection) of 10. At various times post-infection, the supernatants and cell lysates were collected. Equal amounts of proteins were subjected to sodium dodecyl sulfate-polyacrylamide gel electrophoresis and the polypeptides were transferred to a nitrocellulose membrane. The level of mGM-CSF and hFlt3L expression was determined by using an anti-mGM-CSF or anti-hFlt3L antibody. Anti-glyceraldehyde-3-phosphate dehydrogenase (GADPH) antibody (Cell Signaling) was used as a loading control.

Mice

Female C57BL/6J and BALB/c mice between 6 and 8 weeks of age were purchased from the Jackson Laboratory and were used for in vivo tumor implantation and treatment experiments. These mice were maintained in the animal facility at the Sloan Kettering Institute. All procedures were performed in strict accordance with the recommendations in the Guide for the Care and Use of Laboratory Animals of the National Institute of Health. The protocol was approved by the Committee on the Ethics of Animal Experiments of Sloan Kettering Cancer Institute.

Tumor Implantation and Intratumoral Injection with Viruses in the Presence or Absence of Systemic or Intratumoral Administration of Immune Checkpoint Blockade B16-F10 melanoma cells ($5\times10^5$) were implanted intradermally into the shaved skin on the right flank a C57BL/6J mouse, whereas fewer cells ($1\times10^5$) were implanted to the left flank of the same mouse. After 7 to 8 days post implantation, tumor sizes were measured and tumors that are 3 mm in diameter or larger on the right flank of the mice were injected with VC-TK$^-$, VC-TK$^-$-mGM-CSF, VC-TK$^-$-hFlt3L viruses ($2\times10^7$ pfu) or PBS when the mice were under anesthesia. Viruses were injected twice weekly. Mice were monitored daily and tumor sizes were measured twice a week. Tumor volumes were calculated according the following formula: 1 (length)×w (width)×h(height)/2. The survival of mice was monitored. Mice were euthanized for signs of distress or when the diameter of the tumor reached 10 mm. In some experimental groups, the mice were treated with intraperitoneal delivery of anti-CTLA-4 (100 µg per mouse) or anti-PD-L1 antibodies (250 µg per mouse) twice weekly.

In some experiments, 4T1 murine triple negative breast cancer (TNBC) cells were implanted intradermally to the left and right flanks of BALB/c mice ($2.5\times10^5$ to the right flank and $5\times10^4$ to the left flank). 5 days post tumor implantation, the larger tumors on the right flank were injected with either Heat-iMVA or VC-TK$^-$ virus ($2\times10^7$ pfu) twice weekly. Mice were monitored daily and tumor sizes were measured twice a week. The survival of mice was monitored.

Unilateral Intradermal Tumor Implantation and Intratumoral Injection with Viruses B16-F10 melanoma ($5\times10^5$ cells in a volume of 50 µl) were implanted intradermally into the shaved skin on the right flank of WT C57BL/6J mice. After 9 days post implantation, tumor sizes were measured and tumors that are 5-6 mm in diameter were injected with Heat-iMVA (equivalent of $2\times10^7$ pfu of MVA in a volume of 50 µl) or with VC-TK$^-$-mGM-CSF, or with PBS when the mice were under anesthesia twice weekly. Mice were monitored daily and tumor sizes were measured twice a week. Tumor volumes were calculated according the following formula: 1(length)×w (width)×h(height)/2. Mice were euthanized for signs of distress or when the diameter of the tumor reached 15 mm.

Tumor Challenge to Assess the Development of Cross-Protective Antitumor Immunity The surviving mice (more than 60 days post initiation of intratumoral virotherapy) and nave mice were challenged with intradermally delivery of a lethal dose of MC38 ($1\times10^5$ cells) to assess cross-protective immunity against heterologous tumors.

Preparation of Tumor Cell Suspensions

To analyze immune cell phenotypes and characteristics in the tumors, we generated cell suspensions prior to FACS analysis according to the following protocol (Zamarin et al., *Science Translational Medicine* 6, 226-232 (2014)). First we isolated injected and/or non-injected tumors using forceps and surgical scissors three days post second treatment and 7 days post first treatment with PBS or viruses. The tumors were then weighed. Tumors were minced prior to incubation with Liberase (1.67 Wünsch U/ml) and DNase (0.2 mg/ml) for 30 minutes at 37° C. Cell suspensions were generated by repeated pipetting, filtered through a 70-µm nylon filter, and then washed with complete RPMI.

Flow Cytometry Analysis of Tumor Infiltrating Immune Cells

In the bilateral tumor implantation model, $5\times10^5$ B16-F10 melanoma cells were implanted intradermally to the right flank and $2.5\times10^5$ cells to the left flank of C57B/6 mice. Seven days post implantation, either VC-TK$^-$ or VC-TK$^-$-hFlt3L ($2\times10^7$ pfu) or PBS were injected into the tumors on the right flank. The injections were repeated three days later. Tumors were harvested 3 days post last injection and cell suspensions were generated. Cells were processed for surface labeling with anti-CD3, CD45, CD4, and CD8 antibodies. Live cells are distinguished from dead cells by using fixable dye eFluor506 (eBioscience). They were further permeabilized using permeabilization kit (eBioscience), and stained for Granzyme B. For the staining of the myeloid cell population, fluorochromeconjugated antibodies against CD45.2 (104), CD11b (M1/70), Ly-6C (HK1.4), MHC II (M5/114.15.2), CD24 (M1/69), F4/80 (BM8), CD103 (2E7) and CD11c (N418) were purchased from eBioscience. All antibodies were tested with their respective isotype controls. Data were acquired using the LSRII Flow cytometer (BD Biosciences). Data were analyzed with FlowJo software (Treestar).

Reagents

The commercial sources for reagents were as follows: anti-mGM-CSF and anti-hFlt3L antibodies were purchased from R & D. Therapeutic anti-CTLA4 (clone 9H10 and 9D9), anti-PD-L1 (clone 10F-9G2) were purchased from BioXcell, West Lebanon, N.H. hFlt3L and mGM-CSF expression plasmids were purchased from GE. Antibodies used for flow cytometry were purchased from eBioscience (CD45.2 Alexa Fluor 700, CD3 PE-Cy7, CD4 APC-efluor780, CD8 PerCP-efluor710), Invitrogen (CD4 QDot 605, Granzyme B PE-Texas Red, Granzyme B APC). Fluorochromeconjugated antibodies against CD45.2 (104), CD11b (M1/70), Ly-6C (HK1.4), MHC II (M5/114.15.2), CD24 (M1/69), F4/80 (BM8), CD103 (2E7) and CD11c (N418) were purchased from eBioscience.

Statistics

Two-tailed unpaired Student's t test was used for comparisons of two groups in the studies. Survival data were analyzed by log-rank (Mantel-Cox) test. The p values deemed significant are indicated in the figures as follows: *, $p<0.05$; , $p<0.01$; *, $p<0.001$; ****, $p<0.0001$. The numbers of animals included in the study are discussed in each figure legend.

Example 1

E3LΔ83N Virus (VC) Replicates in Murine and Human Melanoma Cells

To test whether E3LΔ83N (the parental VC virus for the present experiments) or ΔE3L replicates in murine or human melanoma cells, murine B16 melanoma cells, human melanoma cells SK-MEL39, SK-MEL188, and SK-MEL90 were infected with either E3LΔ83N or ΔF3L viruses at a multiplicity of infection (MOI) of 5. Cells were collected at various times post-infection (up to 50 hours post-infection). Virus yields (log PFU) were determined by titration on BSC40 cell monolayers. As shown in FIGS. 1A-1D, E3LΔ83N virus (VC) could replicate efficiently in all of the murine and human melanoma cells tested, whereas ΔE3L virus (VI) failed to replicate in those cell lines.

Example 2

Generation of Recombinant E3LΔ83N-TK⁻ Viruses with or without GM-CSF or Flt3L

Figure 2:
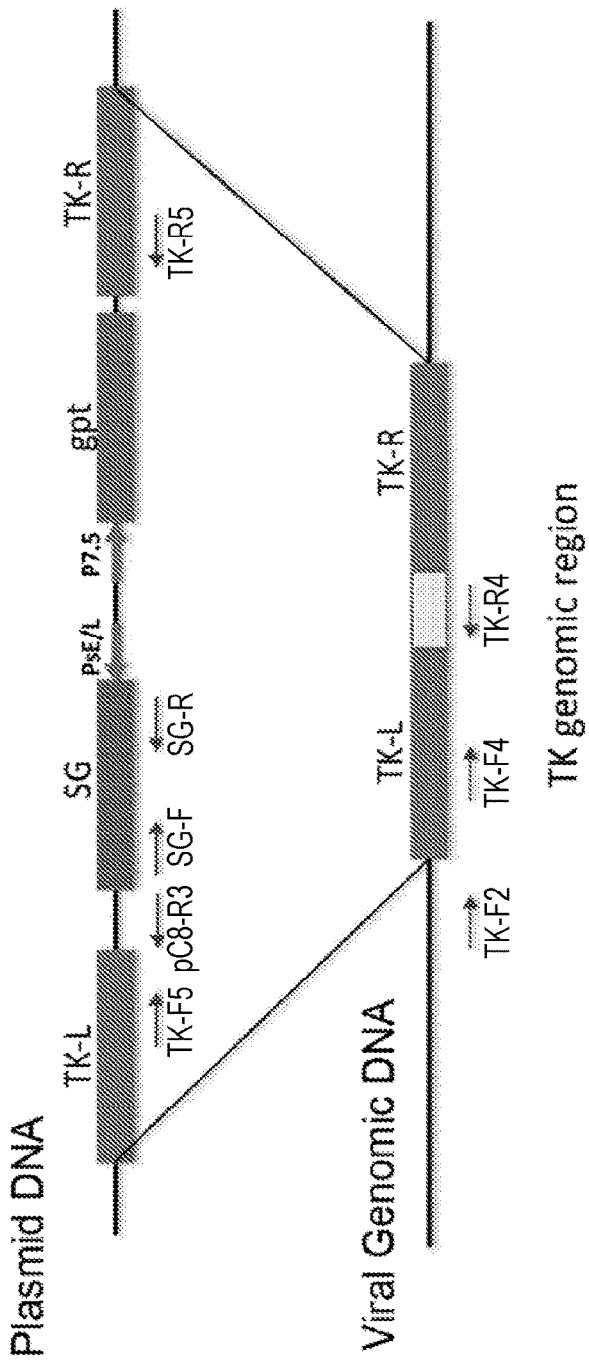
FIG. 2 is a schematic diagram of homologous recombination between plasmid DNA and viral genomic DNA at the thymidine kinase (TK) locus. pCB plasmid was used to insert specific gene of interest (SG), in this case, murine GM-CSF (mGM-CSF), and human Flt3L (hFlt3L) under the control of the vaccinia synthetic early and late promoter (Pse/l). The *E. coli* xanthine-guanine phosphoribosyl transferase gene (gpt) under the control of vaccinia P7.5 promoter was used as a drug selection marker. These two expression cassettes were flanked by partial sequence of TK gene (TK-L and TK-R) on each side. The plasmid DNA lacking SG was used as a vector control. Homologous recombination that occurred at the TK locus of the plasmid DNA and VC genomic DNA results in the insertion of SG and gpt expression cassettes or gpt alone into the VC genomic DNA to generate VC-TK$^-$-mGM-CSF, VC-TK$^-$-hFlt3L, or VC-TK$^-$. The recombinant viruses were enriched in the presence of gpt selection medium including MPA, xanthine and hypoxanthine, and plaque purified in the presence of the drug selection medium for 4-5 rounds until the appropriate recombinant viruses without contaminating VC were obtained.

It has been previously shown that oncolytic vaccinia viruses with the deletion of thymidine kinase (TK⁻) are more attenuated and more tumor selective than TK⁺ viruses (Buller et al. 1988; Puhlmann et al., 2000). In the present disclosure, the inventors generated recombinant VC viruses comprising a TK-deletion with and without expressing human Flt3L (hFlt3L) or murine GM-CSF (mGM-CSF) under the vaccinia synthetic early/late promoter (Pse/1) using standard recombinant virus technology through homologous recombination at the TK locus between the plasmid DNA and viral genomic DNA. First, the inventors constructed a plasmid containing specific gene of interest (SG) under the control of the vaccinia Pse/1 as well as the *E. coli* xanthineguanine phosphoribosyl transferase gene (gpt) under the control of vaccinia P7.5 promoter flanked by the thymidine kinase (TK) gene on either side (FIG. 2) BSC40 cells were infected with VC virus at a MOI of 0.05 for 1 h, and then were transfected with the plasmid DNAs described above. The infected cells were collected at 48 h. Recombinant viruses were selected through further culturing in gpt selection medium including MPA, xanthine and hypoxanthine, and plaque purified (Lorenzo et al., 2004). PCR analysis was performed to identify recombinant viruses with loss of part of the TK gene and with and without murine GM-CSF, or human Flt3L, (FIG. 3).

Figure 3:
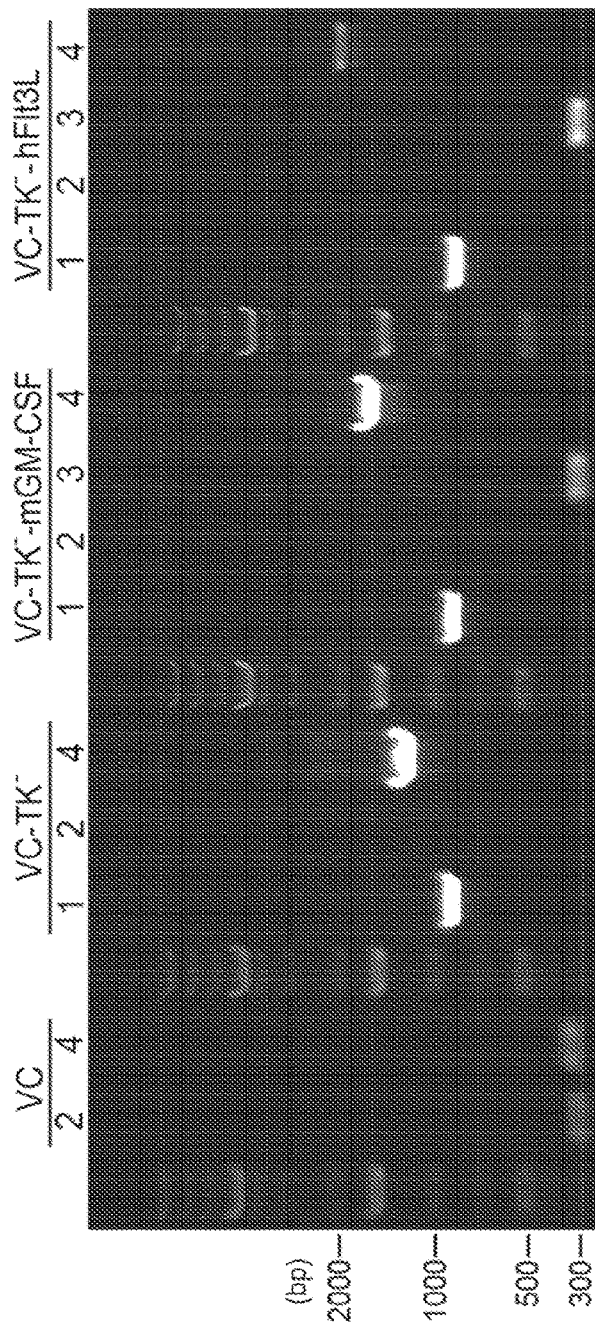
FIG. 3 is an image of PCR analysis of recombinant viruses, showing successful generation of VC-TK$^-$, VC-TK$^-$-mGM-CSF, and VC-TK$^-$-hFlt3L. VC recombinant viruses genomic DNAs were analyzed by PCR to verify the insertions and to make sure there were no contaminating patent virus particles (VC).

Oligonucleotide primers were designed to amplify DNA fragments of different sizes to identify VC recombinant viruses with different insertions (table in FIG. 3). For example, Primers TK-F2, which is adjacent to insertion site on the VC genome, and pCB-R3, which is on the vector, were used to check homologous insertion of target genes. Primers TK-R4, which is missing in recombinant virus, and TK-F4, were used to distinguish the recombinant and parent viruses. Gene specific primers were used to check the insertions of murine GM-CSF and human Flt3L genes. Primers TK-F5/TK-R5, which are located in the flanking region of vaccinia TK gene (NCBI GenBank Reference NC_006998.1 (80724 ... 81257)), were used to amplify the target gene for sequence verification. Expected fragments are shown in the table in FIG. 3. Gene specific primers mGMCSF-F1/R1 will amplify a 310 bp DNA fragment from VC-TK⁻-mGM-CSF virus, while hFlt3L-F1/R1 will generate a 316 bp PCR fragment from VC-TK⁻-hFlt3L virus. Primer sequence: TK-F2 (SEQ ID NO:1): TGTGAAGAC-GATAAATTAATGATC; TK-F4 (SEQ ID NO:2): TTGT-CATCATGAACGGCGGA;
TK-R4 (SEQ ID NO:3): TCCTTCGTTTGCCATACGCT;
TK-F5 (SEQ ID NO:4): GAACGGGACTATGGACGCAT;
TK-R5 (SEQ ID NO:5): TCGGTTTCCTCACCCAATCG;
pCB-R3 (SEQ ID NO:6): ACCTGATGGA-TAAAAGGCG;
mGMCSF-F1 (SEQ ID NO:7): GGCATTGTGGTCTACA-GCCT;
mGMCSF-R1 (SEQ ID NO:8): GTGTTTCACAGTC-CGTTTCCG;
hFlt3L-F1 (SEQ ID NO:9): AACGACCTATCTCCTC-CTGC;
hFlt3L-R1 (SEQ ID NO:10): GGGCTGAAAGGCA-CATTTGG.

Example 3

Figure 4A:
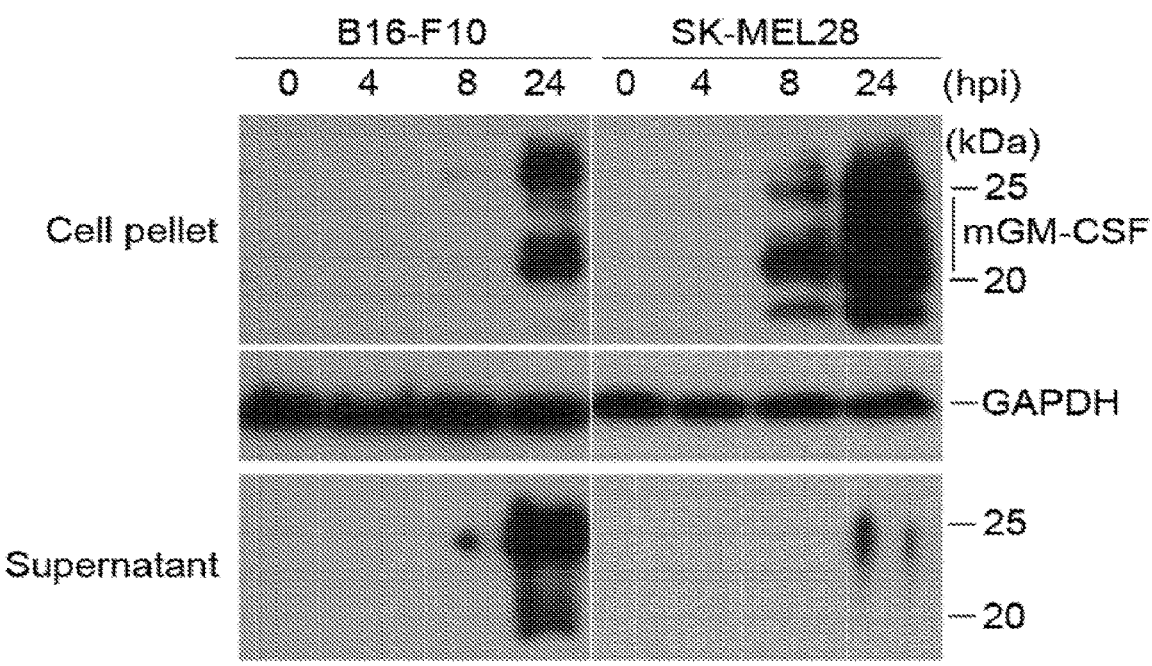
FIG. 4A-B show Western blot results.

Expression of mGM-CSF from Melanoma Cells Infected with Recombinant VC-TK-mGM-CSF Virus To test the expression of mGM-CSF from the VC-TK⁻ recombinant viruses, the inventors infected B16 murine melanoma cells and human melanoma cells (SK-mel-28) with VC-TK⁻-mGM-CSF. Cell lysates and supernatants were collected at various times (4, 8, and 24 hours) post infection. Western blot analyses were performed to determine the levels of expression of the transgenes. As shown in FIG. 4A, the inventors observed abundant levels of mGM-CSF in both the cell lysates and supernatants.

Example 4

Figure 4B:
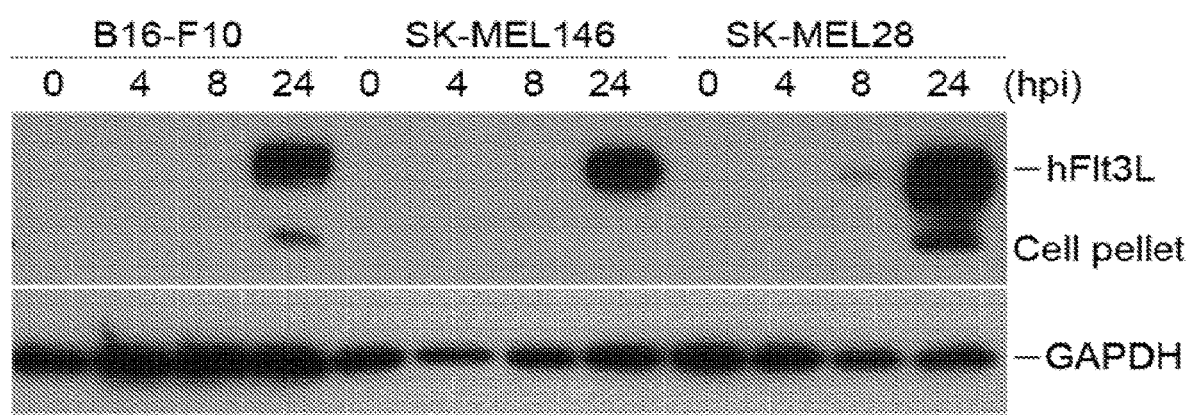

Expression of hFlt3L from Melanoma Cells Infected with Recombinant VC-TK-hFlt3L Virus To test the expression of hFlt3L from the VC-TK⁻ recombinant viruses, the inventors infected B16 murine melanoma cells and human melanoma cell lines with VC-TK⁻nFlt3L. Cell lysates and supernatants were collected at various times post infection (4, 8, and 24 hours). Western blot analysis was performed to determine the levels of expression of the transgenes. The inventors detected abundant levels of hFlt3L in the cell lysates but not in supernatants (FIG. 4B). This is consistent with the notion that hFlt3L is mostly associated with membranes and is not secreted.

Example 5

VC-TK, VC-TK⁻-mGM-CSF and VC-TK⁻-hFlt3L are Replication Competent

The replication capacities of VC, VC-TK⁻, VC-TK⁻-mGM-CSF, and VC-TK⁻-hFlt3L in murine B16-F10 cells were determined by infecting them at a MOI of 0.01. Cells were collected at various times post-infection (24, 48, and 72 hours) and viral yields (log pfu) were determined by titration on BSC40 cells. VC replicated efficiently in B16-F10 cells with viral titers increasing by 20,000-fold at 72h post-infection. (FIGS. 5A and 5B). Deletion of TK gene resulted in the 3-fold decrease in viral replication in B16 melanoma cells compared with VC. In addition, E3LΔ83N-TK⁻-mGM-CSF and E3LΔ83N-TK⁻-hFlt3L were also replication competent in murine B16 cells, with an increase of viral titers by 2800-fold and 1000-fold at 72 h post infection, respectively (FIGS. 6A and 6B). Thus, in this Example, the inventors have shown that VC-TK⁻, VC-TK⁻-mGM-CSF and VC-TK⁻-hFlt3L are all replication competent in tumor cells.

Example 6

Figure 6:
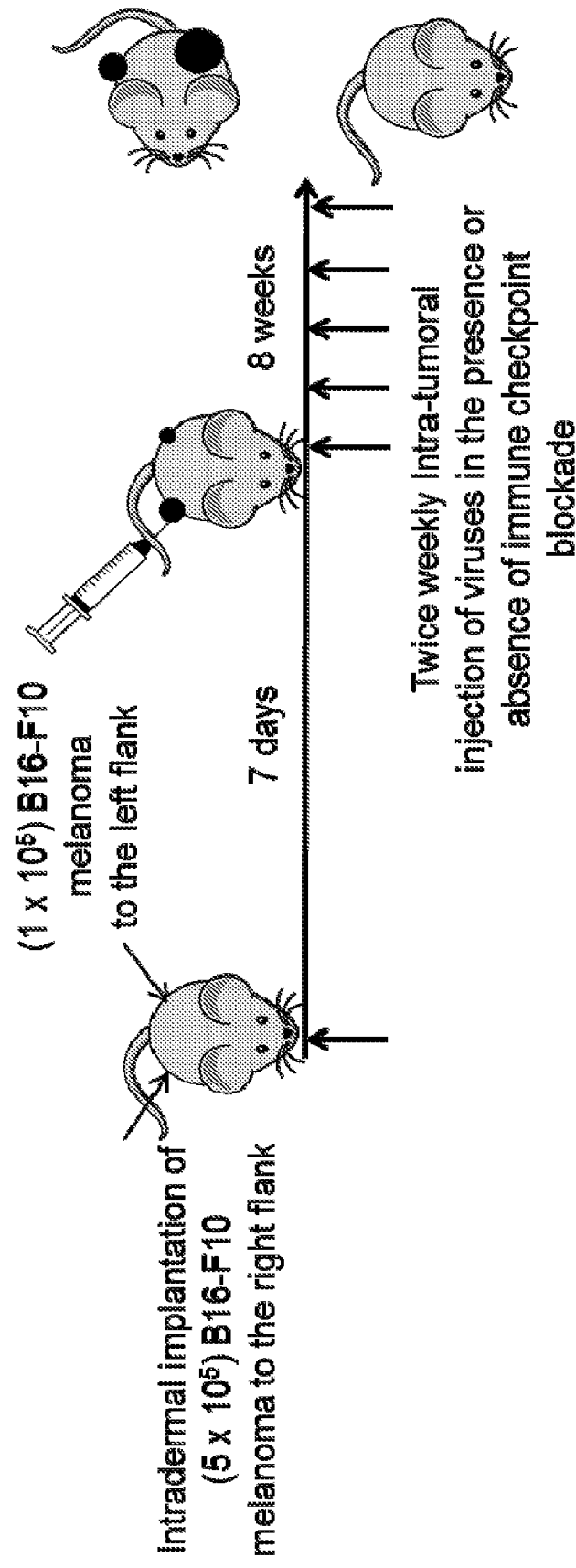
FIG. 6 is a scheme of treatment plan in which B16-F10 melanomas were treated with intratumoral injection of viruses in the presence or absence of immune checkpoint blockade. Briefly, B16-F10 melanoma cells were implanted intradermally to left and right flanks of C57B/6 mice ($5 \times 10^5$ cells to the right flank and $1 \times 10^5$ cells to the left flank). 7 days post tumor implantation, the mice were treated with intratumoral injections of viruses twice a week with or without intraperitoneal delivery of immune checkpoint blockade antibodies. We measured tumor sizes and monitored survival in the next 8 weeks.
Figures 7A, 7C:
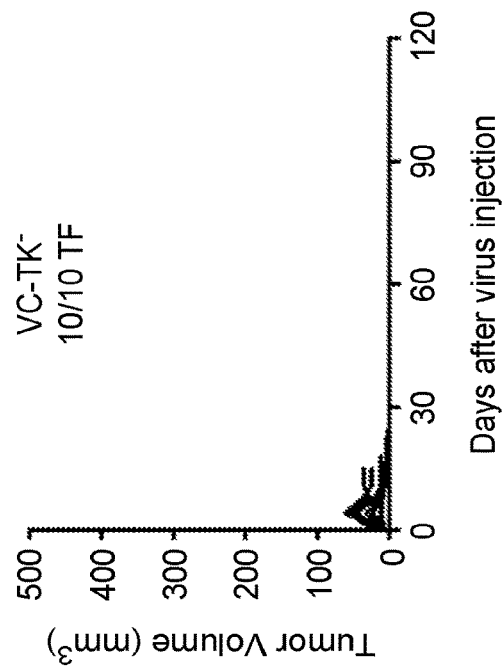
Figure 7B:
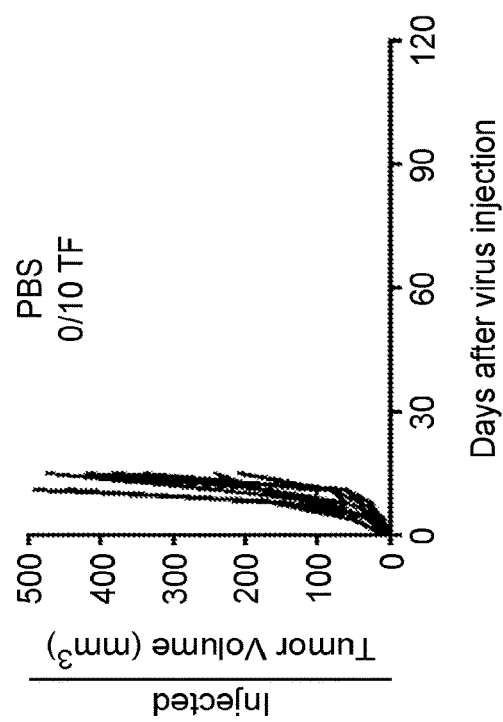

Intratumoral Injection of VC-TK, VC-TK⁻-mGM-CSF, or VC-TK⁻-hFlt3L Leads to Eradication of Injected Tumors and Delayed Tumor Growth at the Contralateral Non-Injected Tumors To test the in vivo tumor killing activities of the recombinant viruses and vector control, murine B16 melanoma cells were implanted to C57B/6 mice, with 1×10$^5$ cells to the left flank and 5×10$^5$ cells to the right flank. The inventors performed intratumoral injection of VC-TK$^-$, VC-TK$^-$-mGM-CSF, or VC-TK$^-$-hFlt3L (2×10$^7$ pfu) twice weekly to the larger tumor (about 3-4 mm in diameter) on the right flank. PBS mock-treatment control was included in the study. Bilateral tumor sizes were measured twice a week and mice were monitored for survival. When the tumor sizes reached 1 cm in diameter, the mice were euthanized. The experimental scheme is shown in FIG. 6. The inventors observed that the PBS mock-treated tumors grew very quickly and mice died with a medium survival of 15 days (FIG. 7A, B). 10/10 of the E3LΔ83N-TK$^-$-injected tumors regressed (FIG. 7C).

Figure 7D:
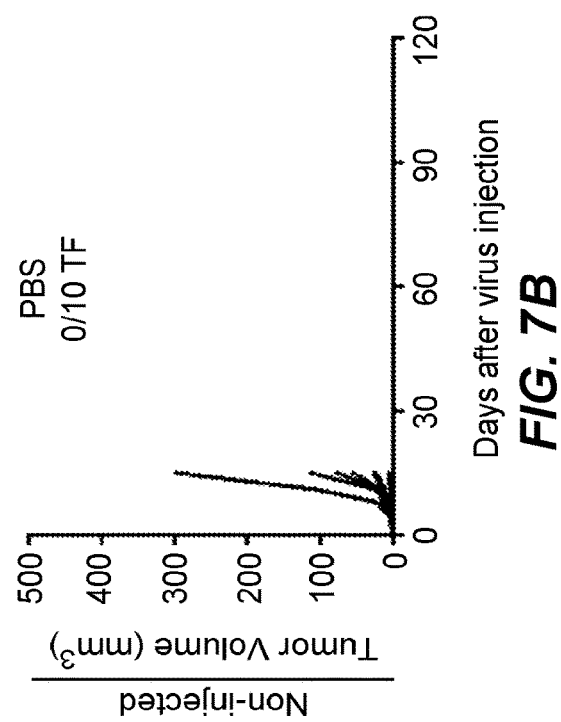
Figure 7E:
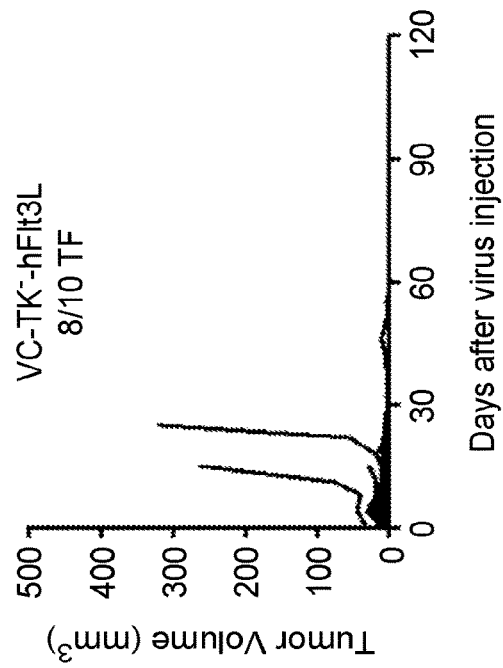
Figure 7G:
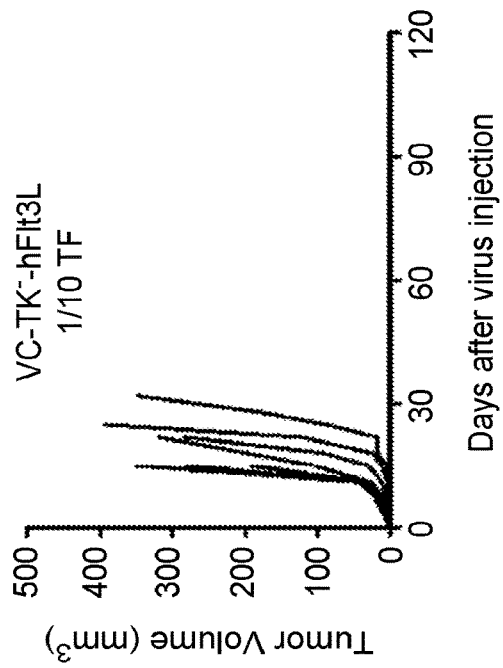
Figure 7F:
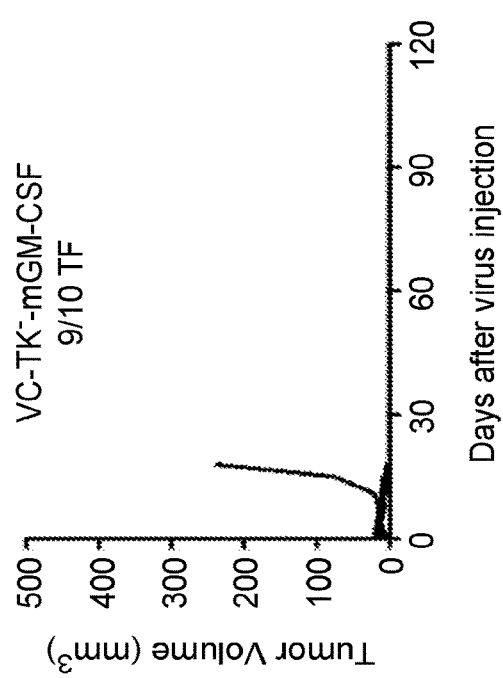
Figure 7H:
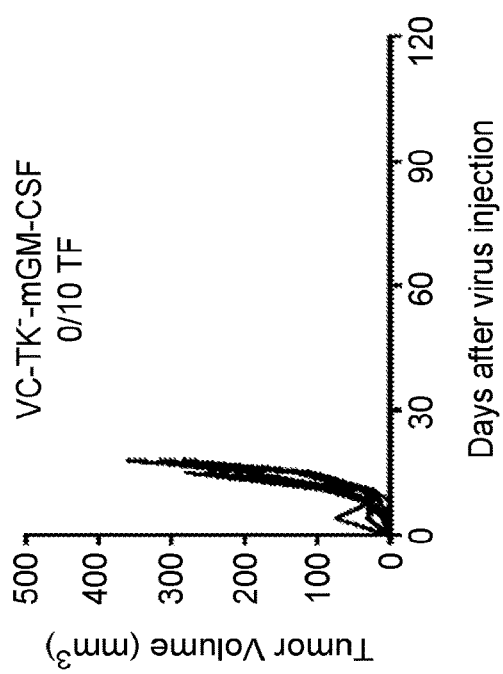
Figure 7M:
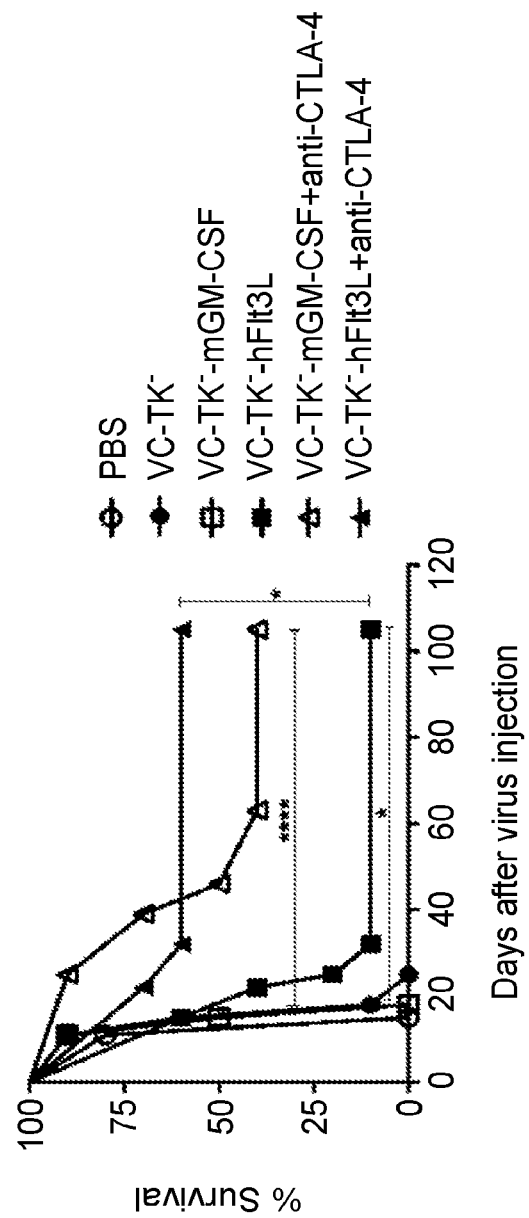
(FIG. 7M) Kaplan-Meier survival curve of mice treated with PBS, VC-TK$^-$, VC-TK$^-$-mGM-CSF, VC-TK$^-$-hFlt3L, VC-TK$^-$-mGM-CSF+anti-CTLA-4, or VC-TK$^-$-hFlt3L+anti-CTLA-4. Survival data were analyzed by log-rank (Mantel-Cox) test. *, P<0.05; ****, P<0.0001.

However, the contralateral tumors continued to grow (FIG. 7D) and all of the mice died with a median survival of 18 days (P<0.05, compared with PBS-treated group) (FIG. 7M). The addition of mGM-CSF to the VC-TK$^-$ vector did not result in prolonged survival compared with VC-TK$^-$ vector (FIG. 7M). However, intratumoral injection of VC-TK$^-$-hFlt3L not only eradicated 8/10 injected tumors but also resulted in delayed tumor growth in the contralateral tumors and extended medium survival to 22 days (P<0.01, compared with PBS-treated group; P=0.02, compared with VC-TK$^-$-mGM-CSF-treated group) (FIG. 7E, F, M). These results demonstrate that although intratumor injection of attenuated replication competent VC-TK$^-$, VC-TK$^-$-mGM-CSF, or VC-TK$^-$-hFlt3L can effectively eradicate injected tumors, intratumoral delivery of VC-TK$^-$-hFlt3L is more efficacious than VC-TK$^-$-mGM-CSF in delaying the growth of contralateral tumor and extending survival.

Example 7

The Combination of Intratumoral Delivery of Recombinant VC-TK$^-$-mGM-CSF, or VC-TK$^-$-hFlt3L with Systemic Delivery of Immune Checkpoint Blocking Agent Leads to More Efficient Tumor Eradication and Longer Survival than Either Treatment Alone It has been shown that systemic delivery of anti-CTLA-4 antibody is incapable of controlling B16 melanoma growth. To test whether intratumoral delivery of oncolytic viruses would overcome the resistance to immune checkpoint blocking agents, the inventors used murine B16 bilateral tumor implantation model in which the larger tumors on the right flank of the mice were injected twice weekly with either VC-TK$^-$-mGM-CSF, or VC-TK$^-$-hFlt3L with or without intraperitoneal delivery of anti-CTLA-4 antibody. Tumor sizes were measured twice weekly and the survival of mice was monitored. The inventors found that the combination of intratumoral delivery of either VC-TK$^-$-mGM-CSF, or VC-TK-hFlt3L with systemic delivery of anti-CTLA-4 antibody lead to the eradication of 10/10 injected tumors, and significant delay of the growth of contralateral non-injected tumors, as well as complete eradication of tumors in 40-60% of the cases (FIG. 7I-M). Similarly to the results observed in Example 6, intratumoral delivery of VC-TK$^-$-hFlt3L in combination with anti-CTLA-4 antibody was more efficacious than VC-TK$^-$-mGM-CSF in combination with anti-CTLA-4 antibody in delaying the growth of contralateral tumor and extending survival of treated mice. Taken together, these results indicate that intratumoral delivery of attenuated replication competent oncolytic viruses can induce antitumor immunity, which is amplified in the presence of anti-CTLA-4 antibody.

Example 8

Intratumoral Delivery of Heat-Inactivated VC-TK$^-$-mGM-CSF is More Efficacious in Eradiating Tumors and Generating Antitumoral Adaptive Immunity than Live VC-TK$^-$-mGM-CSF The inventors previously reported that Heat-inactivated MVA is more efficacious than MVA in eradicating injected tumors and inhibiting or delaying the growth of non-injected distant tumors in a bilateral B16-F10 bilateral tumor implantation model (See International Application PCT/US2016/19663 filed by the inventors and co-workers on Feb. 25, 2016; and provisional application No. 62/149,484 filed on Apr. 17, 2015 and its corresponding international application, PCT/US2016/028184 filed Apr. 18, 2016. These applications are herein incorporated by reference in their entirety). Because most of oncolytic viruses in clinical trials, including T-VEC, which has been approved for the treatment of metastatic melanoma, are replication competent, the inventors performed a head-to-head comparison between VC-TK$^-$-mGM-CSF and Heat-inactivated VC-TK$^-$-mGM-CSF in a bilateral B16-F10 implantation model. VC-TK$^-$-mGM-CSF is similar to JX594 in that it has TK deletion and GM-CSF transgene. Although VC-TK-mGM-CSF replicates efficiently in B16 melanoma cells, it is more attenuated than WT vaccinia in animals and possibly in humans due to the deletion of the Z-DNA-binding domain of E3 (Brandt and Jacobs, JVI, 2001). Therefore, it is anticipated that VC-TK-mGM-CSF will be safer than JX594 for human use. The inventors hypothesized that, similar to Heat-MVA, Heat-VC-TK$^-$-mGM-CSF would be a stronger activator of antitumor immunity than live VC-TK$^-$-mGM-CSF due to its ability to induce type I IFN in DCs and cancer cells. To test that, the inventors performed the following experiment. Briefly, B16-F10 melanoma cells were implanted intradermally to the left and right flanks of C57B/6 mice (5×10$^5$ to the right flank and 1×10$^5$ to the left flank). 7 days after tumor implantation, 2×10$^7$ pfu of live VC-TK$^-$-mGM-CSF or an equivalent amount of Heat-VC-TK$^-$-mGM-CSF was intratumorally injected to the larger tumors on the right flank. The tumor sizes were measured and the tumors were injected twice a week. Mouse survival was monitored. It was found that in mice treated with PBS, tumors grow rapidly at the right flank, which resulted in early death (FIG. 8 A, B, O). Intratumoral injection of either Heat-VC-TK$^-$-mGM-CSF or live VC-TK$^-$-mGM-CSF resulted in delaying of tumor growth and improved survival compared with PBS (FIG. 8O, *, P<0.001 for VC-TK$^-$-mGM-CSF vs. PBS, **, P<0.0001 for Heat-VC-TK$^-$-mGM-CSF vs. PBS). Intratumoral injection of Heat-VC-TK$^-$-mGM-CSF is more efficacious than VC-TK$^-$-mGM-CSF in eradicating injected tumors (8/9 tumor free for Heat-VC-TK$^-$-mGM-CSF vs. 4/9 tumor free for VC-TK$^-$-mGM-CSF) and delaying or inhibiting the growth of non-injected tumors at the contralateral side (7/9 tumor free for Heat-VC-TK$^-$-mGM-CSF vs. 5/9 tumor free for VC-TK$^-$-mGM-CSF) (FIG. 8C-F). The inventors observed improved survival in Heat-VC-TK$^-$-mGM-CSF-treated mice compared with VC-TK$^-$-mGM-CSF-treated mice (FIG. 8O, *, P=0.014). These results indicate that viral replication is not necessary for achieving antitumor effects. While, in this specific example, the inventors used heat inactivation to inactivate the virus, inactivation can be done by other methods. For example, another method of virus inactivation comprises use of ultraviolet irradiation.

Intratumoral injection of Heat-VC-TK$^-$-mGM-CSF leads to antitumor immunity possibly through the induction of STING-mediated type I IFN responses, activation of Batf3-dependent dendritic cells (DC) and recruitment and activation of anti-tumor CD8$^+$ and CD4$^+$ T cells, as well as increase of ratios of CD8$^+$/Treg and CD4$^+$ effector/Treg as the inventors of the present disclosure have demonstrated for Heat-MVA.

Figure 8E:
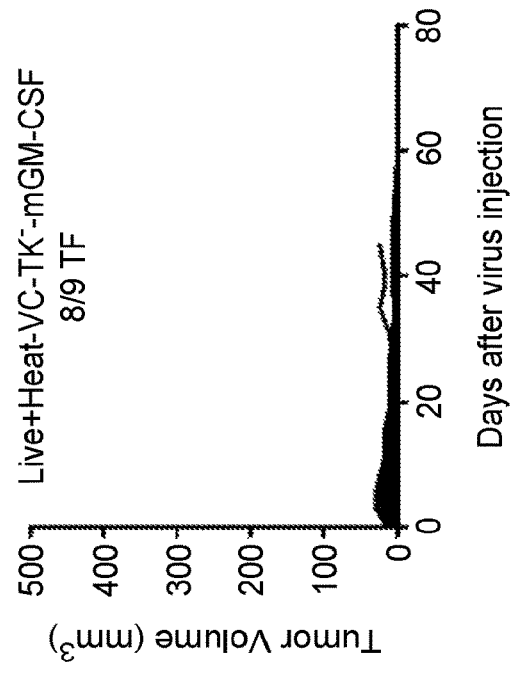
(FIG. 8E, F) are graphs showing the volume of injected tumors (FIG. 8E) and non-injected tumors (FIG. 8F) at various days post injection with Heat-inactivated VC-TK$^-$-mGM-CSF (n=9).
Figure 8G:
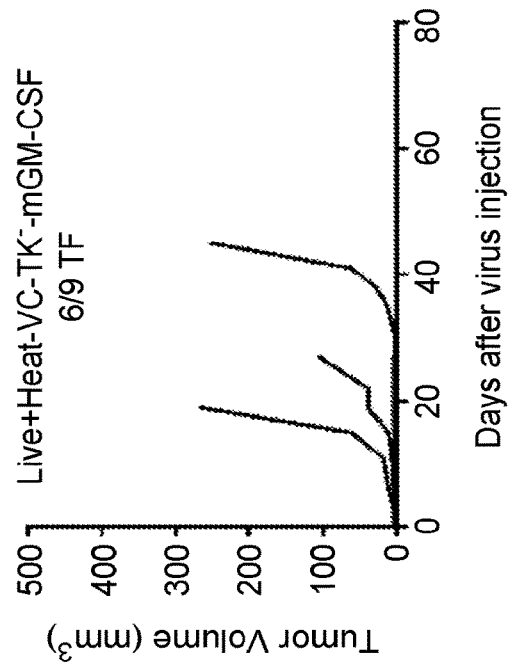
FIG. 8G, H are graphs showing the volume of injected tumors (FIG. 8G) and non-injected tumors (FIG. 8H) at various days post injection with live+Heat-inactivated VC-TK$^-$-mGM-CSF (n=9).
Figure 8F:
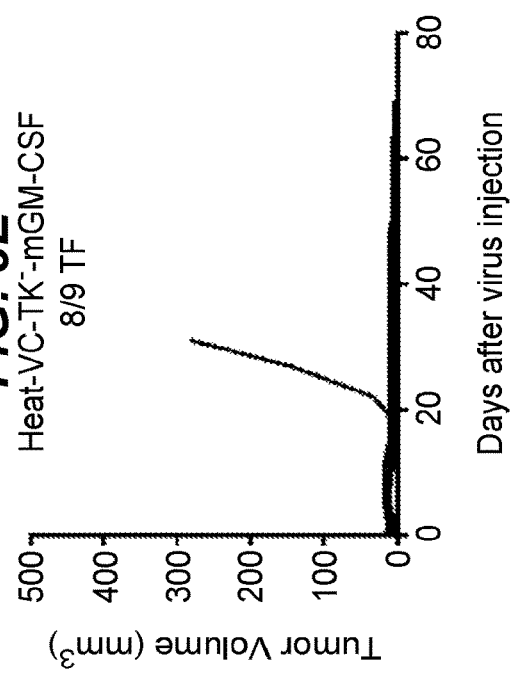
Figure 8H:
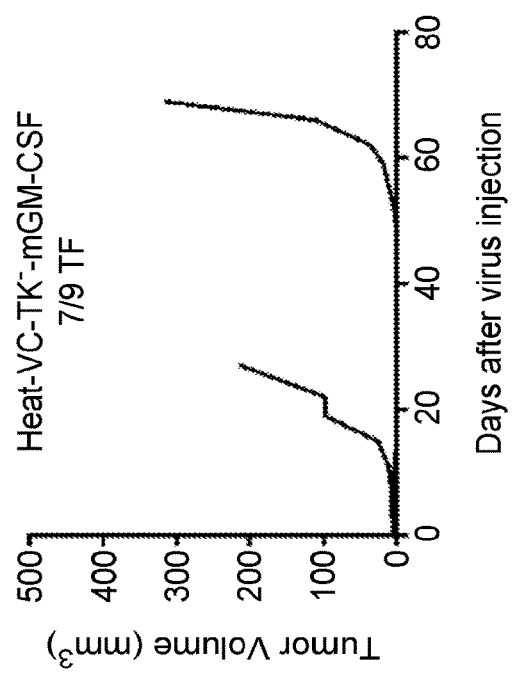
Figure 8O:
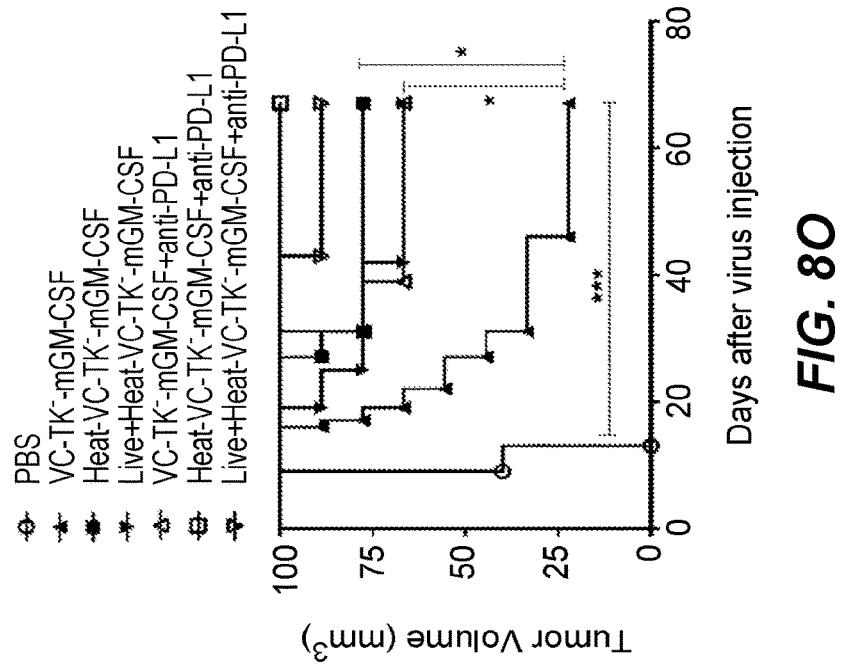
Figure 8M:
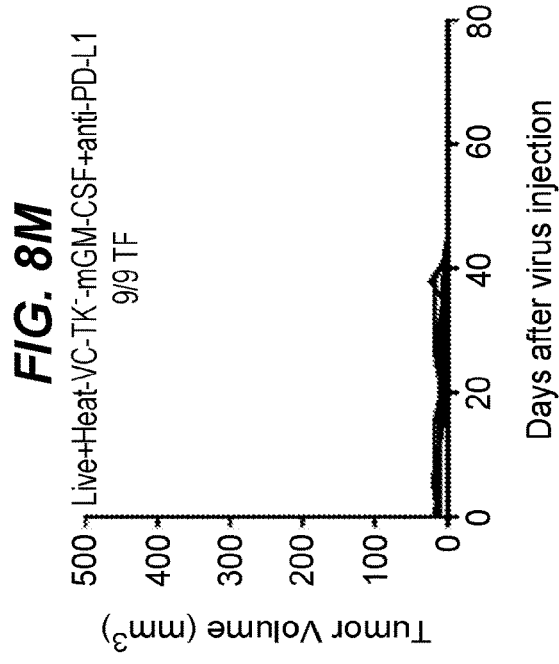
Figure 8N:
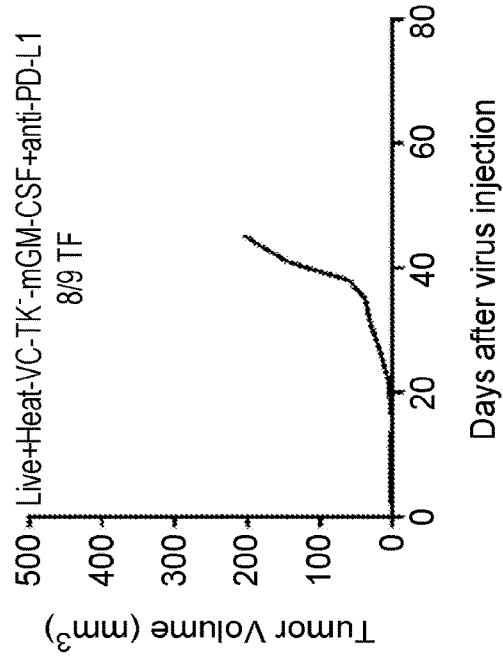

The co-administration of live and Heat-VC-TK$^-$-mGM-CSF into tumors did not result in improved antitumor responses compared to Heat-VC-TK$^-$-mGM-CSF alone (FIG. 8G, H, O). The inventors reasoned that the live virus might block the host's immune responses and therefore activities of the Heat-VC-TK$^-$-mGM-CSF, which may mitigate the beneficial effects of GM-CSF. Studies are ongoing to evaluate whether the co-administration of live and Heat-VC-TK$^-$-hFlt3L might be more efficacious than Heat-VC-TK$^-$-hFlt3L alone. Studies are also ongoing to further attenuate replication competent VC-TK$^-$-hFlt3L through deletion of candidate genes that interfere with the cytosolic DNA-sensing pathway.

Example 9

The Combination of Intratumoral Injection of VC-TK$^-$-mGM-CSF or Heat-Inactivated VC-TK$^-$-mGM-CSF with Intraperitoneal Delivery of Immune Checkpoint Blocking Agent Leads to Synergistic Therapeutic Effects The inventors next investigated whether intratumoral injection of live or Heat-inactivated VC-TK$^-$-mGM-CSF enhances therapeutic effects of anti-PD-L1 antibody in a bilateral B16-F10 melanoma model, which simulates an individual with metastatic disease. Briefly, B16-F10 melanoma cells were implanted intradermally to the left and right flanks of C57B/6 mice ($5 \times 10^5$ to the right flank and $1 \times 10^5$ to the left flank). 8 days after tumor implantation, the inventors intratumorally injected VC-TK$^-$-mGM-CSF ($2 \times 10^7$ pfu), or an equivalent amount of Heat-inactivated VC-TK$^-$-mGM-CSF, or the combination of live ($1 \times 10^7$ pfu) and Heat-VC-TK$^-$-mGM-CSF (an equivalent of $1 \times 10^7$ pfu) to the larger tumors on the right flank twice weekly, with intraperitoneal delivery of either isotype control, or with anti-PD-L1 antibody (200 μg per mouse) twice weekly.

The combination of intratumoral injection of live VC-TK$^-$-mGM-CSF and systemic delivery of anti-PD-L1 antibody resulted in a significant improvement of mouse survival (FIG. 8O, *, P=0.02 for VC-TK$^-$-mGM-CSF+anti-PD-L1 vs. VC-TK$^-$-mGM-CSF). 67% of the mice (6/9) treated with live VC-TK$^-$-mGM-CSF+anti-PD-L1 antibody were tumor free, whereas only 22% of the mice (2/9) treated with live VC-TK$^-$-mGM-CSF were tumor free at the end of the experiment (FIG. 8O). All of the mice (9/9) treated with Heat-VC-TK$^-$-mGM-CSF+anti-PD-L1, 89% of mice (8/9) treated live+Heat-VC-TK$^-$-mGM-CSF+anti-PD-L1 are alive at the end of experiment (day 67 post virus injection) (FIG. 8O). These results further demonstrated that, in the combination therapy setting, Heat-VC-TK$^-$-mGM-CSF or live VC-TK$^-$-mGM-CSF-induced antitumor immunity can be further amplified in the presence of anti-PD-L1 antibody.

Example 10

Figure 9:
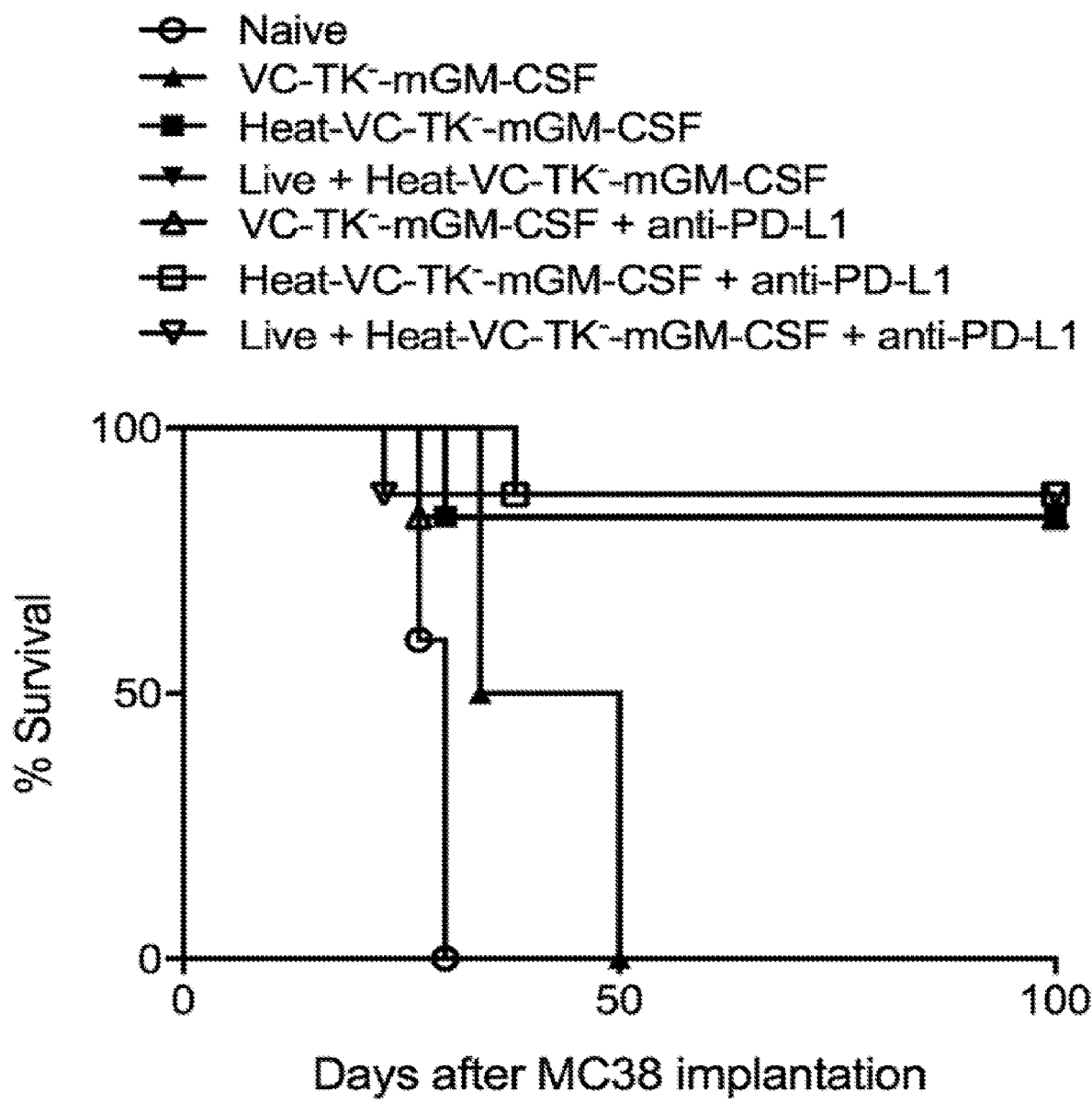
FIG. 9 shows a Kaplan-Meier survival curve of mice after tumor rechallenge with heterologous tumor MC38. These mice had initially treated with the following regimen for B16-F10 melanoma and surved. These agents include live VC-TK⁻-mGM-CSF, Heat-inactivated VC-TK⁻-mGM-CSF, live+Heat-inactivated VC-TK⁻-mGM-CSF, VC-TK⁻-mGM-CSF+anti-PD-L1, Heat-inactivated VC-TK⁻-mGM-CSF+anti-PD-L1, or live+Heat-inactivated VC-TK⁻-mGM-CSF+anti-PD-L1 antibody. A group of naïve mice that have never been exposed either to viruses or tumors were used as controls. MC38 ($1\times10^5$ cells) were implanted intradermally. Tumor growth and mice survival were monitored closely.

The Surviving Mice Treated with Heat-Inactivated VC-TK-mGM-CSF with or without Anti-PD-L1, or Treated with Live VC-VC-TK-mGM-CSF with Anti-PD-L1 have Developed Cross-Protective Immunity Against a Heterologous Tumor The inventors next tested whether the surviving mice that are successfully treated with viruses with or without anti-PD-L1 antibody for initial B16-F10 tumor have development cross-protective immunity against a heterologous tumor, in this case, MC38 colon carcinoma cells. This experiment included the following groups of mice: (i) surviving mice treated with live VC-TK$^-$-mGM-CSF (n=2), (ii) surviving mice treated with live VC-TK$^-$-mGM-CSF+anti-PD-L1 (n=6), (iii) surviving mice treated with Heat-VC-TK$^-$-mGM-CSF (n=7), (iv) surviving mice treated with Heat-VC-TK$^-$-mGM-CSF+anti-PD-L1 (n=9), (v) surviving mice treated with live+Heat-VC-TK$^-$-mGM-CSF+anti-PD-L1 (n=6), (vi) surviving mice treated with live+Heat-VC-TK$^-$-mGM-CSF+anti-PD-L1 (n=8), and (vii) nave mice that have never been exposed either to tumors or viruses (n=5). All of the mice were challenged with intradermal implantation of a lethal dose of MC38 ($1 \times 10^5$ cells) and the tumor sizes were measured twice weekly and the survival of the mice were monitored daily. The inventors observed that although all of the nave mice developed MC38 and die at expected time with a median survival of 30 days, 2/2 of the surviving mice treated with live VC-TK$^-$-mGM-CSF died at a later time with a median survival of 42 days (FIG. 9, p<0.05; VC-TK$^-$-mGM-CSF vs. nave mice). Surprisingly, the majority of the rest of surviving mice rejected MC38 challenge at 100 days post tumor implantation (FIG. 9). These results indicate that the surviving mice treated with Heat-VC-TK$^-$-mGM-CSF with or without anti-PD-L1 antibody have developed systemic immunity against a heterologous tumor. Such immunity is weaker in mice previously treated with live VC-TK$^-$-mGM-CSF, although only two mice were in this group. Future studies will expand the numbers of mice successfully treated with live VC-TK$^-$-mGM-CSF vs. Heat-VC-TK$^-$-mGM-CSF in an unilateral B16-F10 tumor implantation model and then assess cross-protective immunity against MC38, or another heterologous tumor such as MB49 bladder cancer.

Example 11

Figure 10A:
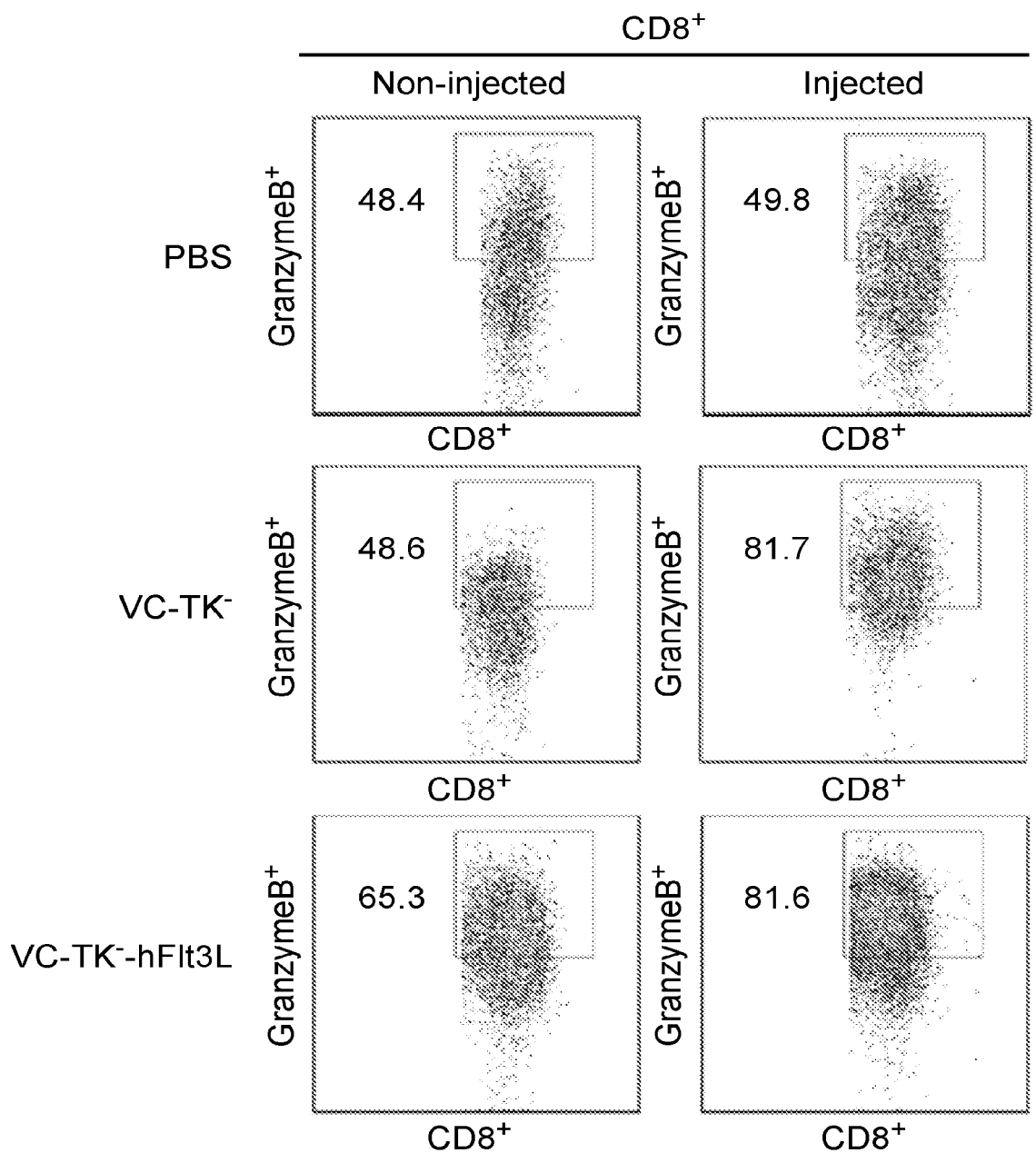

Intratumoral Injection of VC-TK$^-$-hFlt3L Virus is More Effective than VC-TK$^-$ Virus in the Proliferation and Activation of CD8$^+$ and CD4$^+$ T Cells in the Non-Injected Tumors To assess whether intratumoral injection of VC-TK$^-$ or VC-TK$^-$-hFlt3L in B16-F10 melanomas leads to activation and proliferation of CD8$^+$ and CD4$^+$ T cells, $2.5 \times 10^5$ B16-F10 melanoma cells were intradermally implanted to the left flank and $5 \times 10^5$ B16-F10 melanoma cells to the right flank of 6-8 weeks old C57B/6. 7 days post-implantation, VC-TK$^-$ or VC-TK$^-$-hFlt3L ($2 \times 10^7$ pfu) or PBS was injected into the larger tumors on the right flank. The injection was repeated three days later. Both the injected and non-injected tumors were harvested on day 7 after first injection, and cell suspensions were generated. The live immune cell infiltrates in the injected and non-injected tumors were analyzed by FACS. There was a dramatic increase in CD8$^+$ T cells expressing Granzyme B in the injected tumors, from 51% in PBS-treated tumors to 81% in VC-TK⁻-treated tumors and 83% in VC-TK⁻-hFlt3L-treated tumors (FIG. 10A, 10C, p<0.001; VC-TK⁻ or VC-TK⁻-hFlt3L vs. PBS). In the non-injected tumors, there was also as increase in CD8⁺ T cells expressing Granzyme B from 48% in PBS-treated mice to 54% in VC-TK⁻ treated and 70% in VC-TK⁻-hFlt3L-treated mice (FIG. 10A, 10C, p<0.05; VC-TK⁻-hFlt3L vs. PBS). These results indicate that intratumoral injection of either VC-TK⁻ or VC-TK⁻-hFlt3L led to increased activated CD8⁺ T cells in the injected tumors, and intratumoral injection of VC-TK⁻-hFlt3L but not VC-TK⁻ led to significantly increased activated CD8⁺ T cells in the non-injected tumors.

Figure 10B:
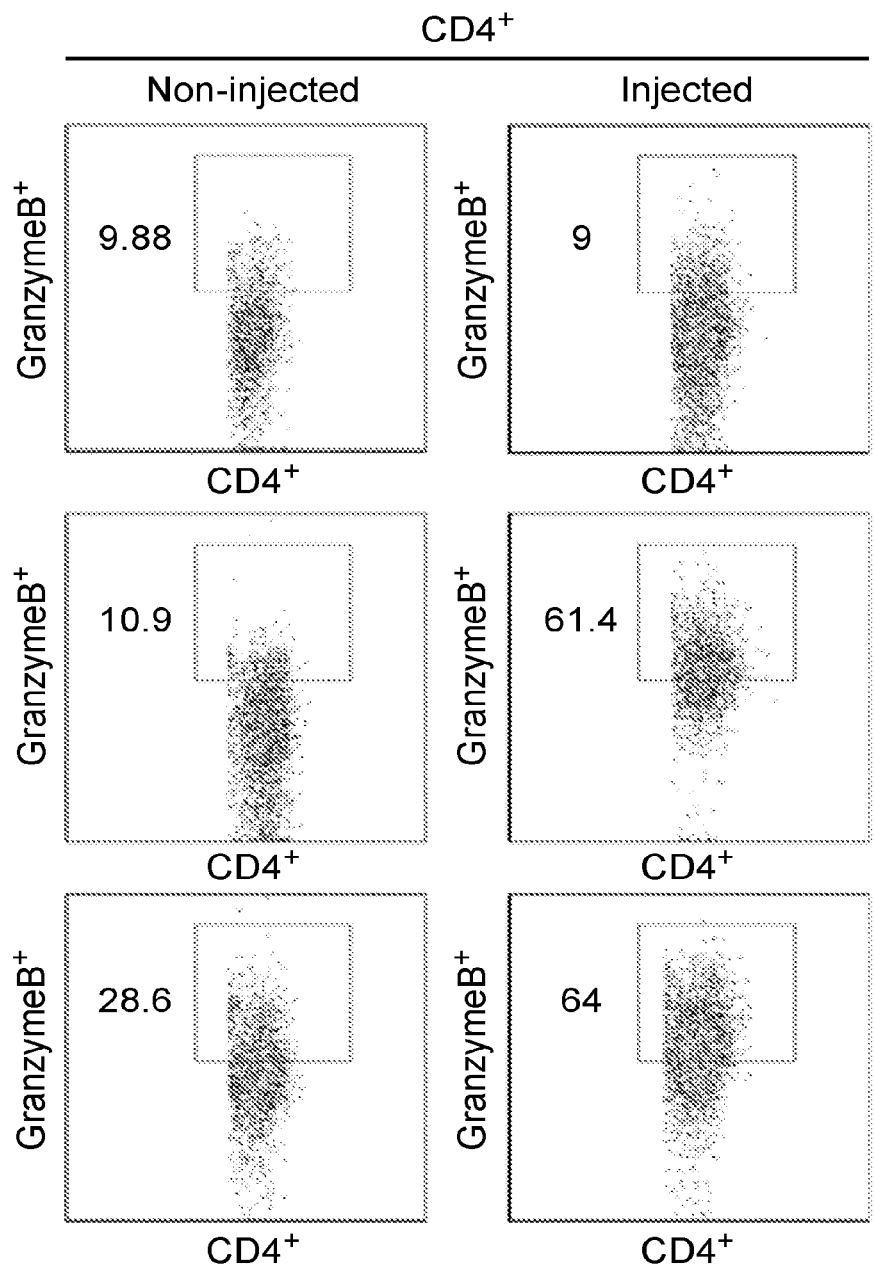

Similar changes were observed for CD4⁺ T cells in the injected and non-injected tumors from mice treated with either VC-TK⁻ or VC-TK⁻-hFlt3L compared with those treated with PBS. Granzyme B⁺CD4⁺ T cells rose from 9% in PBS-treated tumors to 74% in VC-TK⁻-treated tumors and 71% in VC-TK⁻-hFlt3L-treated tumors (FIG. 10B, 10D, p<0.001; VC-TK⁻ or VC-TK⁻-hFlt3L vs. PBS). In the non-injected tumors, there was also as increase in CD4⁺ T cells expressing Granzyme B from 11% in PBS-treated mice to 13% in VC-TK⁻-treated and 32% in VC-TK⁻-hFlt3L-treated mice (FIG. 10B, 10D, p<0.01; VC-TK⁻-hFlt3L vs. PBS). These results indicate that intratumoral injection of either VC-TK⁻ or VC-TK⁻-hFlt3L led to increased activated CD4⁺ T cells in the injected tumors, and intratumoral injection of VC-TK⁻-hFlt3L but not VC-TK⁻ led to increased activated CD4⁺ T cells in the non-injected tumors.

Example 12

Figure 11:
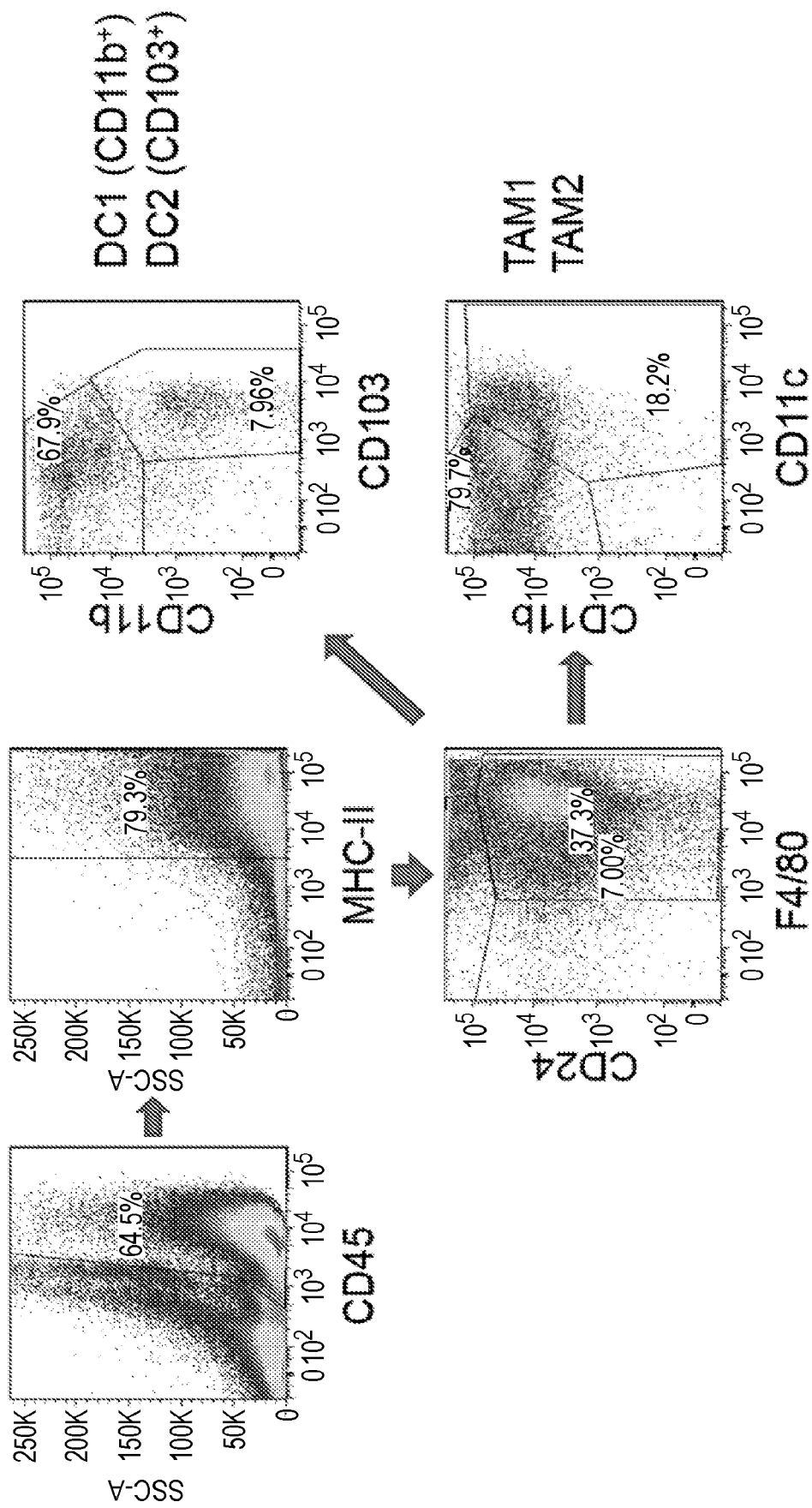
FIG. 11 is a gating strategy to separate $CD11b^+$ DCs from $CD103^+$ DCs in the tumor infiltrating $CD45^+MHCII^+$ cells. Tumor-associated $CD24^+$ DCs can be further separated by their expression of CD11b and CD103. $CD11b^+$ DCs (DC1) express a high level of CD11b, whereas $CD103^+$ DCs (DC2) express a high level of CD103. $F4/80^+$ tumor-associated macrophages can be further separated into TAM1 and TAM2 based on their relative expression of CD11c and CD11b.

Intratumoral Injection of VC-TK⁻-hFlt3L Results in the Increase of CD103⁺ Dendritic Cells in the Non-Injected Tumors The inventors next analyzed dendritic cell (DC) populations in both injected and non-injected tumors. Tumor infiltrating DCs are characterized as CD45⁺Ly6C-MHC-II+CD24$^{hi}$F4/80$^{lo}$ cells (Broz et al., Cancer Cell, 2014). Among the CD24$^{hi}$ DCs, there are two DC populations, CD11b⁺ DC (also known as DC1) and CD103⁺ DC (also known as DC2). FIG. 11 shows the gating strategy for these DC populations. CD45⁺ live cells were further separated based on the expression of MHC-II. The MHC-II$^{hi}$ cells were stained for DC marker CD24 and tumor-associated macrophage marker F4/80. CD24$^{hi}$F4/80$^{lo}$ cells were further separated into CD103⁺ DCs and CD11b⁺ DCs based on their expressions of CD103 and CD11b.

CD103+ DCs is a subset of peripheral DCs that are specialized in cross-presenting antigens. Batf3 is a transcription factor that is important for the differentiation of CD103+ DCs. CD103+ DCs play important roles in host anti-tumor immunity. The inventors of the present disclosure have previously shown that Batf3-dependent CD103⁺ DCs are required for inactivated MVA-mediated antitumor effects (WO2016/168862). Here, the inventors investigated the percentages of CD103⁺ DCs out of CD45+ cells in both injected and non-injected tumors.

B16-F10 melanoma cells ($2.5 \times 10^5$) were intradermally implanted to the left flank and $5 \times 10^5$ B16-F10 melanoma cells to the right flank of 6-8 weeks old C57B/6. 7 days post-implantation, Heat-MVA, VC-TK⁻, VC-TK⁻-mGM-CSF, or VC-TK⁻-hFlt3L ($2 \times 10^7$ pfu) or PBS was injected into the larger tumors on the right flank. The injection was repeated three days later. Both the injected and non-injected tumors were harvested on day 7 after first injection, and cell suspensions were generated. The live myeloid cell infiltrates in the injected and non-injected tumors were analyzed by FACS. The inventors observed that intratumoral injection of Heat-MVA, or VC-TK⁻, or VC-TK⁻-mGM-CSF, or VC-TK⁻-hFlt3L resulted in the reduction of percentages of CD103⁺ DCs out of CD45⁺ cells from 0.2% in PBS-mock treated tumors to 0.03%, 0.03%, 0.05%, and 0.12% in Heat-MVA, VC-TK⁻, VC-TK⁻-mGM-CSF, or VC-TK⁻-hFlt3L-treated tumors (FIG. 12A; P<0.05, Heat-MVA, or VC-TK⁻, or VC-TK⁻-mGM-CSF vs. PBS). In the non-injected tumors, intratumoral injection of Heat-MVA, or VC-TK⁻, or VC-TK⁻-mGM-CSF, or VC-TK⁻-hFlt3L resulted in the increase of percentages of CD103⁺ DCs out of CD45⁺ cells from 0.15% in PBS-mock treated mice to 0.32%, 0.26%, 0.21%, and 0.39% in Heat-MVA, VC-TK⁻, VC-TK⁻-mGM-CSF, or VC-TK⁻-hFlt3L-treated mice (FIG. 12A; P<0.05, VC-TK⁻-hFlt3L vs. PBS). These results indicate that CD103⁺ DCs undergo dynamic changes after intratumoral injection with viruses including decrease of percentages of CD103⁺ DCs out of CD45+ cells in the injected tumors, and intratumoral injection of VC-TK⁻-hFlt3L leads to the significant increase of percentages of CD103⁺ DCs out of CD45+ cells in the contralateral non-injected tumors. These results are consistent with the understanding that hFlt3L is an important growth factor for the differentiation and proliferation of CD103⁺ DCs.

Figures 12A, 12B:
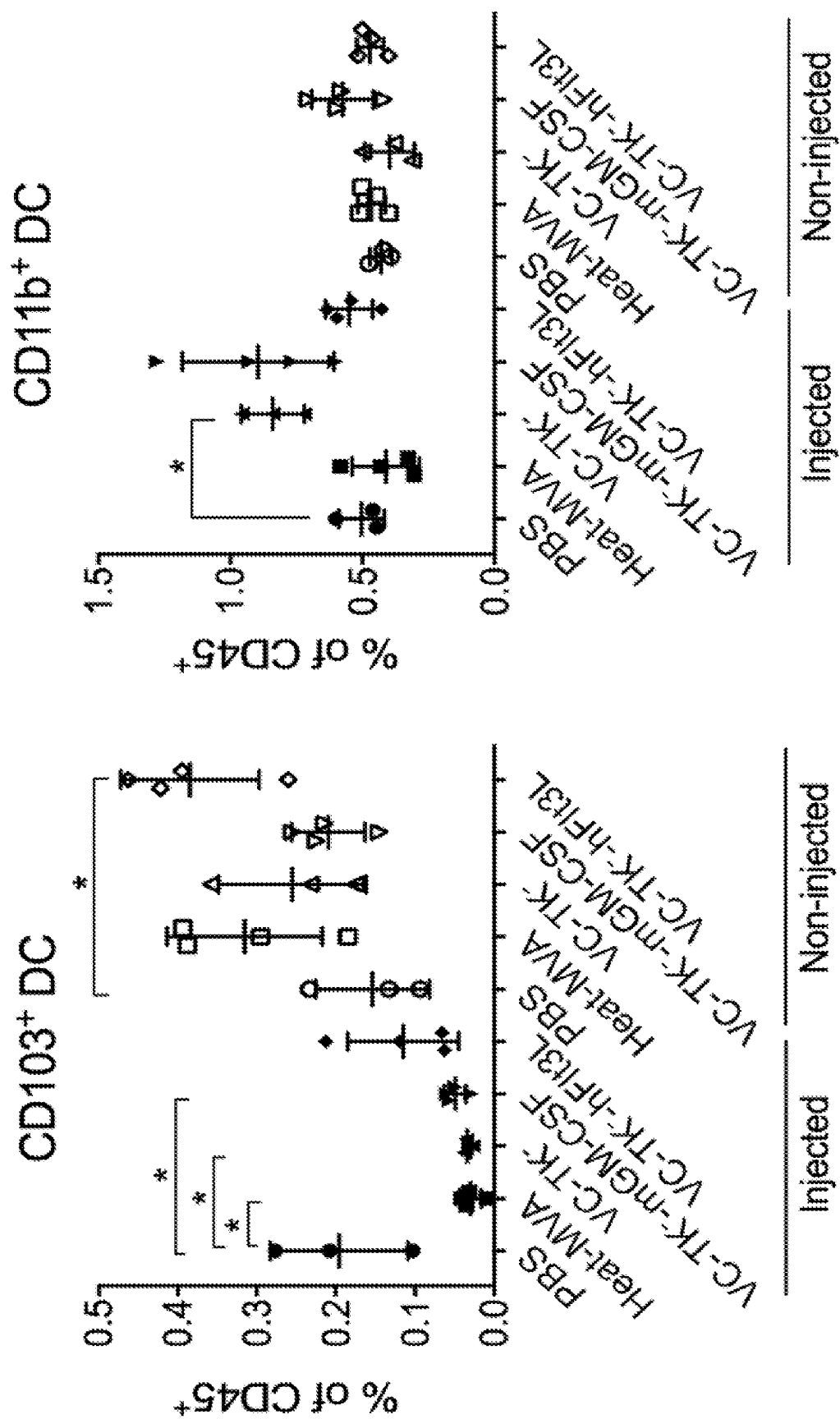
FIG. 12A-B is a series of graphical representations showing that intratumoral injection of VC-TK⁻-hFlt3L leads to the modest increase $CD103^+$ DCs in the non-injected tumors.
Figure 13A:
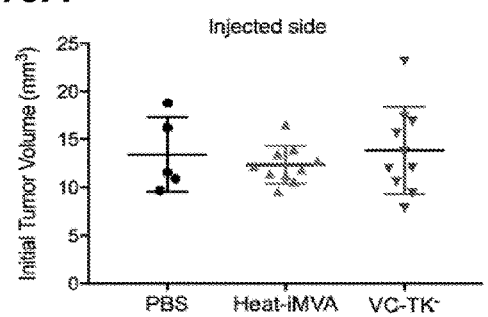
FIG. 13A-E shows a series of graphical representations of intratumoral injection of VC-TK or Heat-inactivated MVA in a 4T1 murine triple negative breast carcinoma (TNBC) bilateral implantation model. 4T1 cells ($2.5\times10^5$) were implanted intradermally into the shaved skin on the right flank, and ($5\times10^4$) cells were implanted to the left flank. At 5 days post implantation, the right side tumors (about 3 mm in diameter) were injected twice weekly with either PBS, VC-TK⁻ ($2\times10^7$ pfu), or with an equivalent amount of Heat-inactivated MVA.
Figure 13B:
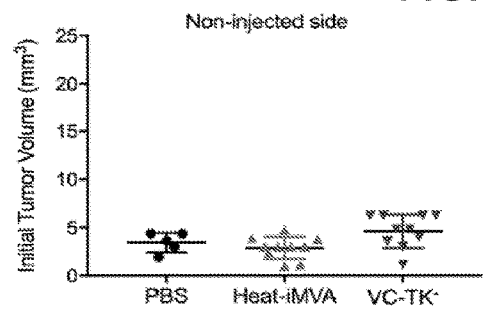
Figure 13C:
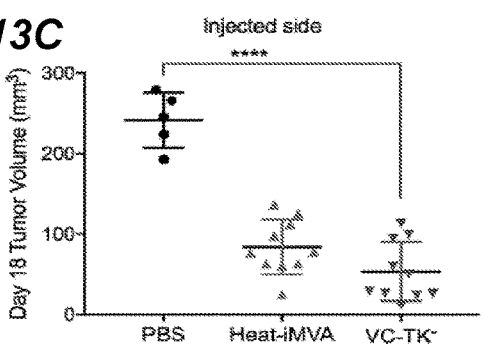
Figure 13D:
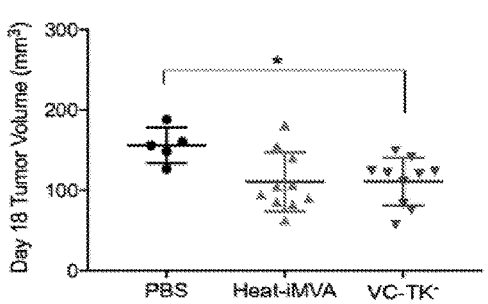
Figure 13E:
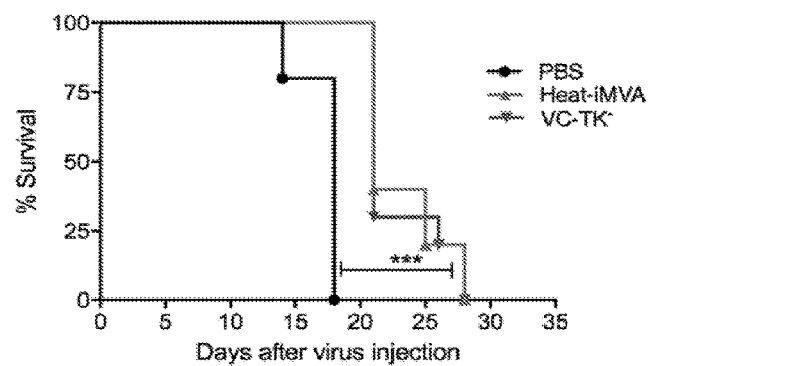
Figure 14A:
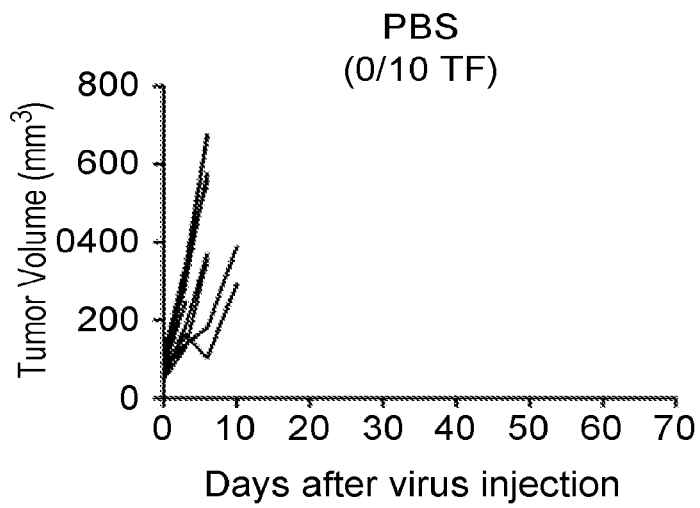
FIG. 14A-E shows a series of graphical representations of intratumoral delivery of VC-TK⁻-hFlt3L, Heat-inactivated MVA (Heat-iMVA) in an established large B16-F10 melanoma unilateral implantation model. B16-F10 cells ($5\times10^5$) were implanted intradermally to the right flank of C57B/6 mice. At 9 days post implantation, when the average initial tumor volumes reached 70 mm³, the tumors were injected with either VC-TK⁻-hFlt3L at 2×107 pfu or with an equivalent of Heat-iMVA twice weekly. PBS was used as a control.
Figure 14B:
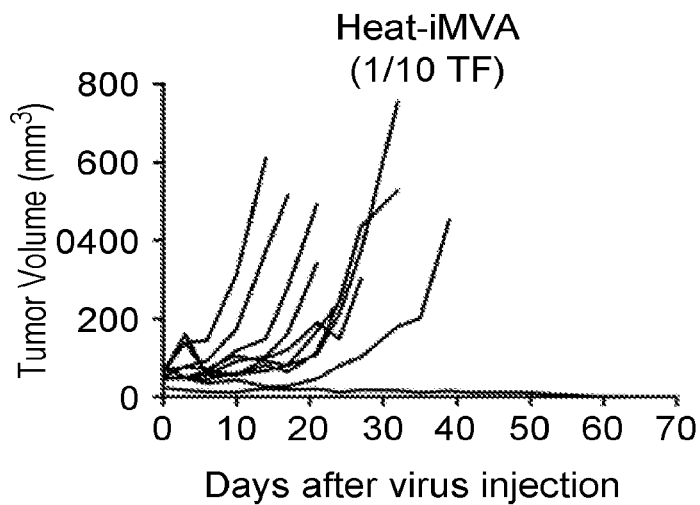
Figure 14C:
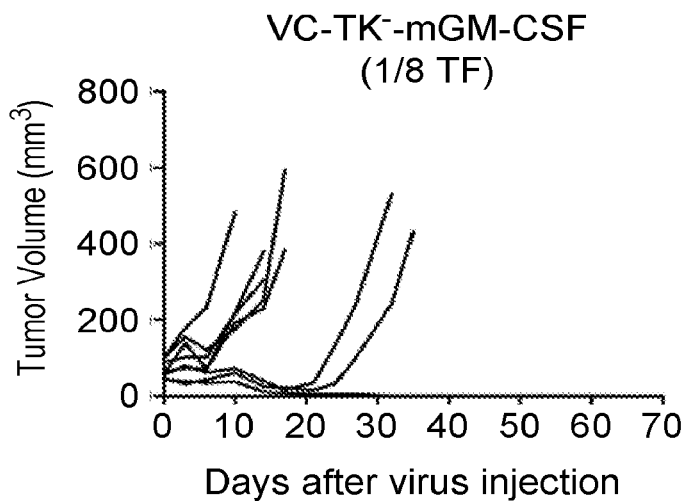
Figure 14D:
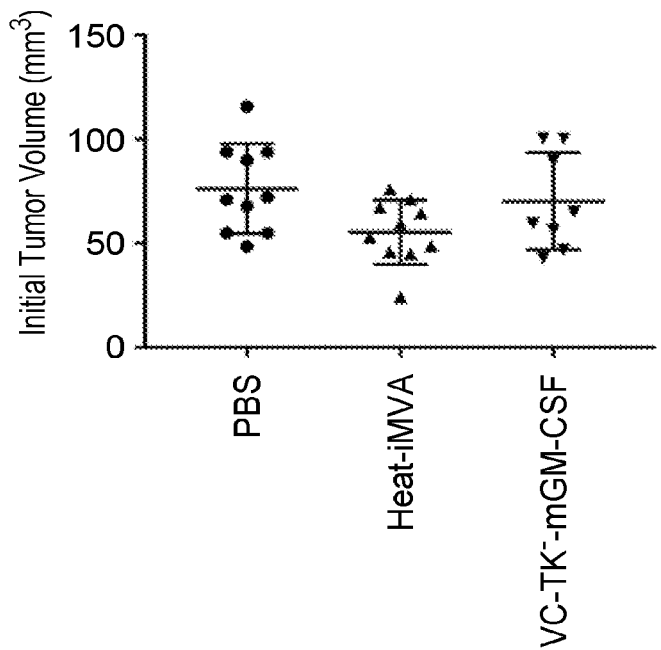
Figure 14E:
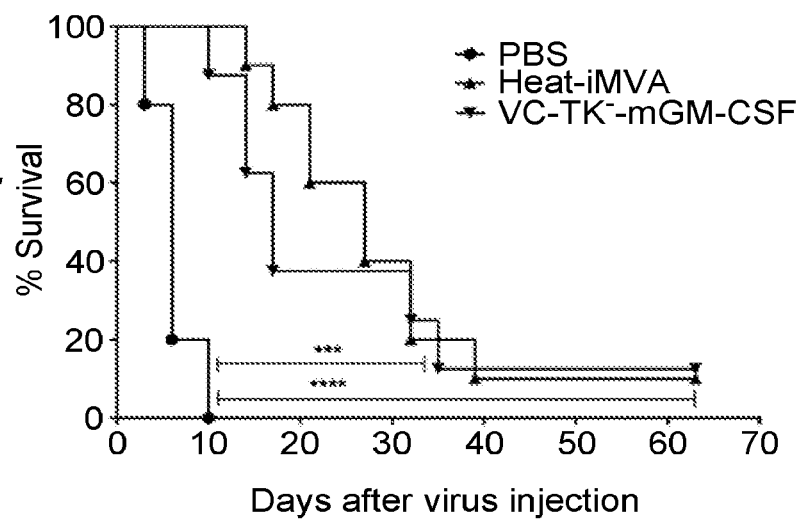

The percentages of CD11b⁺ DCs out of CD45⁺ cells in both injected and non-injected tumors were also investigated. It was found that intratumoral injection of VC-TK⁻ led to the increase of the percentages of CD11b⁺ DCs out of CD45⁺ cells from 0.5% in PBS-treated tumors to 0.8% in VC-TK⁻-treated tumors (FIG. 12B, P<0.05, VC-TK⁻ vs. PBS). Intratumoral injection of viruses does not seem to affect CD11b⁺ DC populations in the non-injected tumors (FIG. 12B). Taken together, these results indicate that intratumoral injection of VC-TK⁻-hFlt3L leads to the significant increase of percentages of CD103⁺ DCs out of CD45⁺ cells without affecting the percentages of CD11b⁺ DCs out of CD45⁺ cells in the contralateral non-injected tumors.

Example 13

Intratumoral Injection of VC-TK⁻ is Effective in a Bilateral Triple-Negative Breast Cancer 4T1 Tumor Implantation Model In addition to B16-F10 murine melanoma model, the inventors investigated whether intratumoral injection of oncolytic virus VC-TK– has efficacy in the treatment of triple-negative breast cancer (TNBC) 4T1 bilateral tumor implantation model. Briefly, 4T1 murine triple negative breast cancer (TNBC) cells were implanted intradermally to the left and right flanks of BALB/c mice ($2.5 \times 10^5$ to the right flank and $5 \times 10^4$ to the left flank). 5 days post tumor implantation, the larger tumors on the right flank were injected with either VC-TK⁻ virus ($2 \times 10^5$ pfu) or with an equivalent amount of Heat-inactivated MVA twice weekly. Mice were monitored daily and tumor sizes were measured twice a week. The survival of mice was monitored. The initial tumor volumes of the injected and non-injected tumors were shown (FIGS. 13 A and B). The tumor volumes of the injected and non-injected tumors at 18-day post treatment were shown (FIGS. 13 C and D). It was found that intratumoral injection of VC-TK⁻ led to dramatic decrease of tumor volumes of the injected tumors compared with PBS-treated tumors (FIG. 13C; P<0.0001, VC-TK⁻ vs. PBS) and also decrease of non-injected tumors volumes compared with PBS-treated mice (FIG. 13D; P<0.05, VC-TK⁻ vs. PBS). More importantly, the mean survival of mice was extended from 18 days in PBS-treated mice to 21 days in VC-TK⁻-treated mice (FIG. 13E; P=0.0001, VC-TK⁻ vs. PBS). The anti-tumor effect of VC-TK⁻ is similar to Heat-iMVA in this bilateral 4T1 tumor implantation model (FIG. 13, A-E). That is different from what we observed in B16-F10 bilateral tumor implantation model (FIGS. 8, C-F and O), in which VC-TK⁻-mGM-CSF is less effective than Heat-inactivated VC-TK⁻-mGM-CSF. These might be related to the differences in tumor subtypes and the populations of immune cells in the tumor microenvironment. Future studies will compare the efficacies of replication competent oncolytic virus with inactivated virus in other tumor models including prostate cancer and bladder cancer models. Because VC-TK⁻-hFlt3L is more effective than VC-TK⁻-mGM-CSF shown in Example 6 (FIG. 8 E-H, M), it is expected that intratumoral injection of oncolytic VC-TK⁻-hFlt3L would also be effective in treating 4T1 murine breast cancer.

Example 14

Intratumoral Injection of VC-TK⁻-mGM-CSF is Effective in a Large Established B16-F10 Unilateral Tumor Implantation Model The inventors compared the anti-tumor efficacy of intratumoral injection of replication competent VC-TK⁻-mGM-CSF with Heat-inactivated MVA (Heat-iMVA) in a large established B16-F10 unilateral tumor implantation model. In this experiment, B16-F10 melanoma ($5 \times 10^5$ cells in a volume of 50 μl) were implanted intradermally into the shaved skin on the right flank of WT C57BL/6J mice. After 9 days post implantation, tumor sizes were measured and tumors that are 5-6 mm in diameter were injected with Heat-iMVA (equivalent of $2 \times 10^7$ pfu of MVA in a volume of 50 μl) or with VC-TK⁻-mGM-CSF ($2 \times 10^7$ pfu), or with PBS twice weekly. Mice were monitored daily and tumor sizes were measured twice a week. Intratumoral injection of VC-TK⁻-mGM-CSF was efficacious in delaying tumor growth and even eradicating tumors in a small percentage of treated mice. It also extended the median survival from 6 days in PBS-treated mice to 17 days in VC-TK⁻-mGM-CSF-treated mice (FIG. 14, A, C-E, P<0.0001, VC-TK⁻-mGM-CSF vs. PBS). Intratumoral injection of Heat-iMVA in large established tumors were also effective and the median survival of Heat-iMVA-treated mice was extended to 27 days (FIGS. 14, B, D, and E). These results indicate that intratumoral injection of oncolytic VC-TK⁻-mGM-CSF is effective in treating large established B16-F10 in a unilateral implantation model. Because VC-TK⁻-hFlt3L is more effective than VC-TK⁻-mGM-CSF shown in Example 6 (FIG. 8 E-H, M), it is expected that intratumoral injection of oncolytic VC-TK⁻-hFlt3L would also be effective in treating large established B16-F10 in a unilateral implantation model.

All patent and literature documents cited herein are incorporated by reference in their entirety for all purposes.

What is claimed is:

1. A method for eliciting an immune response in a subject in need thereof, the method comprising delivering to the subject a therapeutically effective amount of a composition comprising a recombinant vaccinia virus selected from the group consisting of: (i) E3LΔ83N-TK⁻-hFlt3L; (ii) E3LΔ83N-TK⁻; (iii) E3LΔ83N-TK⁻-GM-CSF; and (iv) combinations thereof, wherein the virus is in replicative or inactivated form.

2. The method of claim 1, wherein the recombinant vaccinia virus comprises E3LΔ83N-TK⁻-hFlt3L in replicative or inactivated form.

3. The method of claim 1, wherein eliciting the immune response in the subject comprises one or more of the following immunological effects selected from:
increased activation of CD8⁺ T cells;
increased activation of CD4⁺ T cells; and
increased CD103⁺ dendritic cells.

4. The method of claim 1, wherein the recombinant vaccinia virus is delivered to the subject parenterally, intravenously, intratumorally, intraperitoneally, intrathecally, or intracranially.

5. The method of claim 1, wherein the recombinant vaccinia virus is heat-inactivated.

6. A method for treating a malignant solid tumor in a subject in need thereof, the method comprising delivering to the cells of the tumor a recombinant vaccinia virus in replicative or inactivated form selected from the group consisting of: (i) E3LΔ83N-TK⁻-hFlt3L; (ii) E3LΔ83N-TK⁻; (iii) E3LΔ83N-TK⁻-GM-CSF; and (iv) combinations thereof, in an amount effective to induce the immune system of the subject to mount an immune response against the tumor.

7. The method of claim 6, wherein the recombinant vaccinia virus comprises E3LΔ83N-TK⁻-hFlt3L in replicative or inactivated form.

8. The method of claim 6 wherein the tumor is primary or metastatic melanoma, breast carcinoma, or colon carcinoma.

9. The method of claim 6, wherein the immune response is systemic.

10. The method of claim 6, wherein the immune response is effective to accomplish one or more of the following: reduction of the size of the tumor; eradication of the tumor; inhibition of growth of the tumor; inhibition of metastasis of the tumor; or reduction or eradication of metastatic tumor.

11. The method of claim 6, wherein the tumor includes tumor located at the site of delivery, or tumor located at the site of delivery and elsewhere in the body of the subject.

12. The method of claim 6, wherein the immune response comprises one or more of the following:
increase in cytotoxic CD8⁺ T cells within the tumor and/or in tumor-draining lymph nodes;
induction of maturation of dendritic cells infiltrating the tumor through induction of type I IFN;
induction of activated CD4⁺ effector T cells in the subject recognizing tumor cells within the tumor or systemically; and
increase of CD103⁺ dendritic cells in non-injected tumors of the subject.

13. The method of claim 6, further comprising conjointly administering an immune checkpoint blocking agent in an amount effective to block immune suppressive mechanisms within the tumor elicited by tumor cells, stromal cells, or tumor infiltrating immune cells.

14. The method of claim 13, wherein the immune checkpoint blocking agent comprises CTLA-4 inhibitors, CD80 inhibitors, CD86 inhibitors, PD-1 inhibitors, PD-L1 inhibitors, PD-L2 inhibitors, LAG3 inhibitors, B7-H3 inhibitors, B7-H4 inhibitors, TIM3 inhibitors, ICOS inhibitors, II DLBCL inhibitors, BTLA inhibitors, ipilimumab, nivolumab, pembrolizumab, pidilizumab, AMP-224, MPDL3280A, BMS-936559, MEDI4736, MSB 00107180, or any combination thereof.

15. The method of claim 6, wherein the subject has been previously treated or dosed with an amount of an immune checkpoint blocking agent effective to block immune suppressive mechanisms within the tumor elicited by tumor cells, stromal cells, or tumor infiltrating immune cells.

16. The method of claim 15, wherein the immune checkpoint blocking agent comprises CTLA-4 inhibitors, CD80 inhibitors, CD86 inhibitors, PD-1 inhibitors, PD-L1 inhibitors, PD-L2 inhibitors, LAG3 inhibitors, B7-H3 inhibitors, B7-H4 inhibitors, TIM3 inhibitors, ICOS inhibitors, II DLBCL inhibitors, BTLA inhibitors, ipilimumab, nivolumab, pembrolizumab, pidilizumab, AMP-224, MPDL3280A, BMS-936559, MEDI4736, MSB 00107180, or any combination thereof.

17. The method of claim 6, wherein the recombinant vaccinia virus is delivered to the subject parenterally, intravenously, intratumorally, intraperitoneally, intrathecally, or intracranially.

18. The method of claim 6, further comprising combining the treatment with an additional treatment modality comprising surgery, chemotherapy, targeted therapy, and/or radiation.

19. The method of claim 6, wherein the recombinant vaccinia virus is heat-inactivated.

* * * * *